US010940187B2

(12) United States Patent
Fallon et al.

(10) Patent No.: US 10,940,187 B2
(45) Date of Patent: Mar. 9, 2021

(54) METHOD OF TREATMENT OF SCHIZOPHRENIFORM DISORDER

(71) Applicant: Curemark, LLC, Rye, NY (US)

(72) Inventors: Joan M. Fallon, Rye, NY (US); Matthew Heil, Sherman, CT (US); James Szigethy, Montgomery, NY (US); James Fallon, Armonk, NY (US)

(73) Assignee: CUREMARK, LLC, Rye, NY (US)

( * ) Notice: Subject to any disclaimer, the term of this patent is extended or adjusted under 35 U.S.C. 154(b) by 0 days.

(21) Appl. No.: 16/281,908

(22) Filed: Feb. 21, 2019

(65) Prior Publication Data

US 2019/0183990 A1  Jun. 20, 2019

Related U.S. Application Data

(63) Continuation of application No. 15/265,415, filed on Sep. 14, 2016, now Pat. No. 10,279,016, which is a continuation of application No. 14/612,604, filed on Feb. 3, 2015, now Pat. No. 9,492,515, which is a continuation of application No. 14/007,793, filed as application No. PCT/US2012/034489 on Apr. 20, 2012, now Pat. No. 8,980,252.

(60) Provisional application No. 61/477,988, filed on Apr. 21, 2011.

(51) Int. Cl.
| | |
|---|---|
| *A61P 25/18* | (2006.01) |
| *A61K 38/54* | (2006.01) |
| *A61K 38/46* | (2006.01) |
| *A61K 38/47* | (2006.01) |
| *A61K 38/48* | (2006.01) |
| *A61P 25/00* | (2006.01) |
| *A61K 45/06* | (2006.01) |
| *A61K 9/00* | (2006.01) |

(52) U.S. Cl.
CPC ............ *A61K 38/54* (2013.01); *A61K 9/0053* (2013.01); *A61K 38/465* (2013.01); *A61K 38/47* (2013.01); *A61K 38/48* (2013.01); *A61K 45/06* (2013.01); *A61P 25/00* (2018.01); *C12Y 301/01* (2013.01); *C12Y 302/01* (2013.01); *C12Y 304/00* (2013.01)

(58) Field of Classification Search
None
See application file for complete search history.

(56) References Cited

U.S. PATENT DOCUMENTS

| | | | |
|---|---|---|---|
| 3,002,883 A | 10/1961 | Butt et al. | |
| 3,223,594 A | 12/1965 | Hoek | |
| 3,322,626 A | 5/1967 | D'Argento | |
| 3,357,894 A | 12/1967 | Uriel et al. | |
| 3,515,642 A | 6/1970 | Hiroyuki et al. | |
| 3,536,809 A | 10/1970 | Applezweig et al. | |
| 3,574,819 A | 4/1971 | Franz et al. | |
| 3,598,123 A | 8/1971 | Zaffaroni | |
| 3,710,795 A | 1/1973 | Higuchi et al. | |
| 3,786,615 A | 1/1974 | Bauer | |
| 3,845,770 A | 11/1974 | Theeuwes et al. | |
| 3,860,708 A | 1/1975 | Prout | |
| 3,916,899 A | 11/1975 | Theeuwes et al. | |
| 3,940,478 A | 2/1976 | Kurtz | |
| RE28,819 E | 5/1976 | Thompson | |
| 4,008,719 A | 2/1977 | Theeuwes et al. | |
| 4,044,126 A | 8/1977 | Cook et al. | |
| 4,079,125 A | 3/1978 | Sipos | |
| 4,145,410 A | 3/1979 | Sears | |
| 4,199,322 A | 4/1980 | Danna et al. | |
| 4,241,046 A | 12/1980 | Papahadjopoulos et al. | |
| 4,280,971 A | 7/1981 | Wischniewski et al. | |
| 4,328,245 A | 5/1982 | Yu et al. | |
| 4,358,603 A | 11/1982 | Yu | |
| 4,364,923 A | 12/1982 | Cook et al. | |
| 4,395,454 A | 7/1983 | Baldwin | |
| 4,409,239 A | 10/1983 | Yu | |
| 4,410,545 A | 10/1983 | Yu et al. | |
| 4,414,209 A | 11/1983 | Cook et al. | |
| 4,447,412 A | 5/1984 | Bilton | |
| 4,456,544 A | 6/1984 | Lupova et al. | |
| 4,500,515 A | 2/1985 | Libby | |

(Continued)

FOREIGN PATENT DOCUMENTS

| | | |
|---|---|---|
| CA | 2198317 A1 | 8/1998 |
| CA | 2263703 A1 | 8/1999 |

(Continued)

OTHER PUBLICATIONS

U.S. Appl. No. 12/535,676 Notice of Allowance dated Apr. 1, 2020.
U.S. Appl. No. 13/757,412 Non-Final Office Action dated Mar. 18, 2020.
U.S. Appl. No. 14/713,242 Notice of Allowance dated Apr. 2, 2020.
U.S. Appl. No. 15/074,115 Notice of Allowance dated Dec. 11, 2019.
U.S. Appl. No. 15/074,115 Notice of Allowance dated Feb. 11, 2020.
U.S. Appl. No. 15/265,620 Non-Final Office Action dated Jan. 30, 2020.
U.S. Appl. No. 15/889,917 Office Action dated May 24, 2019.
U.S. Appl. No. 16/296,546 Non-Final Office Action dated Feb. 14, 2020.

(Continued)

*Primary Examiner* — Ralph J Gitomer

(74) *Attorney, Agent, or Firm* — Wilson Sonsini Goodrich & Rosati

(57) ABSTRACT

Disclosed in this application are compositions which include digestive enzymes and which are formulated to reduce one or more symptoms of Schizophrenia or a Schizophreniform Disorder. Also disclosed is a method for treating an individual with Schizophrenia or a Schizophreniform Disorder using digestive enzymes and their derivatives to alleviate the symptoms of Schizophrenia or a Schizophreniform Disorder. The method comprises administering to the individual an effective amount of digestive enzymes that are either naturally or recombinantly derived, or their derivatives, in an amount effective to reduce one or more symptoms of Schizophrenia or a Schizophreniform Disorder.

20 Claims, 8 Drawing Sheets

(56) References Cited

U.S. PATENT DOCUMENTS

| | | | |
|---|---|---|---|
| 4,623,624 A | 11/1986 | Schultze | |
| 4,710,384 A | 12/1987 | Rotman | |
| 4,826,679 A | 5/1989 | Roy | |
| 5,023,108 A | 6/1991 | Bagaria et al. | |
| 5,059,595 A | 10/1991 | Le Grazie | |
| 5,073,543 A | 12/1991 | Marshall et al. | |
| 5,120,548 A | 6/1992 | McClelland et al. | |
| 5,190,775 A | 3/1993 | Klose | |
| 5,227,166 A | 7/1993 | Ueda et al. | |
| 5,250,418 A | 10/1993 | Moller et al. | |
| 5,324,514 A | 6/1994 | Sipos | |
| 5,354,556 A | 10/1994 | Sparks et al. | |
| 5,378,462 A | 1/1995 | Boedecker et al. | |
| 5,436,319 A | 7/1995 | Kung et al. | |
| 5,437,319 A | 8/1995 | Garuglieri | |
| 5,439,935 A | 8/1995 | Rawlings et al. | |
| 5,460,812 A | 10/1995 | Sipos | |
| 5,476,661 A | 12/1995 | Pillai et al. | |
| 5,527,678 A | 6/1996 | Blaser et al. | |
| 5,585,115 A | 12/1996 | Sherwood et al. | |
| 5,591,767 A | 1/1997 | Mohr et al. | |
| 5,607,863 A | 3/1997 | Chandler | |
| 5,639,476 A | 6/1997 | Oshlack et al. | |
| 5,648,335 A | 7/1997 | Lewis et al. | |
| 5,674,532 A | 10/1997 | Atzl et al. | |
| 5,674,533 A | 10/1997 | Santus et al. | |
| 5,686,255 A * | 11/1997 | Deth | A61K 49/0004 435/7.21 |
| 5,686,311 A | 11/1997 | Shaw | |
| 5,750,104 A | 5/1998 | Sipos | |
| 5,753,223 A | 5/1998 | Shibahara et al. | |
| 5,776,917 A | 7/1998 | Blank et al. | |
| 5,858,758 A | 1/1999 | Hillman et al. | |
| 5,860,957 A | 1/1999 | Jacobsen et al. | |
| 5,948,433 A | 9/1999 | Burton et al. | |
| 5,952,178 A | 9/1999 | Lapidus et al. | |
| 5,958,875 A | 9/1999 | Longo et al. | |
| 5,977,175 A | 11/1999 | Lin | |
| 5,983,134 A | 11/1999 | Ostrow | |
| 5,985,317 A | 11/1999 | Venkateshwaran et al. | |
| 5,985,891 A | 11/1999 | Rowe | |
| 6,010,715 A | 1/2000 | Wick et al. | |
| 6,011,001 A | 1/2000 | Navia et al. | |
| 6,013,286 A | 1/2000 | Klose | |
| 6,020,310 A | 2/2000 | Beck et al. | |
| 6,020,314 A | 2/2000 | McMichael | |
| 6,024,975 A | 2/2000 | D'Angelo et al. | |
| 6,096,338 A | 8/2000 | Lacy et al. | |
| 6,100,080 A | 8/2000 | Johansen | |
| 6,149,585 A | 11/2000 | Gray | |
| 6,153,236 A | 11/2000 | Wu et al. | |
| 6,167,301 A | 12/2000 | Flower et al. | |
| 6,168,569 B1 | 1/2001 | McEwen et al. | |
| 6,187,309 B1 | 2/2001 | McMichael et al. | |
| 6,197,746 B1 | 3/2001 | Beck et al. | |
| 6,210,950 B1 | 4/2001 | Johnson et al. | |
| 6,238,727 B1 | 5/2001 | Takemoto et al. | |
| 6,251,478 B1 | 6/2001 | Pacifico et al. | |
| 6,256,533 B1 | 7/2001 | Yuzhakov et al. | |
| 6,261,595 B1 | 7/2001 | Stanley et al. | |
| 6,261,602 B1 | 7/2001 | Calanchi et al. | |
| 6,261,613 B1 | 7/2001 | Narayanaswamy et al. | |
| 6,267,983 B1 | 7/2001 | Fujii et al. | |
| 6,280,726 B1 | 8/2001 | Weinrauch et al. | |
| 6,287,585 B1 | 9/2001 | Johansen | |
| 6,309,669 B1 | 10/2001 | Setterstrom et al. | |
| 6,312,741 B1 | 11/2001 | Navarro | |
| 6,399,101 B1 | 6/2002 | Frontanes et al. | |
| 6,482,839 B1 | 11/2002 | Thornfeldt | |
| 6,498,143 B1 | 12/2002 | Beck et al. | |
| 6,534,063 B1 | 3/2003 | Fallon | |
| 6,534,259 B1 | 3/2003 | Wakefield | |
| 6,558,708 B1 | 5/2003 | Lin | |
| 6,562,629 B1 | 5/2003 | Lin et al. | |
| 6,569,463 B2 | 5/2003 | Patel et al. | |
| 6,616,954 B1 | 9/2003 | Dally et al. | |
| 6,632,429 B1 | 10/2003 | Fallon | |
| 6,660,831 B2 | 12/2003 | Fallon | |
| 6,699,885 B2 | 3/2004 | Phillips | |
| 6,727,073 B1 | 4/2004 | Moore et al. | |
| 6,743,447 B2 | 6/2004 | Labergerie et al. | |
| 6,764,447 B2 | 7/2004 | Iliff | |
| 6,783,757 B2 | 8/2004 | Brudnak | |
| 6,790,825 B2 | 9/2004 | Beck et al. | |
| 6,797,291 B2 | 9/2004 | Richardson | |
| 6,808,708 B2 | 10/2004 | Houston | |
| 6,821,514 B2 | 11/2004 | Houston | |
| 6,827,688 B2 | 12/2004 | Goto et al. | |
| 6,835,397 B2 | 12/2004 | Lee et al. | |
| 6,852,487 B1 | 2/2005 | Barany et al. | |
| 6,861,053 B1 | 3/2005 | Lin et al. | |
| 6,890,561 B1 | 5/2005 | Blatt et al. | |
| 6,899,876 B2 | 5/2005 | Houston | |
| 6,923,988 B2 | 8/2005 | Patel et al. | |
| 6,980,958 B1 | 12/2005 | Surwit et al. | |
| 7,048,906 B2 | 5/2006 | Lin et al. | |
| 7,081,239 B2 | 7/2006 | Lin | |
| 7,091,182 B2 | 8/2006 | Beck et al. | |
| 7,101,573 B2 | 9/2006 | Szymczak et al. | |
| 7,122,357 B2 | 10/2006 | Sander-Struckmeier et al. | |
| 7,129,053 B1 | 10/2006 | Reiter et al. | |
| 7,138,123 B2 | 11/2006 | Fallon | |
| 7,232,670 B2 | 6/2007 | D'Azzo et al. | |
| 7,244,412 B2 | 7/2007 | Lin | |
| 7,285,633 B2 | 10/2007 | Wu et al. | |
| RE40,059 E | 2/2008 | Pacifico et al. | |
| 7,381,698 B2 | 6/2008 | Fein et al. | |
| 7,395,216 B2 | 7/2008 | Rosenfeld et al. | |
| 7,479,378 B2 | 1/2009 | Potthoff et al. | |
| 7,483,747 B2 | 1/2009 | Gliner et al. | |
| 7,588,757 B2 | 9/2009 | Ozawa et al. | |
| 7,608,245 B2 | 10/2009 | Lin | |
| 7,630,913 B2 | 12/2009 | Kay | |
| 7,658,918 B1 | 2/2010 | Ortenzi et al. | |
| 7,718,169 B2 | 5/2010 | Margolin et al. | |
| 7,736,622 B2 | 6/2010 | Lin et al. | |
| 7,935,799 B2 | 5/2011 | Lin et al. | |
| 7,945,451 B2 | 5/2011 | Cosentino et al. | |
| 8,008,036 B2 | 8/2011 | Fallon | |
| 8,012,710 B2 | 9/2011 | Fallon | |
| 8,012,930 B2 | 9/2011 | Fallon | |
| 8,030,002 B2 | 10/2011 | Fallon | |
| 8,055,516 B2 | 11/2011 | Iliff | |
| 8,066,636 B2 | 11/2011 | Iliff | |
| 8,084,025 B2 * | 12/2011 | Fallon | A61K 38/47 424/94.6 |
| 8,105,584 B2 | 1/2012 | Fallon | |
| 8,163,278 B2 | 4/2012 | Fallon | |
| 8,187,209 B1 | 5/2012 | Giuffrida | |
| 8,211,661 B2 | 7/2012 | Fallon | |
| 8,221,747 B2 | 7/2012 | Ortenzi et al. | |
| 8,318,158 B2 | 11/2012 | Fallon | |
| 8,437,689 B2 | 5/2013 | Mazar | |
| 8,486,390 B2 | 7/2013 | Fallon | |
| 8,580,522 B2 | 11/2013 | Fallon | |
| 8,613,918 B2 | 12/2013 | Fallon | |
| 8,658,163 B2 | 2/2014 | Fallon | |
| 8,673,877 B2 | 3/2014 | Fallon et al. | |
| 8,778,335 B2 | 7/2014 | Fallon | |
| 8,815,233 B2 | 8/2014 | Fallon | |
| 8,921,054 B2 | 12/2014 | Fallon | |
| 8,980,252 B2 * | 3/2015 | Fallon | A61K 38/54 424/94.2 |
| 9,017,665 B2 | 4/2015 | Fallon | |
| 9,023,344 B2 | 5/2015 | Fallon | |
| 9,056,050 B2 * | 6/2015 | Fallon | A61K 9/009 |
| 9,061,033 B2 | 6/2015 | Fallon | |
| 9,084,784 B2 | 7/2015 | Fallon et al. | |
| 9,107,419 B2 | 8/2015 | Fallon et al. | |
| 9,233,146 B2 | 1/2016 | Fallon | |
| 9,320,780 B2 | 4/2016 | Fallon | |
| 9,345,721 B2 | 5/2016 | Fallon et al. | |
| 9,377,459 B2 | 6/2016 | Fallon | |
| 9,408,895 B2 | 8/2016 | Fallon | |

(56) References Cited

U.S. PATENT DOCUMENTS

| | | | |
|---|---|---|---|
| 9,492,515 B2 * | 11/2016 | Fallon | A61K 38/48 |
| 9,511,125 B2 | 12/2016 | Fallon et al. | |
| 9,624,525 B2 | 4/2017 | Fallon | |
| 9,624,526 B2 | 4/2017 | Fallon | |
| 9,687,534 B2 | 6/2017 | Fallon | |
| 9,895,427 B2 | 2/2018 | Fallon et al. | |
| 9,925,250 B2 | 3/2018 | Fallon | |
| 9,931,302 B2 | 4/2018 | Fallon et al. | |
| 10,098,844 B2 | 10/2018 | Fallon et al. | |
| 10,209,253 B2 | 2/2019 | Fallon | |
| 10,272,141 B2 | 4/2019 | Fallon | |
| 10,279,016 B2 * | 5/2019 | Fallon | A61K 38/54 |
| 10,350,229 B2 | 7/2019 | Fallon et al. | |
| 10,350,278 B2 | 7/2019 | Fallon et al. | |
| 2001/0006644 A1 | 7/2001 | Bova et al. | |
| 2001/0023360 A1 | 9/2001 | Nelson et al. | |
| 2001/0024660 A1 | 9/2001 | Ullah et al. | |
| 2002/0001575 A1 | 1/2002 | Foreman | |
| 2002/0037284 A1 | 3/2002 | Fallon | |
| 2002/0061302 A1 | 5/2002 | Sander-Struckmeier et al. | |
| 2002/0081628 A1 | 6/2002 | Fallon | |
| 2002/0090653 A1 | 7/2002 | Fallon | |
| 2002/0094367 A1 | 7/2002 | Fuglsang et al. | |
| 2002/0103675 A1 | 8/2002 | Vanelli | |
| 2002/0119914 A1 | 8/2002 | Zhu et al. | |
| 2002/0141987 A1 | 10/2002 | Bjarnason | |
| 2002/0183229 A1 | 12/2002 | Simpson | |
| 2003/0097122 A1 | 5/2003 | Ganz et al. | |
| 2004/0005304 A1 | 1/2004 | Brudnak | |
| 2004/0028689 A1 | 2/2004 | Borody | |
| 2004/0029752 A1 | 2/2004 | Sava et al. | |
| 2004/0057944 A1 | 3/2004 | Galle et al. | |
| 2004/0057962 A1 | 3/2004 | Timmerman | |
| 2004/0071683 A1 | 4/2004 | Fallon | |
| 2004/0076590 A1 | 4/2004 | Wilkins | |
| 2004/0101562 A1 | 5/2004 | Maio | |
| 2004/0121002 A1 | 6/2004 | Lee et al. | |
| 2004/0209790 A1 | 10/2004 | Sava et al. | |
| 2005/0026892 A1 | 2/2005 | Bodor | |
| 2005/0036950 A1 | 2/2005 | Jones et al. | |
| 2005/0079594 A1 | 4/2005 | Marion | |
| 2005/0137134 A1 | 6/2005 | Gill et al. | |
| 2005/0170479 A1 | 8/2005 | Weaver et al. | |
| 2005/0187130 A1 | 8/2005 | Brooker et al. | |
| 2005/0232894 A1 | 10/2005 | Weiner et al. | |
| 2006/0105379 A1 | 5/2006 | Wu et al. | |
| 2006/0115467 A1 | 6/2006 | Pangborn et al. | |
| 2006/0121017 A1 | 6/2006 | Margolin et al. | |
| 2006/0182728 A1 | 8/2006 | Fallon | |
| 2006/0183180 A1 | 8/2006 | Fallon | |
| 2006/0198838 A1 | 9/2006 | Fallon | |
| 2006/0253045 A1 | 11/2006 | Coifman | |
| 2006/0258599 A1 | 11/2006 | Childers | |
| 2006/0259995 A1 | 11/2006 | Cayouette et al. | |
| 2006/0294108 A1 | 12/2006 | Adelson et al. | |
| 2007/0031399 A1 | 2/2007 | Edens et al. | |
| 2007/0053895 A1 | 3/2007 | Fallon | |
| 2007/0092501 A1 | 4/2007 | Houston | |
| 2007/0116695 A1 | 5/2007 | Fallon | |
| 2007/0148151 A1 | 6/2007 | Frink et al. | |
| 2007/0148152 A1 | 6/2007 | Shlieout et al. | |
| 2007/0148153 A1 | 6/2007 | Shlieout et al. | |
| 2007/0203426 A1 | 8/2007 | Kover et al. | |
| 2007/0250119 A1 | 10/2007 | Tyler et al. | |
| 2008/0019959 A1 | 1/2008 | Becher et al. | |
| 2008/0020036 A1 | 1/2008 | Jolly | |
| 2008/0057086 A1 | 3/2008 | Etter | |
| 2008/0058282 A1 | 3/2008 | Fallon et al. | |
| 2008/0112900 A1 | 5/2008 | Du-Thumm et al. | |
| 2008/0112944 A1 | 5/2008 | Pangborn et al. | |
| 2008/0152637 A1 | 6/2008 | Fallon | |
| 2008/0161265 A1 | 7/2008 | Fallon et al. | |
| 2008/0166334 A1 | 7/2008 | Fallon | |
| 2008/0177578 A1 | 7/2008 | Zakim | |
| 2008/0187525 A1 | 8/2008 | Porubcan | |
| 2008/0199448 A1 | 8/2008 | Ross et al. | |
| 2008/0219966 A1 | 9/2008 | Fallon | |
| 2008/0248558 A1 | 10/2008 | Deinhammer et al. | |
| 2008/0254009 A1 | 10/2008 | Finegold | |
| 2008/0274174 A1 | 11/2008 | Ortenzi et al. | |
| 2008/0279839 A1 | 11/2008 | Schuler et al. | |
| 2008/0279953 A1 | 11/2008 | Ortenzi et al. | |
| 2008/0311554 A1 | 12/2008 | Slotman | |
| 2008/0317731 A1 | 12/2008 | Gramatikova et al. | |
| 2009/0004285 A1 | 1/2009 | Yu et al. | |
| 2009/0018407 A1 | 1/2009 | Jung et al. | |
| 2009/0063402 A1 | 3/2009 | Hayter | |
| 2009/0110674 A1 | 4/2009 | Loizou | |
| 2009/0117180 A1 | 5/2009 | Ortenzi et al. | |
| 2009/0130081 A1 | 5/2009 | Fallon | |
| 2009/0171696 A1 | 7/2009 | Allard et al. | |
| 2009/0197289 A1 | 8/2009 | Fallon | |
| 2009/0226414 A1 | 9/2009 | Tijssen et al. | |
| 2009/0232789 A1 | 9/2009 | Fallon | |
| 2009/0233344 A1 | 9/2009 | Kurfurst et al. | |
| 2009/0263372 A1 | 10/2009 | Fallon | |
| 2009/0285790 A1 | 11/2009 | Fallon | |
| 2009/0286270 A1 | 11/2009 | Fallon | |
| 2009/0304670 A1 | 12/2009 | Edens et al. | |
| 2009/0324572 A1 | 12/2009 | Fallon | |
| 2009/0324730 A1 | 12/2009 | Fallon | |
| 2010/0092447 A1 | 4/2010 | Fallon | |
| 2010/0169409 A1 | 7/2010 | Fallon et al. | |
| 2010/0196344 A1 | 8/2010 | Margolin et al. | |
| 2010/0209507 A1 | 8/2010 | Lin et al. | |
| 2010/0233218 A1 | 9/2010 | Fallon | |
| 2010/0239559 A1 | 9/2010 | Freedman et al. | |
| 2010/0260857 A1 | 10/2010 | Fallon et al. | |
| 2010/0270183 A1 | 10/2010 | Ortenzi et al. | |
| 2010/0285116 A1 | 11/2010 | Joshi | |
| 2011/0029922 A1 | 2/2011 | Hoffberg et al. | |
| 2011/0052706 A1 | 3/2011 | Moest et al. | |
| 2011/0065628 A1 | 3/2011 | Johnson et al. | |
| 2011/0081320 A1 | 4/2011 | Westall et al. | |
| 2011/0112005 A1 | 5/2011 | Brooker et al. | |
| 2011/0182818 A1 | 7/2011 | Fallon | |
| 2011/0200574 A1 | 8/2011 | Jolly et al. | |
| 2011/0280854 A1 | 11/2011 | Fallon et al. | |
| 2012/0003628 A1 | 1/2012 | Fallon | |
| 2012/0004192 A1 | 1/2012 | Fallon et al. | |
| 2012/0027848 A1 | 2/2012 | Fallon et al. | |
| 2012/0070504 A1 | 3/2012 | Fallon | |
| 2012/0128764 A1 | 5/2012 | Venkatesh et al. | |
| 2012/0189703 A1 | 7/2012 | Fallon et al. | |
| 2012/0201875 A1 | 8/2012 | Ortenzi et al. | |
| 2012/0207740 A1 | 8/2012 | Fallon | |
| 2012/0230970 A1 | 9/2012 | Fallon | |
| 2013/0059001 A1 | 3/2013 | Fallon | |
| 2013/0095152 A1 | 4/2013 | Fallon | |
| 2013/0113129 A1 | 5/2013 | Fallon et al. | |
| 2013/0195833 A1 | 8/2013 | Fallon | |
| 2013/0202581 A1 | 8/2013 | Fallon et al. | |
| 2013/0224172 A1 | 8/2013 | Fallon et al. | |
| 2014/0030333 A1 | 1/2014 | Fallon | |
| 2014/0127184 A1 | 5/2014 | Fallon et al. | |
| 2014/0147500 A1 | 5/2014 | Fallon et al. | |
| 2014/0161787 A1 | 6/2014 | Fallon | |
| 2014/0170637 A1 | 6/2014 | Fallon | |
| 2014/0348881 A1 | 11/2014 | Fallon | |
| 2015/0023944 A1 | 1/2015 | Fallon | |
| 2015/0147308 A1 | 5/2015 | Fallon et al. | |
| 2015/0151198 A1 | 6/2015 | Dugan et al. | |
| 2015/0182607 A1 | 7/2015 | Jolly et al. | |
| 2015/0246105 A1 | 9/2015 | Fallon et al. | |
| 2015/0273030 A1 | 10/2015 | Fallon | |
| 2015/0335589 A1 | 11/2015 | Fallon et al. | |
| 2016/0045576 A1 | 2/2016 | Fallon | |
| 2016/0206708 A1 | 7/2016 | Fallon et al. | |
| 2017/0157221 A1 | 6/2017 | Fallon | |
| 2017/0246265 A1 | 8/2017 | Fallon | |
| 2018/0071375 A1 | 3/2018 | Fallon | |
| 2018/0078623 A1 | 3/2018 | Fallon | |
| 2018/0104315 A1 | 4/2018 | Fallon | |
| 2018/0161409 A1 | 6/2018 | Fallon | |

(56) References Cited

U.S. PATENT DOCUMENTS

| | | | |
|---|---|---|---|
| 2018/0243282 A1 | 8/2018 | Fallon | |
| 2018/0296650 A1 | 10/2018 | Fallon | |
| 2018/0360759 A1 | 12/2018 | Fallon | |
| 2019/0175704 A1 | 6/2019 | Fallon | |
| 2019/0201507 A1 | 7/2019 | Fallon | |
| 2019/0209667 A1 | 7/2019 | Fallon | |
| 2019/0275066 A1 | 9/2019 | Fallon et al. | |
| 2019/0275128 A1 | 9/2019 | Fallon et al. | |
| 2020/0282030 A1 | 9/2020 | Fallon et al. | |
| 2020/0286620 A1 | 9/2020 | Fallon et al. | |

FOREIGN PATENT DOCUMENTS

| | | | |
|---|---|---|---|
| CA | 2667976 A1 | 5/2008 | |
| CN | 1031562 A | 3/1989 | |
| CN | 1275897 A | 12/2000 | |
| CN | 1329923 A | 1/2002 | |
| CN | 1552836 A | 12/2004 | |
| CN | 101040052 A | 9/2007 | |
| DE | 3738599 A1 | 5/1989 | |
| DE | 4332985 A1 | 3/1995 | |
| DE | 202010004926 U1 | 7/2010 | |
| EP | 0425214 A2 | 5/1991 | |
| EP | 0436110 A1 | 7/1991 | |
| EP | 0451484 A1 | 10/1991 | |
| EP | 0564739 A2 | 10/1993 | |
| EP | 0564739 A3 | 4/1995 | |
| EP | 1162995 B1 | 6/2003 | |
| EP | 1413202 A1 | 4/2004 | |
| EP | 1335706 B1 | 4/2005 | |
| EP | 1019072 B1 | 5/2005 | |
| EP | 1604677 A1 | 12/2005 | |
| EP | 1931317 B1 | 12/2008 | |
| EP | 2258837 A1 | 12/2010 | |
| GB | 669782 A | 4/1952 | |
| GB | 2347742 A | 9/2000 | |
| JP | S523819 A | 1/1977 | |
| JP | S62230714 A | 10/1987 | |
| JP | H04364119 A | 12/1992 | |
| JP | 2001508677 A | 7/2001 | |
| JP | 2003517831 A | 6/2003 | |
| JP | 2004500591 A | 1/2004 | |
| JP | 2005515223 A | 5/2005 | |
| JP | 2006512091 A | 4/2006 | |
| JP | 2007523664 A | 8/2007 | |
| JP | 2007530503 A | 11/2007 | |
| JP | 2008512468 A | 4/2008 | |
| JP | 2008521906 A | 6/2008 | |
| JP | 2008283895 A | 11/2008 | |
| JP | 2013517251 A | 5/2013 | |
| KR | 20050084485 A | 8/2005 | |
| RU | 2356244 C1 | 5/2009 | |
| TW | 310277 B | 7/1997 | |
| WO | WO-8402846 A1 | 8/1984 | |
| WO | WO-8908694 A1 | 9/1989 | |
| WO | WO-9002562 A1 | 3/1990 | |
| WO | WO-9219708 A1 | 11/1992 | |
| WO | WO-9219709 A1 | 11/1992 | |
| WO | WO-9419005 A1 | 9/1994 | |
| WO | WO-9522344 A1 | 8/1995 | |
| WO | WO-9732480 A1 | 9/1997 | |
| WO | WO-9822499 A2 | 5/1998 | |
| WO | WO-9826807 A1 | 6/1998 | |
| WO | WO-9822499 A3 | 7/1998 | |
| WO | WO-9832336 A2 | 7/1998 | |
| WO | WO-9852593 A1 | 11/1998 | |
| WO | WO-9964059 A2 | 12/1999 | |
| WO | WO-0009142 A1 | 2/2000 | |
| WO | WO-9964059 A3 | 3/2000 | |
| WO | WO-0021504 A1 | 4/2000 | |
| WO | WO-0127612 A2 | 4/2001 | |
| WO | WO-0145835 A1 | 6/2001 | |
| WO | WO-0127612 A3 | 10/2001 | |
| WO | WO-0219828 A1 | 3/2002 | |
| WO | WO-02051352 A2 | 7/2002 | |
| WO | WO-02051436 A2 | 7/2002 | |
| WO | WO-03051345 A2 | 6/2003 | |
| WO | WO-03059088 A1 | 7/2003 | |
| WO | WO-2004060074 A1 | 7/2004 | |
| WO | WO-2004093883 A2 | 11/2004 | |
| WO | WO-2005092370 A1 | 10/2005 | |
| WO | WO-2005115445 A1 | 12/2005 | |
| WO | WO-2006031554 A2 | 3/2006 | |
| WO | WO-2006044529 A1 | 4/2006 | |
| WO | WO-2006060414 A2 | 6/2006 | |
| WO | WO-2006031554 A3 | 9/2006 | |
| WO | WO-2007002572 A2 | 1/2007 | |
| WO | WO-2007074454 A2 | 7/2007 | |
| WO | WO-2007147714 A1 | 12/2007 | |
| WO | WO-2008013747 A2 | 1/2008 | |
| WO | WO-2008021987 A2 | 2/2008 | |
| WO | WO-2008102264 A2 | 8/2008 | |
| WO | WO-2009155689 A1 | 12/2009 | |
| WO | WO-2010025126 A1 | 3/2010 | |
| WO | WO-2011000924 A1 | 1/2011 | |
| WO | WO-2011114225 A1 | 9/2011 | |
| WO | WO-2012145651 A2 | 10/2012 | |
| WO | WO-2013103746 A1 | 7/2013 | |
| WO | WO-2013116732 A1 | 8/2013 | |
| WO | WO-2013181447 A1 | 12/2013 | |

OTHER PUBLICATIONS

Wang et al., Extraction of Pancreatin from Pig Pancreas and Isolation and Purification of Kallikrein. Academic Journal of Kunming Medical College 1: 107-108 (2002).

U.S. Appl. No. 11/533,818 Final Office Action dated Jun. 7, 2016.

U.S. Appl. No. 12/054,343 Final Office Action dated May 10, 2017.

U.S. Appl. No. 12/054,343 Office Action dated Aug. 19, 2016.

U.S. Appl. No. 12/535,676 Non-Final Office Action dated Apr. 21, 2017.

U.S. Appl. No. 13/705,763 Final Office Action dated May 24, 2016.

U.S. Appl. No. 14/640,385 Supplemental Notice of Allowability dated May 26, 2016.

U.S. Appl. No. 14/713,221 Notice of Allowance dated Oct. 19, 2017.

ABCnews. Changing Face of Autism: Numbers Rise as More Behaviors Included. ABCnews. Nov. 1, 2007.

Adams. "Summary of Defeat Autism Now! (DNN!) Oct. 2001 Conference," retrieved from the internet Dec. 18, 2008. http://puterakembara.org/rm/DAN2001.htm.

Advisory Action dated Jun. 3, 2008 for U.S. Appl. No. 10/681,018.

Axelrod FB et al. Hereditary sensory an autonomic neuropathies: types II, III and IV. Orphanet Journal of Rare Diseases, 2:39 (2007).

Aman, et al. Outcome measures for clinical drug trials in autism. CNS Spectr. Jan. 2004;9(1):36-47.

Anderson, George M., et al. Determination of serotonin in whole blood, platelet-rich plasma, platelet-poor plasma and plasma ultrafiltrate. Life Sciences 40(11):1063-1070 (Mar. 16, 1987) [Abstract Only].

Ang, et al. Biological role and regulation of the universally conserved heat shock proteins. J Biol Chem. Dec. 25, 1991;266(36):24233-6.

Anonymous: Emulsifiers for the preparation of active dry yeast, Research Disclosure, Mason Publications, Hampshire, GB, 236(6), Dec. 1983.

APDA. Basic Information About Parkinson's Disease. Jul. 14, 2008.

Arnold, GL et al. Plasma amino acids profiles in children with autism: potential risk of nutritional deficiencies. J. Autism Dev. Disord. 33(4):449-454 (Aug. 2003) [Abstract Only].

Arribas, et al. A comparative study of the chymotrypsin-like activity of the rat liver multicatalytic proteinase and the ClpP from *Escherichia coli*. J Biol Chem. Oct. 5, 1993;268(28):21165-71.

Arrigo, et al. Expression of heat shock proteins during development in *Drosophila*. Results Probl Cell Differ. 1991;17:106-19.

Ash. Patient Information Guide—Understanding Hypertension. American Society of Hypertension. 2004. 1-7.

(56) References Cited

OTHER PUBLICATIONS

Ashwood, et al. Immune activation of peripheral blood and mucosal CD3+ lymphocyte cytokine profiles in children with autism and gastrointestinal symptoms. J Neuroimmunol. Dec. 19, 2005; 1-9.

Ashwood, et al. Intestinal lymphocyte populations in children with regressive autism: evidence for extensive mucosal immunopathology. J Clin Immunol. Nov. 2003;23(6):504-17.

Ashwood, et al. Spontaneous mucosal lymphocyte cytokine profiles in children with autism and gastrointestinal symptoms: mucosal immune activation and reduced counter regulatory interleukin-10. J Clin Immunol. Nov. 2004;24(6):664-73.

Austic. Development and adaptation of protein digestion. J Nutr. May 1985;115(5):686-97.

Autism Diagnosis. Autism Statistics. Www.autism-diagnosis.com/autism_statistics/autism_statistics.html. 2007.

Autism Society of America. Incidence Numbers from Other Countries. www.autism-society.org. Accessed: Jul. 14, 2008.

Avruch, J., et al. Amino acid regulation of TOR complex 1. AJP: Endocrinology and Metabolism, Am. J. Physiol. Endocrinol. Metab. 296(4):E592-E602 (Apr. 2009).

Awazuhara, et al. Antigenicity of the proteins in soy lecithin and soy oil in soybean allergy. Clin Exp Allergy. Dec. 1998;28(12):1559-64.

Axcan Pharma Inc. CDN Prescribing Information on VIOKASE Pancrelipase, USP tablets, powder. 2000: 1-3.

Axelrod. Secretin Treatment for Gastrointestinal Dysmobility in Patients with Familial Dysautonomia. New York University School of Medicine, Grant Recipient awards, Mar.-May 2000. www.med.nyu.edu/ogars/awards/awards2000/page2.html.

Azilect et al. "Correlation between protein intake and daily levodopa dosage," Obtained from the internet May 2, 2007, http://www.azilect.eu/media/cnsnews/showitem.aspx?i=d1c603e4-3c61-4aa1-a376-6e519a5a0f80.

Bailey, et al. Co-occurring conditions associated with FMR1 gene variations: findings from a national parent survey. Am J Med Genet A. Aug. 15, 2008;146A(16):2060-9.

Bakkaloglu, et al. Atopic features in early childhood autism. Eur J Paediatr Neurol. Nov. 2008;12(6):476-9.

Balasubramanian, Mukundh N. et al. Asparagine synthetase: regulation by cell stress and involvement in tumor biology, Am. J. Physiol. Endocrinol. Metab. 304(8):E789-E799 (Apr. 15, 2013).

Barlow. A comparison of the blood pressure, kidney volume and the pancreatic secretory response following the vein administration of various secretin preparations. Am J Phys. 1927;81:182-188.

Barnhart, et al. Symptomatic granular cell tumor involving the pituitary gland in a dog: a case report and review of the literature. Vet Pathol. May 2001;38(3):332-6.

Beilmann, et al. Neoexpression of the c-met/hepatocyte growth factor-scatter factor receptor gene in activated monocytes. Blood. Dec. 1, 1997;90(11):4450-8.

Beliaev, O.A. The therapeutic efficacy of the triase preparation in experimental pancreatic exocrine insufficiency. Eksp Lin Farmakiol. 57:38-40 (1994) (Abstract Only—English Translation).

Bellanti, et al. Abnormalities of Th1 function in non-IgE food allergy, celiac disease, and ileal lymphonodular hyperplasia: a new relationship? Ann Allergy Asthma Immunol. Jun. 2003;90(6 Suppl 3):84-9.

Belmonte et al. Fragile X syndrome and autism at the intersection of genetic and neural networks. Nat Neurosci. Oct. 2006; 9(10):1221-5 (abstract only).

Berg, et al. Section 10.5 Many Enzymes Are Actived by Specific Proteolytic Cleavage. 2002.

Berg, et al. Section 9.1 Proteases: Facilitating a Difficult Reaction. 2002.

Berg, et al. Table of Contents. Biochemistry, 5th edition. 2002.

Bhattacharjee et al., Treatment of Pancreatic Exocrine Insufficiency with Enteric Coated Pancreatin Formulations: An Overview. International Journal of Pharmaceutical Sciences and Nanotechnology. 6(3):2125-2130 (2013).

Birnbaum, et al. Heat shock or stress proteins and their role as autoantigens in multiple sclerosis. Ann N Y Acad Sci. Dec. 19, 1997;835:157-67. Abstract only.

Blackmer. Parkinson disease: treatment and medication. Mar. 10, 2009., retrieved from the internet on Sep. 15, 2009, http://emedicine.medscape.com/article/312519-treatment.

Block, et al. A rapid food screener to assess fat and fruit and vegetable intake. Am J Prev Med. May 2000;18(4):284-8.

Blog. Acid Phosphatase Research (blog). Acid-phosphatase.blogspot.com. 2008.

Bode et al. Usefulness of a simple photometric determination of chymotrypsin activity in stools-results of a multicentre study. Clin Biochem. 1986; 19:333-37.

Boorom. Is this recently characterized gastrointestinal pathogen responsible for rising rates of inflammatory bowel disease (IBD) and IBD associated autism in Europe and the United States in the 1990s? Med Hypotheses. 2007;69(3):652-9.

Borlongan. Recent preclinical evidence advancing cell therapy for Alzheimer's disease. Exp Neurol. Sep. 2012;237(1):142-6. doi: 10.1016/j.expneurol.2012.06.024. Epub Jun. 27, 2012.

Borowitz et al., Study of a novel pancreatic enzyme replacement therapy in pancreatic insufficient subjects with cystic fibrosis J.Pediatr., 149:658-662 (2006).

Borowitz, et al. Use of pancreatic enzyme supplements for patients with cystic fibrosis in the context of fibrosing colonopathy. Consensus Committee. J Pediatr. Nov. 1995;127(5):681-4.

Bouhnik, et al. Lactulose ingestion increases faecal bifidobacterial counts: A randomized double-blind study in healthy humans. European Journal of Clinical Nutrition 58:462-466 (2004).

Bowen. Exocrine secretions of the pancreas. Jul. 5, 2006. Accessed online at www.vivo.colostate.edu/hbooks/pathphys/digestion/pancreas/exocrine.html.

Boyd, et al. Positively charged amino acid residues can act as topogenic determinants in membrane proteins. Proc Natl Acad Sci U S A. Dec. 1989;86(23):9446-50.

Bradstreet, et al. Detection of Measles Virus Genomic RNA in Cerebrospinal Fluid of Children with Regressive Autism: a Report of Three Cases. J. Am Phys Surg. 2004; 9(2):38-45.

Bray, et al. Effect of dietary protein content on weight gain, energy expenditure, and body composition during overeating. A randomized controlled trial. JAMA. Jan. 4, 2012; 307(1):47-55.

Brinkley, et al. Factor analysis of the aberrant behavior checklist in individuals with autism spectrum disorders. J Autism Dev Disord. Nov. 2007;37(10):1949-59. Epub Dec. 21, 2006.

Brown. Background to Parkinson's Disease. biomed.brown.edu. Jul. 14, 2008.

Brudnak et al. Enzyme-based therapy for autism spectrum disorders—is it worth another look? Med Hypoth. 2002; 58:422-428.

Brudnak, Mark et al., Guide to intestinal health in autism spectrum disorder, Kirkman Laboratories, (Oct. 2001).

Bruhat, et al. Amino acid limitation induces expression of CHOP, a CCAAT/enhancer binding protein-related gene, at both transcriptional and post-transcriptional levels. J Biol Chem. Jul. 11, 1997;272(28):17588-93.

Buie, et al. Evaluation, diagnosis, and treatment of gastrointestinal disorders in individuals with ASDs: a consensus report. Pediatrics. Jan. 2010;125 Suppl 1:S1-18.

Button, KS et al. Power failure: why small sample size undermines the reliability of neuroscience. Nat. Rev. Neurosci. 14:365376 (2013).

Calderon-Garciduenas, et al. Immunotoxicity and environment: immunodysregulation and systemic inflammation in children. Toxicol Pathol. 2009;37(2):161-9.

Caldwell, et al. Crystalline Pancreatic Amylase. II. Improved Method for its Preparation from Hog Pancreas Glands and Additional Studies of its Properties. J. Am. Chem. Soc. 1952; 74(16):4033-4035.

Campbell et al. A genetic variant that disrupts MET transcription is associated with autism. Proc Natl Acad Sci USA. 2006; 103(45):16834-16839.

Campbell, et al. Distinct genetic risk based on association of MET in families with co-occurring autism and gastrointestinal conditions. Pediatrics. Mar. 2009;123(3):1018-24.

(56) References Cited

OTHER PUBLICATIONS

Carlton. Autism and malnutrition: the milk connection. Retrieved from the internet on Feb. 18, 2008, http://www.mercola.com/2004/autism_malnutrition.htm.
Caronna, et al. Autism spectrum disorders: clinical and research frontiers. Arch Dis Child. Jun. 2008;93(6):518-23.
Carroccio et al. Effectiveness of Enteric-coated Preparations on Nutritional Parameters in Cystic Fibrosis. Digestion 41:201-206 (1988).
Carroccio, et al. Pancreatic enzyme therapy in childhood celiac disease. A double-blind prospective randomized study. Dig Dis Sci. Dec. 1995;40(12):2555-60.
Carroccio, et al. Secondary impairment of pancreatic function as a cause of severe malabsorption in intestinal giardiasis: a case report. Am J Trop Med Hyg. Jun. 1997;56(6):599-602.
Carroccio, et al. Secretin-cerulein test and fecal chymotrypsin concentration in children with intestinal giardiasis. Int J Pancreatol. Oct. 1993;14(2):175-80.
Cassidy, et al. A new concept for the mechanism of action of chymotrypsin: the role of the low-barrier hydrogen bond. Biochemistry. Apr. 15, 1997;36(15):4576-84.
CDC, *Escherichia coli*, Travelers Health, Chapter 3: Infectious Diseases Related to Travel, Jul. 10, 2015, Available Online at: wwwnc.cdc.gov/travel/yellowbook/2016/infectious-diseases-related-to-travel/escherichia-coli.
CDC. Attention-Deficit/Hyperactivity Disorder (ADHD). Www.cdc.org. 2005.
CDC. Autism Information Center/FAQs. Dept of Health and Human Services/CDC. Jan. 30, 2008.
CDC. High Blood Pressure. Division for Heart Disease Stroke Prevention. Jul. 15, 2003.
Chaignon et al. Susceptibility of staphylococcal biofilms to enzymatic treatments depends on their chemical compositions. Appl. Microbiol. Appl. Microbiol. 75:125-132 (2007).
Chazalette, J.P. et al., A double-bind placebo-controlled trial of a pancreatic enzyme formulation (Panzytrat 25000) in the treatment of impaired lipid digestion in patients with cystic fibrosis. Drug Invest., 5(5):274-280 (1993).
Chen, et al. Identification of two lysosomal membrane glycoproteins. J Cell Biol. Jul. 1985;101(1):85-95.
Chen, et al. Lysine 43 is trimethylated in subunit C from bovine mitochondrial ATP synthase and in storage bodies associated with batten disease. J Biol Chem. May 21, 2004;279(21):21883-7.
Chen, et al. Medicinal Functions of Bromelain and Its Application Prospect in Animal Husbandry, China Animal Husbandry & Veterinary Medicine. 2005; vol. 32, No. 1, p. 14-16. (in Chinese with English translation).
Chen, Li et al. Antibiotic effect of lysostaphin on granulation wound. Acta Academiae Medicinae Militaris Tertiae, 8(14) p. 1 Abstract (2006).
Chez, M. et al. Secretin and autism: A two-part clinical investigation. Journal of Autism and Developmental Disorders, 30(2), 87-94 (Apr. 2000) [Abstract Only].
Childhood Autism Rating Scale (CARS), Wikipedia, downloaded May 5, 2014.
Chung, et al. Effects of a central cholinesterase inhibitor on reducing falls in Parkinson disease. Neurology. Oct. 5, 2010;75(14):1263-9. Epub Sep. 1, 2010.
Cichoke, AJ The Complete Book of Enzyme Therapy, Penguin (1999) pp. 206-208 and 38.
Cichoke, et al. The complete book of enzyme therapy. Penguin. 1998: 39, 42, 47, 50, and 53.
Cichoke. Celiac disease. The complete book of enzyme therapy. Penguin. New York, NY. 1999; 174-177.
Cichoke. Influenza. In: The Complete Book of Enzyme Therapy. D. Stewart, ed. Copyright 1999. Anthony J. Cichoke. Penquin Putnam, Inc., New York, New York. pp. "Contents", 50, 273-275 and 455.
Clark et al., The effect of ranitidine versus proton pump inhibitors on gastric secretions: a meta-analysis of randomized control trials, Anaesthesia, 2009, 64, pp. 652-657.

Claud, et a. Hypothesis: inappropriate colonization of the premature intestine can cause neonatal necrotizing enterocolitis. FASEB J. Jun. 2001;15(8):1398-403.
Commentary on the Japanese Pharmacopoeia, 14th ed., D929-D931, 2001.
Concerta. ADHD Myths and Facts. ADHD Myths and Facts about medication, girls, and symptoms and causes. Concerta.net. Jul. 15, 2008.
Cornish. A balanced approach towards healthy eating in autism, Journal of Human Nutrition and Dietetics 11:501-509 (1998).
Corring, et al. Development of digestive enzymes in the piglet from birth to 8 weeks. I. Pancreas and pancreatic enzymes. Nutr Metab. 1978;22(4):231-43.
Couet, et al. Identification of peptide and protein ligands for the caveolin-scaffolding domain. Implications for the interaction of caveolin with caveolae-associated proteins. J Biol Chem. Mar. 7, 1997;272(10):6525-33.
Coutinho, AM et al. Variants of the serotonin transporter gene (SLC6A4) significantly contribute to hyperserotonemia in autism. Mol Psychiatry. Mar. 2004;9(3):264-71.
Cox, RJ et al. Influenza Virus: Immunity and Vaccination Strategies. Comparison of the Immune Response to Inactivated and Live, Attenuated Influenza Vaccines. Scandinavian Journal of Immunology 59, 1-15 (2004).
Coyle. Treating the Negative Symptoms of Schizophrenia: An Expert Interview with Joseph Coyle, MD. www.narsad.org/?q=node/438/latest-research. 2006.
Craig, et al. Heat shock proteins: molecular chaperones of protein biogenesis. Microbiol Rev. Jun. 1993;57(2):402-14.
Creon—FDA Prescribing information side effects and uses. Revised Apr. 2015.
Creon digestive enzymes. Celic.com/ Jun. 2009. http://www.celiac.com/gluten-free/topic/59195-creon-digestive-enzymes.
Creon. Full prescribing information. Last edited Mar. 2013. Abbvie Inc 2012. www.rxabbvie.com/pdf/creon_PI.pdf.
Croonenberghs, et al. Peripheral markers of serotonergic and noradrenergic function in post-pubertal, caucasian males with autistic disorder. Neuropsychopharmacology. Mar. 2000;22(3):275-83.
Cruse et al. Illustrated dictionary of immunology. CRC Press, New York. 1995.
Cuervo, et al. Cathepsin A regulates chaperone-mediated autophagy through cleavage of the lysosomal receptor. EMBO J. Jan. 2, 2003;22(1):47-59.
Curemark press release. Curemark Receives Investigational New Drug Clearance for CM-AT for Autism. Mar. 26, 2009. http://www.medicalnewstoday.com/releases/143723.php.
Curemark Trademark/Service mark application, Principal Register. Serial No. 77527223. Filing date: Jul. 21, 2008.
Dajcs, et al. Lysostaphin is effective in treating methicillin-resistant *Staphylococcus aureus* Endophthalmitis in the rabbit. Curr Eye Res. Jun. 2001;22(6):451-7.
Daly, E., et al. Response inhibition and serotonin in autism: A functional MRI study using acute tryptophan depletion. Brain, 137(9), 2600-2610 (Sep. 2014).
Darman. An introduction to alternative medicine for psychiatric conditions. Oct. 22, 2007, retrieved on Sep. 18, 2009, http://web.archive.org/web/20071022104238/http://altp[therapies4bipolar.info/ortho/html.
Dawe, et al. Antipsychotic drugs dose-dependently suppress the spontaneous hyperactivity of the chakragati mouse. Neuroscience. Nov. 24, 2010;171(1):162-72. Epub Sep. 17, 2010.
Dawe, et al. The chakragati mouse: a mouse model for rapid in vivo screening of antipsychotic drug candidates. Biotechnol J. Nov. 2007;2(11):1344-52.
Dawn. Autism: the Latest Prevalence Rates in USA—Now 1 in 175. Disabled Women's Network Ontario. Dawn.thot.net/autism2.html. 2006.
Dawson lab. Research Projects in Synthetic Protein Chemistry. 2005; 1-2.
Delong. News on Parkinson's. The Dana Foundation. Jul. 14, 2008.
DeMasi, Carl B. The Role of Enzymatic Detergents in Washing Medical Devices and Removing Contaminants from Them, National Diet 73:28-35 (May 2002).

(56) References Cited

OTHER PUBLICATIONS

Derwent. English abstract for RU 2286785 Nov. 10, 2006. Downloaded from the Derwent file Jul. 13, 2011.
Diagnostic and Statistical Manual of Mental Disorders, Fourth Edition, Primary Care Version, Chapter 6, American Psychiatric Association (2000).
Diagnostic and Statistical Manual of Mental Disorders, Fourth Edition, Text Revision, DSM-IV-TR, American Psychiatric Association (2000).
Diaz-Hernandez, et al. Neuronal induction of the immunoproteasome in Huntington's disease. J Neurosci. Dec. 17, 2003;23(37):11653-61.
Digestive Enzyme Preparation: Pancreatin listed in Japanese Pharmacopoeia, Aug. 2008, <URL:http: > (in Japanese with English translation) < /URL:http: >.
Digestive Enzyme Wikipedia. Retrieved from the internet Sep. 10, 2009, http://en.wikipedia.org/wiki/Digestive_enzyme.
Ding, et al. Proteasome inhibition in oxidative stress neurotoxicity: implications for heat shock proteins. J Neurochem. May 2001;77(4):1010-7.
Dobbs et al. Link between helicobacter pylori infection and idiopathic parkinsonism. Medical Hypothesis. 2000; 55(2):93-98.
Dockter et al. Determination of chymotrypsin in the feces by a new photometric method. Padiatr Padol. 1985; 20(3):257-265.
Dominquez-Munoz, et al. Optimising the therapy of exocrine pancreatic insufficiency by the association of a proton pump inhibitor to enteric coated pancreatic extracts. Gut. Jul. 2006;55(7):1056-7.
Drabkin, H., et al. Initiation of protein synthesis in mammalian cells with codons other than AUG and amino acids other than methionine. Molecular and Cellular Biology, 18(9): 5140-5147 (Sep. 1998).
Dupiereux, et al. Creutzfeldt-Jakob, Parkinson, lewy body dementia and Alzheimer diseases: from diagnosis to therapy. Cent Nerv Syst Agents Med Chem. Mar. 2009;9(1):2-11.
Durkin, et al. Socioeconomic inequality in the prevalence of autism spectrum disorder: evidence from a U.S. cross-sectional study. PLoS One. Jul. 12, 2010;5(7):e11551.
Eaves, et al. The criterion-related validity of the Childhood Autism Rating Scale and the Autism Behavior Checklist. J Abnorm Child Psychol. Oct. 1993;21(5):481-91. abstract only.
Edelson, et al. 3-Cyclohexene-1-glycine, an Isoleucine Antagonist. J. Am. Chem. Soc. 1958; 80(11):2698-2700.
Elkashef, et al. Biological markers of cocaine addiction: implications for medications development. Addict Biol. Jun. 2003;8(2):123-39.
Elphick, et al. Impaired luminal processing of human defensin-5 in Crohn's disease: persistence in a complex with chymotrypsinogen and trypsin. Am J Pathol. Mar. 2008;172(3):702-13.
Emc, Creon 10000 Capsules, May 18, 2015, Available Online at: www.medicines.org.uk/emc/medicine/2068.
eMedExpert, Antibiotics: Cephalosporins, Available online at: http://www.emedexpert.com/compare/ cephalosporins.shtml, available as early as Jun. 2, 2007 per Internet Archive Wayback Machine.
Ethridge, et al. Acute pancreatitis results in induction of heat shock proteins 70 and 27 and heat shock factor-1. Pancreas. Oct. 2000;21(3):248-56.
Evans, C. et al. Altered amino acid excretion in children with autism. Nutritional Neuroscience, 11(1):9-17 (Feb. 2008).
Evans, et al. Pancreatic insufficiency in adult celiac disease: do patients require long-term enzyme supplementation? Dig Dis Sci. Oct. 2010;55(10):2999-3004. doi: 10.1007/s10620-010-1261-y. Epub May 11, 2010.
Exocrine Pancreatic Insufficiency (Enzymes) Document downloaded online on Jan. 8, 2016 at: http://www.epi4dogs.com/enzyme.htm.
Fafournoux, P. et al. Amino acid regulation of gene expression. Biochemical Journal, 351:1-12(2000).
Fairclough, P. et al. Comparison of the absorption of two protein hydrolysates and their effects on water and electrolyte movements in the human jejunum. Gut, 21(10):829-834 (1980).
Fallingborg, et al. Measurement of gastrointestinal pH and regional transit times in normal children. J Pediatr Gastroenterol Nutr. Aug. 1990;11(2):211-4.
Fallon, Joan. The Role of Amino Acids in Neurodegenerative and Addictive Diseases. Optogenetics: From Neuronal Function to Mapping and Disease Biology (2017) 453-462.
Fallon. Could one of the most widely prescribed antibiotics amoxicillin/clavulanate "augmentin" be a risk factor for autism? Med Hypotheses. 2005;64(2):312-5.
Family Caregiver Alliance. Fact Sheet: Parkinson's Disease. Caregiver.org. Jul. 14, 2008.
Felig, P. Amino acid metabolism in man. Annual Review of Biochemistry, 44(1):933-955 (1975). [Abstract Only].
Fernell, et al. No evidence for a clear link between active intestinal inflammation and autism based on analyses of faecal calprotectin and rectal nitric oxide. Acta Paediatr. Jul. 2007;96(7):1076-9.
Ferrone, et al. Pancreatic enzyme pharmacotherapy. Pharmacotherapy. 2007; 27:910-920.
Fido, et al. Olanzapine in the treatment of behavioral problems associated with autism: an open-label trial in Kuwait. Med Princ Pract. 2008;17(5):415-8. doi: 10.1159/000141508. Epub Aug. 6, 2008.
Filipek et al. The screening and diagnosis of autistic spectrum disorders. J. of Autism and Dev Disorders. 1999; 29(6).
Final Office Action dated Jan. 3, 2012 for U.S. Appl. No. 10/681,018.
Final Office Action dated Jan. 26, 2012 for U.S. Appl. No. 12/487,864.
Final Office Action dated Nov. 8, 2011 for U.S. Appl. No. 12/054,343.
Final Office Action dated Nov. 8, 2011 for U.S. Appl. No. 12/786,739.
Final Office Action dated Nov. 9, 2010 for U.S. Appl. No. 09/990,909.
Final Office Action dated Feb. 14, 2011 for U.S. Appl. No. 12/049,613.
Final Office Action dated Feb. 27, 2009 for U.S. Appl. No. 11/555,697.
Final Office Action dated Mar. 13, 2009 for U.S. Appl. No. 11/232,180.
Final Office Action dated Mar. 17, 2008 for U.S. Appl. No. 10/681,018.
Final Office Action dated Apr. 28, 2009 for U.S. Appl. No. 10/681,018.
Final Office Action dated May 11, 2010 for U.S. Appl. No. 11/555,697.
Final Office Action dated Jun. 25, 2008 for U.S. Appl. No. 11/213,255.
Final Office Action dated Jul. 2, 2010 for U.S. Appl. No. 12/046,252.
Final Office Action dated Jul. 27, 2004 for U.S. Appl. No. 09/990,909.
Finegold et al. Gastrointestinal microflora studies in late-onset autism. Clinical Infectious Diseases. 2002; 35(1):S6-S15.
First, M. Structured clinical interview for DSM-IV-TR axis I disorders, research version, patient edition. (SCID-I/P) New York: Biometrics Research, New York State Psychiatric Institute. (2002).
Fitzsimmons, et al. High-dose pancreatic-enzyme supplements and fibrosing colonopathy in children with cystic fibrosis. N Engl J Med. May 1, 1997;336(18):1283-9.
Flament, M.P. et al. Development of 400 µm Pellets by Extrusion-Spheronization Application with Gelucire 50/02 to Produce a "Sprinkle" Form, Drug Development and industrial Pharmacy, 30:1, 43-51, DOI: 10.1081/DDC-120027510 (2004).
Fliri, et al. Drug effects viewed from a signal transduction network perspective. J Med Chem. Dec. 24, 2009;52(24):8038-46. doi: 10.1021/jm901001p.
Frossard, et al. Both thermal and non-thermal stress protect against caerulein induced pancreatitis and prevent trypsinogen activation in the pancreas. Gut. Jan. 2002;50(1):78-83.
Frossard. Trypsin activation peptide (TAP) in acute pancreatitis: from pathophysiology to clinical usefulness. JOP. Mar. 2001;2(2):69-77.
Furlano, et al. Colonic CD8 and gamma delta T-cell infiltration with epithelial damage in children with autism. J Pediatr. Mar. 2001;138(3):366-72.
Garcia et al. Detection of giardia lamblia, entamoeba histolytica/entamoeba dispar, and cryptosporidium parvum antigens in human fecal specimens using the triage parasite panel enzyme immunoassay. Am Soc for Microbiology. 2000; 38(9):3337-3340.
Gardner. Absorption of intact peptides: studies on transport of protein digests and dipeptides across rat small intestine in vitro. Q J Exp Physiol. Oct. 1982;67(4):629-37.
Garner Jr, et al. Porcine Pancreatic Lipase—A Glycoprotein. J Biol Chem. Jan. 25, 1972;247(2):561-5.

(56) References Cited

OTHER PUBLICATIONS

Gass, et al. Enhancement of dietary protein digestion by conjugated bile acids. Gastroenterology. Jul. 2007;133(1):16-23.
Generation Rescue. Autism and Vaccines Around the World: Vaccine Schedules, Autism Rates, and Under 5 Mortality. Apr. 1, 2009.
German, et al., Apple iPhone Review: Apple iPhone, Jun. 30, 2007; CINET.
Giglio, et al. Failure to thrive: the earliest feature of cystic fibrosis in infants diagnosed by neonatal screening. Acta Paediatr. Nov. 1997;86(11):1162-5.
Girella, E. et al. The assay of chymotrypsin in stool as a simple and effective test of exocrine pancreatic activity in cystic fibrosis. Pancreas, 3(3):254-262 (1988).
GM Chemie 2010 "Products: Hypromellose Phthalate" accessed from www.gmchemie.com on Sep. 22, 2014.
Goff, et al. Production of abnormal proteins in *E. coli* stimulates transcription of Ion and other heat shock genes. Cell. Jun. 1985;41(2):587-95.
Gonzalez, et al. Endoscopical, histological and immunological characteristics of the digestive mucosa in autistic children with gastrointestinal symptoms. 2005; 1-7.
Green, et al. Amino-terminal polymorphisms of the human beta 2-adrenergic receptor impart distinct agonist-promoted regulatory properties. Biochemistry. Aug. 16, 1994;33(32):9414-9.
Guesnet, P. et al. Docosahexaenoic acid (DHA) and the developing central nervous system (CNS)—Implications for dietary recommendations. Biochimie, 93(1):7-12(2011). [Abstract Only].
Gupta, et al. Analysis of data gaps pertaining to enterotoxigenic *Escherichia coli* in low and medium human development index countries, 1984-2005. Epidemiol Infect. 2008; 136:721-738.
Gupta, et al. Th1- and Th2-like cytokines in CD4+ and CD8+ T cells in autism. J Neuroimmunol. May 1, 1998;85(1):106-9.
Hadjivassiliou, et al. Does cryptic gluten sensitivity play a part in neurological illness? Lancet. Feb. 10, 1996;347(8998):369-71.
Hamel, E. et al. Effects of Cocaine on Rat Pancreatic Enzyme Secretion and Protein Synthesis, Digestive Diseases, 23(3):264-268 (Mar. 1978).
Happe et al. The neuropsychology of autism. Brain. 1996; 119:1377-1400.
Happe et al. Time to give up on a simple explanation for autism. Nat Neurosci. Oct. 2006; 9(10):1218-20.
Health.com. Who is affected by Parkinson's disease. www.health.com. Jul. 14, 2008.
Heijerman, et al. Omeprazole enhances the efficacy of pancreatin (pancrease) in cystic fibrosis. Ann Intern Med. Feb. 1, 1991;114(3):200-1.
Heil, M., et al. Low endogenous fecal chymotrypsin: a possible biomarker for autism. Poster presented at the annual IMFAR Conference on Autism, Atlanta, GA.(May 2014) p. 1.
Hendren et al. Mechanistic biomarkers for autism treatment. Medical Hypotheses. 2009; 73:950-954.
HITTI. Allergy, celiac disease, and ileal lymphonodular. WebMD. 2005. 1-2.
Holquist et al. FDA safety page: Delayed-release vs. extended release Rxs. Drug Topics [online] Jul. 23, 2007 [Retrieved on Jul. 30, 2012] Retrieved from the internet: http://drugtopics.modernmedicine.com/drugtopics/Top+News/FDA-safety-page-Delayed-release-vs-extended-release/ArticleStandard/Article/detail/442606.
Holten, et al. Appropriate prescribing of oral beta-lactam antibiotics. Am Fam Physician. Aug. 1, 2000;62(3):611-20.
Horvath et al. Improved social and language skills after secretin administration in patients with autistic spectrum disorders. Journal of the Association for Academic Minority Physicians. Jan. 1998; 9(1):9-15.
Horvath, et al. Autism and gastrointestinal symptoms. Curr Gastroenterol Rep. Jun. 2002;4(3):251-8.
Horvath, et al. Autistic disorder and gastrointestinal disease. Curr Opin Pediatr. Oct. 2002;14(5):583-7.
Horvath, et al. Gastrointestinal abnormalities in children with autistic disorder. J Pediatr. Nov. 1999;135(5):559-63.
Hoshiko et al. The effect of the gastrointestinal hormones on colonic muscosal blood flow. Acta Medica Nagasakiensia. 1994; 39(4):125-130.
Houston. Autism—One Conference. May 2006. 1-83.
Hsiao, et al. The microbes of the intestine: an introduction to their metabolic and signaling capabilities. Endocrinol Metab Clin North Am. Dec. 2008;37(4):857-71.
Huang, et al. Apoptotic cell death in mouse models of GM2 gangliosidosis and observations on human Tay-Sachs and Sandhoff diseases. Hum Mol Genet. Oct. 1997;6(11):1879-85.
Huang, et al. Mapping of the human APOB gene to chromosome 2p and demonstration of a two-allele restriction fragment length polymorphism. Proc Natl Acad Sci U S A. Feb. 1986;83(3):644-8.
Ijuin, H. Evaluation of pancreatic exocrine function and zinc absorption in alcoholism. The Kurume Medical Journal 45.1 (1998): 1-5.
Information of Papain from Worthington Enzymes webpage http://www.worthington-biochem.com/pap/default.html Downloaded Jan. 17, 2013.
International Application No. PCT/US18/26841 International Search Report and Written Opinion dated Jul. 3, 2018.
International preliminary report on patentability dated Jul. 17, 2014 for PCT/US2013/020183.
International search report and written opinion dated Feb. 21, 2013 for PCT/US2013/020183.
International search report and written opinion dated May 9, 2013 for PCT/US2013/024453.
International search report and written opinion dated Aug. 27, 2013 for PCT/US2013/043444.
International search report and written opinion dated Jan. 18, 2011 for PCT/US2010/057341.
International search report and written opinion dated Nov. 12, 2012 for PCT/US2012/034489.
International search report and written opinion dated Feb. 15, 2011 for PCT/US2010/053484.
International search report and written opinion dated Mar. 2, 2010 for PCT/US2010/020253.
International search report and written opinion dated Mar. 5, 2010 for PCT/US2010/020259.
International search report and written opinion dated Jun. 9, 2010 for PCT/US2010/030895.
International search report and written opinion dated Sep. 25, 2009 for PCT/US2009/049374.
International search report dated Mar. 11, 2002 for PCT/US2001/25343.
International search report dated Jun. 29, 2001 for PCT/US2000/34000.
Isaksson, et al. Pain reduction by an oral pancreatic enzyme preparation in chronic pancreatitis. Digestive Dis. Sci. 1983; 28(2):97-102.
James, et al. Thimerosal neurotoxicity is associated with glutathione depletion: protection with glutathione precursors. Neurotoxicology. 2004; 26(1):1-8.
Jeffrey. Global burden of hypertension may reach 1.5 billion by 2025. Medscape Medical News. Jul. 14, 2008.
Jenkins, et al. Management of gastroenteritis. Archives of Disease in Childhood. 1990; 65:939-941.
Johnson et al. Eating Habits and Dietary Status in Young Children with Autism. J Dev Phys Disabil 20:437-448 (2008).
Juhl. Fibromyalgia and the serotonin pathway. Altern Med Rev. 1998; 3(5):367-375.
Jyonouchi, et al. Dysregulated innate immune responses in young children with autism spectrum disorders: their relationship to gastrointestinal symptoms and dietary intervention. Neuropsychobiology. 2005;51(2):77-85.
Jyonouchi, et al. Evaluation of an association between gastrointestinal symptoms and cytokine production against common dietary proteins in children with autism spectrum disorders. J Pediatr. May 2005;146(5):605-10.
Jyonouchi, et al. Proinflammatory and regulatory cytokine production associated with innate and adaptive immune responses in children with autism spectrum disorders and developmental regression. J Neuroimmunol. Nov. 1, 2001;120(1-2):170-9.

(56) References Cited

OTHER PUBLICATIONS

Kachrimanis, et al. Tensile strength and disintegration of tableted silicified microcrystalline cellulose: influences of interparticle bonding. J Pharm Sci. Jul. 2003;92(7):1489-501.

Kaemmerer, et al. Effects of lipid peroxidation-related protein modifications on RPE lysosomal functions and POS phagocytosis. Invest Ophthalmol Vis Sci. Mar. 2007;48(3):1342-7.

Kaminski, et al. Polymorphism of bovine beta-casein and its potential effect on human health. J Appl Genet. 2007;48(3):189-98.

Kaspar et al. New photometric assay for chymotrypsin in stool. Clinical Chemistry. 1984; 30(11):1753-1757.

Katritos. New finding may have implications for schizophrenia, autism. Autism/Schizophrenia findings relating to protein, etc. Feb. 10, 2011. e-mail.

Kearney, et al. Global burden of hypertension: analysis of worldwide data. Lancet. Jan. 15-21, 2005;365(9455):217-23. Abstract only.

Keeley et al., Gradual vs. abrupt withdrawal of methylphenidate in two older dependent males. Journal of Substance Abuse Treatment. 2(2):123-125 (1985).

Keller, et al. Pancreatic enzyme supplementation therapy. Current Treatment Options in Gastroenterology 6.5 (2003): 369-374.

Kidd, P.M., Autism, an extreme challenge to integrative medicine. Part 2: medical management. Altern. Med. Rev., 7(6):172-499 (Dec. 2002).

King, et al. Effects of bacterial microflora of the lower digestive tract of free-range waterfowl on influenza virus activation. Appl Environ Microbiol. Jun. 2011;77(12):4119-25. doi: 10.1128/AEM.02578-10. Epub Apr. 29, 2011.

Knivsberg, et al. A randomised, controlled study of dietary intervention in autistic syndromes. Nutr Neurosci. Sep. 2002;5(4):251-61.
Koivu et al. Determination of Phylloquinone in Vegetables, Fruits, and Berries by High-Performance Liquid Chromatography with Electrochemical Detection. J. Agric. Food Chem. 45(12):4644-4649 (1997).
Kokai-Kun, et al. Lysostaphin as a treatment for systemic *Staphylococcus aureus* infection in a mouse model. J Antimicrob Chemother. Nov. 2007;60(5):1051-9. Epub Sep. 10, 2007.
Koller, et al. Falls and Parkinson's Disease (Abstract). Clin Neuropharmacol. 1989; 12(2):98-105.
Koplin, et al. Soy consumption is not a risk factor for peanut sensitization. J Allergy Clin Immunol. Jun. 2008;121(6):1455-9.
Koster et al. Evidence based medicine and extradigestive manifestations of helicobacter pylori. Acta Gastro-Enterologica Belgica. 2000; 63(4):388-392.
Krishnaswami, et al. A systematic review of secretin for children with autism spectrum disorders. Pediatrics. May 2011;127(5):e1322-5. doi: 10.1542/peds.2011-0428. Epub Apr. 4, 2011.
Kronenberg, et al. Folate deficiency induces neurodegeneration and brain dysfunction in mice lacking uracil DNA glycosylase. J Neurosci. Jul. 9, 2008;28(28):7219-30.
Kujoth, et al. Mitochondrial DNA mutations, oxidative stress, and apoptosis in mammalian aging. Science. Jul. 15, 2005;309(5733):481-4.
Kumar. Neurologic presentations of nutritional deficiencies. Neurol Clin. Feb. 2010;28(1):107-70.
Larimore. How Common Is ADHD? Facts About ADHD. Jul. 15, 2008.
Lashkari, et al. Williams-Beuren Syndrome: An update and review for the primary physician. Clinical Pediatrics. 1999; 38(4):189-208.
Layer et al. Pancreatic enzyme replacement therapy. Current Gastroenterology Reports. 2001; 3:101-108.
Lebenthal, et al. Enzyme therapy for pancreatic insufficiency: present status and future needs. Pancreas. Jan. 1994;9(1):1-12.
Leeds, et al. Is exocrine pancreatic insufficiency in adult coeliac disease a cause of persisting symptoms? Aliment Pharmacol Ther. Feb. 1, 2007;25(3):265-71.
Levy, et al. Relationship of dietary intake to gastrointestinal symptoms in children with autistic spectrum disorders. Biol Psychiatry. Feb. 15, 2007;61(4):492-7.
Leyfer, et al. Comorbid psychiatric disorders in children with autism: interview development and rates of disorders. J Autism Dev Disord. Oct. 2006;36(7):849-61.
Lieberman. Pharmaceutical Dosage Forms. vol. 2: Disperse Systems. New York Marcel Dekker, Inc. 1996; 243-258.
Life Plus Somazyne accessed Jun. 10, 2016, Online at www.lifeplus.com/media/pdf/piSheets/US/ 6141-PI_EN.pdf.
Lindsay, et al. Dietary status and impact of risperidone on nutritional balance in children with autism: A pilot study. Journal of Intellectual & Developmental Disability, 31(4): 204-209 (2006).
Lipase 30, Technical Data sheet, 1 page, Scientific Protein Laboratories LLC Jun. 13, 2005.
Liyanage, et al. Bioavailability of iron from micro-encapsulated iron sprinkle supplement. Food and Nutrition bulletin. 2002; 23(3):133-137.
Lloyd. Lysosome membrane permeability: implications for drug delivery. Adv Drug Deliv Rev. Mar. 30, 2000;41(2):189-200.
Loh, et al. Highly tolerated amino acid substitutions increase the fidelity of *Escherichia coli* DNA polymerase I. J Biol Chem. Apr. 20, 2007;282(16):12201-9.
Lord, et al. Diagnostic Instruments in Autistic Spectrum Disorders. info.med.yale.edu. 2005; 11:730-771.
Luedtke, et al. Cathepsin A is expressed in a cell- and region-specific manner in the testis and epididymis and is not regulated by testicular or pituitary factors. J Histochem Cytochem. Aug. 2000;48(8):1131-46.
Macdonald. Thyrotoxicosis treated with pancreatic extract and iodine. Lancet. 1943; 244(6251):788.
Macfabe, et al. Neurobiological effects of intraventricular propionic acid in rats: possible role of short chain fatty acids on the pathogenesis and characteristics of autism spectrum disorders. Behav Brain Res. 2006;176(1):149-69.
Macready. Parkinson's Disease Treatment: what you should know. Retrieved from the internet on Sep. 15, 2009, http://www.everydayhealth.com/parkinsons-disease-treatment-overview.aspx.
Mannino, et al. Surveillance for asthma—United States, 1960-1995. MMWR CDC Surveill Summ. Apr. 24, 1998;47(1):1-27.
Marcus, et al. A placebo-controlled, fixed-dose study of aripiprazole in children and adolescents with irritability associated with autistic disorder. J Am Acad Child Adolesc Psychiatry. Nov. 2009;48(11):1110-19.
Marczewska et al. Protein intake in parkinsonian using the EPIC food frequency questionnaire. Mov Diord. Aug. 2006; 21(8):1229-1231.
Marion et al., A New Procedure Allowing the Complete Removal and Prevention of Hemodialysis. Blood Purification, 23:339-348 (2005).
Marlicz et al. Determination of chymotrypsin in the stool in the diagnosis of chronic pancreatitis. Wiadomosci lekarskie. 1988; 41(11):704-707. (in Polish with English abstract/summary).
Marsh. Neuropsychiatric aspects of Parkinson's disease. Psychosomatics. 2000; 41(1):15-23.
Martin, et al. A rapid and sensitive spectrophotometric method for the assay of chymotrypsin. Biol Chem. Feb. 1959;234(2):294-8.
Matikainen, et al. Autonomic dysfunction in long-standing alcoholism. Alcohol. 1986;21(1):69-73. Abstract only.
Matthews, D. Intestinal absorption of amino acids and peptides. Proceedings of the Nutrition Society, 31(2):171-177(1972).
Maurin, et al. Cellular adaptation to amino acid availability: mechanisms involved in the regulation of gene expression. 2006; 319-326.
Mayo Clinic Staff. Autism. Retrieved from internet Mar. 10, 2008, http://www.mayoclinic.com/health/autism/DS00348DSECTION=2.
Mayo Clinic Staff. Bipolar disorder. Jan. 4, 2008, http://www.mayoclinic.com/health/bipolardisorder/DS00356/DSECTION=symptoms.
Mayo Clinic Staff. Obsessive-compulsive disorder. Dec. 21, 2006. http://www.preferredalternatives.org/lat/WellnessLibrary/anxiety&PanicDisorders/Obsessive-CompulsiveDisorder/Obsessive-CompulsiveDisorder-Mayoclinic.pdf.

(56) References Cited

OTHER PUBLICATIONS

Mayo Clinic Staff. Oppositional defiant disorder. Dec. 19, 2007, http://www.mayoclinic.com/health/oppositional-defiant- disorder/DS00630/DSECTION=symptoms.
Mcalonan, et al. Brain anatomy and sensorimotor gating in Asperger's syndrome. ain. Jul. 2002;125(Pt 7):1594-606.
McClung, C., et al. Regulation of gene expression and cocaine reward by CREB and DeltaFosB. Nature Neuroscience, 6(11):1208-1215 (2003). [Abstract Only].
McClung, C.A. et al. DeltaFosB: A molecular switch for long-term adaptation in the brain. Molecular Brain Research, 132(2):146-154 (Dec. 20, 2004).
McCormack, et al. Localization of the disulfide bond involved in post-translational processing of glycosylasparaginase and disrupted by a mutation in the Finnish-type aspartylglycosaminuria. J Biol Chem. Feb. 17, 1995;270(7):3212-5.
McCracken, et al. Risperidone in children with autism and serious behavioral problems. N Engl J Med. Aug. 1, 2002;347(5):314-21.
Medori et al. Fatal Familial Insomnia, A Prion Disease With a Mutation at Condon 178 of the Prion Protein Case. N Engl J Med 326:444-449 (1992).
Medsafe. Data sheet for alpha-lactose, Jul. 21, 2008. http://www.medsafe.govt.nz/Profs/Datasheet/a/Alphalactulosesyrup.htm.
Medscape. Burden of Hypertension in the United States Greater Than Ever. www.medscape.com. Jul. 14, 2004.
Melmed, et al. Metabolic markers and gastrointestinal symptoms in children with autism and related disorders. J Pediatr Gast Nutr. 2000; 31:S31-S32. Abstract only.
Merck. Autism, Merck manual online medical library home addition, retrieved from the internet Mar. 10, 2008, http://www.mercl.com/mmhge/sec23/ch286/ch286b.html.
Merriam-Webster 2014 "Definition: Precipitate" accessed from www.mirriam-webster.com on Sep. 22, 2014.
MeSH browser. "Child Development Disorders, Pervasive," and "Attention Deficit and Disruptive Behavior Disorders," National Library of medicine. 2001, http://www.nlm.nih.gov/mesh/2002/Mbrowser.html.
Meyer-Lindenberg, et al. Neural mechanisms in Williams syndrome: a unique window to genetic influences on cognition and behavior. Nat. Rev. Neurosci. 2006; 7(5):380-93.
Michael's Naturopathic Programs, Digestive Enzymes, Product #011161, Accessed on Jun. 10, 2016, online at: www.michaelshealth.com/retail/digestive-enzymes-659.html.
Michell et al. Biomarkers and Parkinson's disease. Brain. 2004; 127(8):1693-1705.
Millipore EMD catalog (online). Papain, unit definition, EMD Millipore Corp, 2013. Downloaded May 13, 2013.
Minamino, et al. Vascular cell senescence: contribution to atherosclerosis. Circ Res. Jan. 5, 2007;100(1):15-26.
Ming, et al. Autism spectrum disorders: concurrent clinical disorders. J Child Neurol. Jan. 2008;23(1):6-13.
Mitchell, et al. Comparative trial of viokase, pancreatin and Pancrease pancrelipase (enteric coated beads) in the treatment of malabsorption in cystic fibrosis. Aust Paediatr J. Jun. 1982;18(2):114-7.
Mitsui, et al. Role of aminopeptidases in the blood pressure regulation. Biological and Pharmaceutical Bulletin of Japan, Pharmaceutical Society of Japan. 2004; 27(6):768-771.
Mizutani, et al. Effects of placental proteases on maternal and fetal blood pressure in normal pregnancy and preeclampsia. Am J Hypertens. Jun. 1996;9(6):591-7.
Mononen, et al. Aspartylglycosaminuria in the Finnish population: identification of two point mutations in the heavy chain of glycoasparaginase. Proc Natl Acad Sci U S A. Apr. 1, 1991;88(7):2941-5.
Moretti, et al. Acute pancreatitis: hypertonic saline increases heat shock proteins 70 and 90 and reduces neutrophil infiltration in lung injury. Pancreas. Jul. 2009;38(5):507-14. Abstract only.
Morimoto, R. The heat shock response: Systems biology of proteotoxic stress in aging and disease. Cold Spring Harbor Symposia on Quantitative Biology, 76:91-99 (2011) (Epub: Feb. 27, 2012).
Mosqueira, et al. Chronic hypoxia impairs muscle function in the Drosophila model of Duchenne's muscular dystrophy (DMD). PLoS One. Oct. 20, 2010;5(10):e13450.
Munasinghe et al. Digestive enzyme supplementation for autism spectrum disorders: a double-blind randomized controlled trial. J Autism Dev Disord. Sep. 2010;40(9):1131-8.
Munesue, et al. High prevalence of bipolar disorder comorbidity in adolescents and young adults with high-functioning autism spectrum disorder: a preliminary study of 44 outpatients. Journal of Affective Disorders 111.2-3 (2008): 170-175.
Nachaegari et al. Coprocessed excipients for solid dosage forms. Pharmaceutical Technology. 2004; p. 52, 54, 56 ,58, 60, 64.
Nagamoto. Jacobson: Psychiatric Secrets, 2nd ed. 2001. Ch 28 Antipsychotic meds.
Naushad, Shaik Mohammad et al. Autistic children exhibit distinct plasma amino acid profile. Indian Journal of Biochemistry and Biophysics, 50(5):474-478 (Oct. 2013).
Nestler, E. et al. DeltaFosB: A sustained molecular switch for addiction. Proceedings of the National Academy of Sciences, 98(20):11042-11046 (Sep. 25, 2001).
Nestler, E.J. Molecular basis of long-term plasticity underlying addiction. Nature Reviews Neuroscience, 2(2):119-128 (Feb. 2001).
Nestler, et al. Delta-FosB: A sustained molecular switch for addiction. PNAS 98(20): 11042-11046 (Sep. 25, 2001).
Neuer, et al. The role of heat shock proteins in reproduction. Hum Reprod Update. Mar.-Apr. 2000;6(2):149-59.
Neumeyer, Ann. M. et al. Brief Report: Bone Fractures in Children and Adults with Autism Spectrum Disorders. J. Autism Dev. Disord. 45(3):881-887 (Mar. 2016).
Nevo et al. Acute immune polyneuropathies: correlations of serum antibodies to campylobacter jejuni and helicobacter pylori with anti-gm antibodies and clinical patterns of disease. J of Inf diseases. 1997; 175(S2):S154-6.
Newhorizons. ADD/ADHD: New Perspectives on Attentional Priority Disorders. New Horizons for Learning. Jul. 15, 2008.
NIH, "Celiac Disease", National Digestive Diseases Information Clearinghouse: Bethesda, MD, 2008; 12 pages.
NIH. National Institutes of Health. National Diabetes Statistics 2007. diabetes.niddk.nih.gov. Jun. 1, 2008.
NINDS Guillain-Barre Syndrome Information Page, retrieved from the internet Sep. 15, 2009, http://www.ninds.nih.gov/disorders/gbs/gbs.htm.
NINDS Dysautonomia Information Page, retrieved from the internet Sep. 10, 2009, http://www.ninds.nih.gov/disorders/dysautonomia/dysautonomia.htm.
No Author. RSDSA, 2015: Telltale signs and symptoms of CRPS/RSD on the web at rsds.org/telltale-signs-and-symptoms-of-crpsrsd. [Accessed: Sep. 5, 2018].
Norton, L. et al. Leucine regulates translation initiation of protein synthesis in skeletal muscle after exercise. The Journal of Nutrition, 136(2):533S-537S (Feb. 2006).
Notice Non-Compliant Amendment dated Jun. 19, 2009 for U.S. Appl. No. 11/232,180.
Notice Non-responsive Amendment dated Sep. 22, 2008 for U.S. Appl. No. 11/232,180.
Notice of allowance dated Jan. 2, 2014 for U.S. Appl. No. 13/204,881.
Notice of allowance dated Feb. 2, 2015 for U.S. Appl. No. 13/926,822.
Notice of Allowance dated Feb. 17, 2012 for U.S. Appl. No. 10/681,018.
Notice of allowance dated Feb. 20, 2015 for U.S. Appl. No. 12/386,051.
Notice of allowance dated Feb. 27, 2015 for U.S. Appl. No. 14/037,696.
Notice of allowance dated Mar. 1, 2016 for U.S. Appl. No. 14/087,930.
Notice of Allowance dated Mar. 21, 2012 for U.S. Appl. No. 12/487,864.
Notice of allowance dated Apr. 3, 2015 for U.S. Appl. No. 13/737,225.
Notice of allowance dated Apr. 10, 2015 for U.S. Appl. No. 13/144,290.
Notice of allowance dated Apr. 14, 2015 for U.S. Appl. No. 13/144,286.
Notice of Allowance dated Apr. 15, 2011 for U.S. Appl. No. 12/487,868.

(56) References Cited

OTHER PUBLICATIONS

Notice of allowance dated Apr. 22, 2016 for U.S. Appl. No. 14/528,715.
Notice of Allowance dated Apr. 29, 2011 for U.S. Appl. No. 12/046,402.
Notice of Allowance dated May 23, 2011 for U.S. Appl. No. 09/990,909.
Notice of Allowance dated May 29, 2013 for U.S. Appl. No. 13/481,087.
Notice of allowance dated Jun. 12, 2014 for U.S. Appl. No. 13/448,061.
Notice of Allowance dated Jun. 27, 2011 for U.S. Appl. No. 12/238,415.
Notice of Allowance dated Jun. 28, 2011 for U.S. Appl. No. 12/487,868.
Notice of Allowance dated Jun. 30, 2011 for U.S. Appl. No. 09/990,909.
Notice of allowance dated Jul. 3, 2012 for U.S. Appl. No. 13/271,783.
Notice of Allowance dated Jul. 8, 2011 for U.S. Appl. No. 12/046,402.
Notice of Allowance dated Aug. 8, 2011 for U.S. Appl. No. 12/426,794.
Notice of allowance dated Aug. 11, 2014 for U.S. Appl. No. 13/193,346.
Notice of allowance dated Aug. 19, 2013 for U.S. Appl. No. 13/208,963.
Notice of allowance dated Aug. 30, 2013 for U.S. Appl. No. 12/047,818.
Notice of allowance dated Sep. 9, 2015 for U.S. Appl. No. 13/193,346.
Notice of allowance dated Sep. 15, 2014 for U.S. Appl. No. 14/037,652.
Notice of Allowance dated Sep. 20, 2011 for U.S. Appl. No. 12/283,090.
Notice of allowance dated Oct. 29, 2013 for U.S. Appl. No. 13/204,881.
Notice of allowance dated Nov. 16, 2015 for U.S. Appl. No. 14/493,734.
Notice of allowance dated Dec. 23, 2014 for U.S. Appl. No. 14/007,793.
Notice of allowance dated Dec. 23, 2015 for U.S. Appl. No. 12/493,122.
Notice of Non-Complaint Amendment dated Jun. 2, 2008 for U.S. Appl. No. 12/046,252.
Notice of Non-Compliant Amendment dated Apr. 27, 2010 for U.S. Appl. No. 12/283,090.
Notice of Non-Compliant Amendment dated Jul. 7, 2007 for U.S. Appl. No. 11/213,255.
Notice of Non-Responsive Amendment dated Feb. 11, 2008 for U.S. Appl. No. 11/555,697.
Notice of Non-Responsive Amendment dated Sep. 25, 2008 for U.S. Appl. No. 11/555,697.
O'Connell. Hypertension Guide. cmbi.bjmu.edu. Jul. 14, 2008.
Office action dated Jan. 12, 2012 for U.S. Appl. No. 12/047,818.
Office action dated Jan. 15, 2014 for U.S. Appl. No. 13/836,135.
Office action dated Jan. 15, 2016 for U.S. Appl. No. 13/502,989.
Office action dated Jan. 16, 2014 for U.S. Appl. No. 12/046,252.
Office action dated Jan. 16, 2015 for U.S. Appl. No. 12/535,676.
Office action dated Jan. 22, 2013 for U.S. Appl. No. 13/562,999.
Office action dated Jan. 24, 2014 for U.S. Appl. No. 12/054,343.
Office action dated Jan. 24, 2014 for U.S. Appl. No. 12/786,739.
Office action dated Jan. 25, 2013 for U.S. Appl. No. 13/208,963.
Office action dated Jan. 26, 2016 for U.S. Appl. No. 12/054,343.
Office action dated Jan. 29, 2016 for U.S. Appl. No. 12/786,739.
Office Action dated Feb. 1, 2012 for U.S. Appl. No. 12/493,122.
Office action dated Feb. 1, 2016 for U.S. Appl. No. 13/503,844.
Office action dated Feb. 14, 2013 for U.S. Appl. No. 13/193,346.
Office action dated Feb. 14, 2013 for U.S. Appl. No. 13/407,408.
Office action dated Feb. 17, 2016 for U.S. Appl. No. 14/713,178.
Office action dated Feb. 21, 2013 for U.S. Appl. No. 12/047,818.
Office action dated Feb. 26, 2016 for U.S. Appl. No. 12/535,676.
Office action dated Mar. 2, 2016 for U.S. Appl. No. 14/693,711.
Office Action dated Mar. 5, 2012 for U.S. Appl. No. 12/535,676.
Office action dated Mar. 5, 2013 for U.S. Appl. No. 12/493,122.
Office action dated Mar. 6, 2015 for U.S. Appl. No. 13/757,412.
Office action dated Mar. 11, 2014 for U.S. Appl. No. 11/533,818.
Office Action dated Mar. 19, 2012 for U.S. Appl. No. 13/204,881.
Office action dated Mar. 22, 2016 for U.S. Appl. No. 13/733,873.
Office Action dated Mar. 23, 2012 for U.S. Appl. No. 13/271,783.
Office Action dated Mar. 29, 2011 for U.S. Appl. No. 12/054,343.
Office Action dated Mar. 30, 2011 for U.S. Appl. No. 12/786,739.
Office action dated Mar. 30, 2016 for U.S. Appl. No. 14/296,091.
Office action dated Apr. 4, 2016 for U.S. Appl. No. 13/313,629.
Office Action dated Apr. 5, 2012 for U.S. Appl. No. 11/555,697.
Office action dated Apr. 5, 2016 for U.S. Appl. No. 14/713,242.
Office action dated Apr. 6, 2015 for U.S. Appl. No. 14/493,734.
Office action dated Apr. 6, 2016 for U.S. Appl. No. 13/313,708.
Office Action dated Apr. 9, 2012 for U.S. Appl. No. 13/208,963.
Office action dated Apr. 10, 2014 for U.S. Appl. No. 13/502,989.
Office action dated Apr. 16, 2014 for U.S. Appl. No. 13/705,763.
Office action dated Apr. 21, 2015 for U.S. Appl. No. 13/660,642.
Office action dated Apr. 21, 2015 for U.S. Appl. No. 14/087,930.
Office action dated Apr. 22, 2015 for U.S. Appl. No. 13/836,135.
Office action dated Apr. 24, 2015 for U.S. Appl. No. 12/786,739.
Office Action dated Apr. 27, 2011 for U.S. Appl. No. 10/681,018.
Office action dated Apr. 27, 2015 for U.S. Appl. No. 12/054,343.
Office Action dated Apr. 28, 2011 for U.S. Appl. No. 12/283,090.
Office action dated May 6, 2015 for U.S. Appl. No. 12/493,122.
Office action dated May 7, 2015 for U.S. Appl. No. 13/705,763.
Office action dated May 9, 2013 for U.S. Appl. No. 13/204,881.
Office action dated May 12, 2014 for U.S. Appl. No. 13/733,873.
Office action dated May 13, 2014 for U.S. Appl. No. 13/313,629.
Office action dated May 15, 2013 for U.S. Appl. No. 13/502,989.
Office action dated May 15, 2014 for U.S. Appl. No. 13/448,061.
Office action dated May 16, 2014 for U.S. Appl. No. 13/313,708.
Office Action dated May 24, 2011 for U.S. Appl. No. 12/487,864.
Office action dated May 27, 2015 for U.S. Appl. No. 13/502,989.
Office action dated Jun. 3, 2015 for U.S. Appl. No. 13/002,136.
Office action dated Jun. 13, 2012 for U.S. Appl. No. 12/493,122.
Office action dated Jun. 17, 2014 for U.S. Appl. No. 13/737,225.
Office action dated Jun. 17, 2014 for U.S. Appl. No. 13/757,412.
Office action dated Jun. 19, 2014 for U.S. Appl. No. 12/386,051.
Office action dated Jun. 25, 2013 for U.S. Appl. No. 13/144,286.
Office action dated Jun. 25, 2013 for U.S. Appl. No. 13/144,290.
Office action dated Jun. 27, 2012 for U.S. Appl. No. 12/493,147.
Office action dated Jun. 27, 2014 for U.S. Appl. No. 14/007,793.
Office action dated Jun. 29, 2011 for U.S. Appl. No. 11/555,697.
Office action dated Jul. 7, 2014 for U.S. Appl. No. 12/535,676.
Office action dated Jul. 11, 2012 for U.S. Appl. No. 12/573,353.
Office action dated Jul. 15, 2013 for U.S. Appl. No. 13/002,136.
Office action dated Jul. 17, 2015 for U.S. Appl. No. 13/733,873.
Office action dated Jul. 18, 2012 for U.S. Appl. No. 12/047,818.
Office action dated Jul. 31, 2013 for U.S. Appl. No. 13/757,412.
Office action dated Aug. 2, 2013 for U.S. Appl. No. 12/535,676.
Office action dated Aug. 7, 2014 for U.S. Appl. No. 13/836,135.
Office action dated Aug. 13, 2012 for U.S. Appl. No. 13/208,963.
Office action dated Aug. 14, 2013 for U.S. Appl. No. 13/448,061.
Office action dated Aug. 28, 2013 for U.S. Appl. No. 13/313,629.
Office action dated Aug. 29, 2014 for U.S. Appl. No. 13/144,286.
Office action dated Aug. 31, 2015 for U.S. Appl. No. 12/535,676.
Office action dated Sep. 8, 2015 for U.S. Appl. No. 11/533,818.
Office action dated Sep. 9, 2013 for U.S. Appl. No. 13/502,989.
Office action dated Sep. 10, 2015 for U.S. Appl. No. 13/313,629.
Office action dated Sep. 11, 2015 for U.S. Appl. No. 13/313,708.
Office action dated Sep. 13, 2012 for U.S. Appl. No. 13/481,087.
Office action dated Sep. 18, 2014 for U.S. Appl. No. 13/502,989.
Office action dated Sep. 19, 2014 for U.S. Appl. No. 11/533,818.
Office action dated Sep. 19, 2014 for U.S. Appl. No. 13/737,225.
Office action dated Sep. 30, 2014 for U.S. Appl. No. 13/144,290.
Office action dated Sep. 30, 2014 for U.S. Appl. No. 13/660,642.
Office Action dated Jan. 21, 2011 for U.S. Appl. No. 12/386,051.
Office Action dated Jan. 29, 2002 for U.S. Appl. No. 09/707,395.
Office Action dated Jan. 8, 2010 for U.S. Appl. No. 10/681,018.
Office action dated Oct. 2, 2014 for U.S. Appl. No. 12/054,343.
Office action dated Oct. 6, 2014 for U.S. Appl. No. 12/493,122.

(56) References Cited

OTHER PUBLICATIONS

Office action dated Oct. 9, 2014 for U.S. Appl. No. 12/786,739.
Office Action dated Oct. 1, 2001 for U.S. Appl. No. 09/466,559.
Office action dated Oct. 10, 2012 for U.S. Appl. No. 13/204,881.
Office action dated Oct. 19, 2011 for U.S. Appl. No. 12/386,051.
Office action dated Oct. 24, 2013 for U.S. Appl. No. 13/313,708.
Office action dated Oct. 25, 2012 for U.S. Appl. No. 13/144,286.
Office action dated Oct. 25, 2012 for U.S. Appl. No. 13/144,290.
Office action dated Oct. 30, 2015 for U.S. Appl. No. 14/528,715.
Office Action dated Oct. 5, 2010 for U.S. Appl. No. 12/046,402.
Office action dated Nov. 7, 2014 for U.S. Appl. No. 13/705,763.
Office Action dated Nov. 14, 2007 for U.S. Appl. No. 11/213,255.
Office Action dated Nov. 15, 2010 for U.S. Appl. No. 12/238,415.
Office action dated Nov. 16, 2015 for U.S. Appl. No. 13/705,763.
Office action dated Nov. 19, 2015 for U.S. Appl. No. 14/713,242.
Office action dated Nov. 20, 2015 for U.S. Appl. No. 14/296,091.
Office action dated Nov. 21, 2014 for U.S. Appl. No. 13/926,822.
Office action dated Nov. 25, 2009 for U.S. Appl. No. 11/232,180.
Office Action dated Nov. 26, 2001 for U.S. Appl. No. 09/466,559.
Office action dated Nov. 29, 2013 for U.S. Appl. No. 13/193,346.
Office action dated Dec. 6, 2012 for U.S. Appl. No. 13/002,136.
Office action dated Dec. 10, 2013 for U.S. Appl. No. 13/407,408.
Office action dated Dec. 10, 2015 for U.S. Appl. No. 13/836,135.
Office action dated Dec. 12, 2013 for U.S. Appl. No. 13/144,286.
Office action dated Dec. 13, 2013 for U.S. Appl. No. 12/493,122.
Office action dated Dec. 13, 2013 for U.S. Appl. No. 13/144,290.
Office action dated Dec. 15, 2011 for U.S. Appl. No. 12/493,147.
Office action dated Dec. 15, 2015 for U.S. Appl. No. 14/087,930.
Office action dated Dec. 16, 2013 for U.S. Appl. No. 12/535,676.
Office action dated Dec. 18, 2014 for U.S. Appl. No. 14/037,696.
Office action dated Dec. 18, 2015 for U.S. Appl. No. 14/640,385.
Office Action dated Dec. 19, 2005 for U.S. Appl. No. 10/730,567.
Office action dated Dec. 19, 2014 for U.S. Appl. No. 13/733,873.
Office Action dated Dec. 22, 2006 for U.S. Appl. No. 10/681,018.
Office action dated Dec. 24, 2015 for U.S. Appl. No. 13/757,412.
Office Action dated Mar. 18, 2008 for U.S. Appl. No. 11/468,379.
Office Action dated Mar. 25, 2008 for U.S. Appl. No. 11/213,382.
Office Action dated Mar. 28, 2008 for U.S. Appl. No. 11/555,697.
Office Action dated Apr. 12, 2010 for U.S. Appl. No. 09/990,909.
Office Action dated Apr. 21, 2008 for U.S. Appl. No. 11/232,180.
Office Action dated Apr. 22, 2003 for U.S. Appl. No. 09/929,592.
Office Action dated May 22, 2002 for U.S. Appl. No. 09/466,559.
Office Action dated Jun. 30, 2004 for U.S. Appl. No. 10/730,567.
Office Action dated Jul. 22, 2010 for U.S. Appl. No. 12/049,613.
Office Action dated Jul. 29, 2003 for U.S. Appl. No. 09/990,909.
Office Action dated Jul. 30, 2002 for U.S. Appl. No. 09/707,395.
Office Action dated Jul. 30, 2002 for U.S. Appl. No. 09/990,909.
Office Action dated Jul. 6, 2010 for U.S. Appl. No. 11/533,818.
Office Action dated Aug. 13, 2002 for U.S. Appl. No. 09/929,592.
Office Action dated Aug. 18, 2008 for U.S. Appl. No. 10/681,018.
Office Action dated Aug. 18, 2010 for U.S. Appl. No. 10/681,018.
Office Action dated Aug. 20, 2010 for U.S. Appl. No. 12/283,090.
Office Action dated Aug. 25, 2010 for U.S. Appl. No. 12/487,868.
Office Action dated Aug. 26, 2003 for U.S. Appl. No. 10/041,073.
Office Action dated Aug. 3, 2009 for U.S. Appl. No. 11/555,697.
Office Action dated Aug. 7, 2007 for U.S. Appl. No. 10/681,018.
Office Action dated Aug. 8, 2007 for U.S. Appl. No. 11/213,382.
Office Action dated Sep. 22, 2004 for U.S. Appl. No. 10/730,567.
Office Action dated Sep. 24, 2009 for U.S. Appl. No. 12/046,252.
Office Action dated May 11, 2016 U.S. Appl. No. 14/713,242.
Okahata, et al. Lipid-coated enzymes as efficient catalysts in organic media. Trends in Biotechnology. 1997; 15(2):50-54.
O'Keefe, Stephen J.D. et al. The Exacerbation of Pancreatic Endocrine Dysfunction by Potent Pancreatic Exocrine Supplements in Patients with Chronic Pancreatitis. J. Clin. Gastroenterol. 32(4):319-323 (2001).
Olivar-Parra, et al. Training referential communicative skills to individuals with autism spectrum disorder: a pilot study. Psychological Reports. 2011; 109:921-939.
Owley, et al. Multisite, double-blind, placebo-controlled trial of porcine secretin in autism. J Am Acad Child Adolesc Psychiatry. Nov. 2001;40(11):1293-9.
P.Ya. Grigoryev et al., Reference Guide on Gastroenterology, Moscow, MIA-2003, pp. 454,460,465.
Pancrease. Patient information leaflet. Pancrease HL Capsules. Last updated Apr. 30, 2013. Janssen-cilag LTD. www.medicines.org.uk/EMC/medicine/7326.
Pancreatic Enzyme Concentrate (PEC) Undiluted, Technical Data Sheet. 1 page, Scientific Protein Laboratories LLC Jun. 13, 2005.
Pancreatin 4X USP, Technical Data Sheet, 1 page, Scientific Protein laboratories LLC Jun. 13, 2005.
Pancreatin 8X USP Powder. Product Specification. Jul. 2000. In: Product Manual. American Laboratories Incorporated. Omaha, NE. p. 1.
Parisi et al. Evaluation of new rapid commercial enzyme immunoassay for detection of crytosporidium oocysts in untreated stool specimens. J Clin Microbiol. 1995; 33(7):1963-1965.
Park, et al. Increased apoptosis in cystinotic fibroblasts and renal proximal tubule epithelial cells results from cysteinylation of protein kinase Cdelta. J Am Soc Nephrol. Nov. 2006;17(11):3167-75.
Parkinsons Disease Foundation. Parkinson's Disease Q&A. 2007. 1-44.
Parkinsons Disease Foundation. Ten Frequently-Asked Questions about Parkinson's Disease. 2006.
Parracho, et al. Differences between the gut microflora of children with autistic spectrum disorders and that of healthy children. J Med Microbiol. Oct. 2005;54(Pt 10):987-91.
Patel, et al. Formulation and evaluation of mucoadhesive glipizide microspheres. AAPS PharmSciTech. 2005; 6(1):E49-E55.
Patton, J. et al. Factor structure of the Barratt impulsiveness scale. Journal of Clinical Psychology, 51(6): 768-774 (Nov. 1995).
PDTALKS. Motivational & Inspirational Speaking From a Parkinson's Patient Perspective. pdtalks.com/Parkinson_s_Disease.html. Jul. 14, 2008.
Perman et al. Role of pH in production of hydrogen from carbohydrates by colonic bacterial flora. J Clin Invest. 1981; 24(4):684-685.
Persico, et al. Searching for ways out of the autism maze: genetic, epigenetic and environmental clues. Trends Neurosci. Jul. 2006;29(7):349-58.
Peters et al. Prevalence of enteric parasites in homosexual patients attending an outpatient clinic. J of Clin Micro. 1986; 24(4):684-685.
Peters, et al. Treatment of alcoholic polyneuropathy with vitamin B complex: a randomised controlled trial. Alcohol. Nov.-Dec. 2006;41(6):636-42. Epub Aug. 21, 2006.
Petrolatum: Pharmaceutical Excipients. London: Pharmaceutical Press. 2006. 1-6.
Pisani, et al. Levodopa-induced dyskinesia and striatal signaling pathways. Proc Natl Acad Sci U S A. Mar. 3, 2009;106(9):2973-4. Epub Feb. 26, 2009.
Polanczyk, et al. The worldwide prevalence of ADHD: a systematic review and metaregression analysis. Am J Psychiatry. Jun. 2007;164(6):942-8.
Ponsky, et al. Alterations in gastrointestinal physiology after Roux-en-Y gastric bypass. J Am Coll Surg. Jul. 2005;201(1):125-31.
Preliminary Amendment dated May 18, 2009 for U.S. Appl. No. 12/046,252.
Proesmans, Marijke et al. Omeprazole, a proton pump inhibitor, improves residual steatorrhoea in cystic fibrosis patients treated with high dose pancreatic enzymes. European Journal of Pediatrics 162(11): 760-763 (Nov. 2003).
Puri, et al. Isolated segmental duodenal ganglionosis. Indian Journal of Radiology and Imaging. 2000; 153-154.
Qi, et al. Solubility and emulsifying properties of soy protein isolates modified by pancreatin. Journal of Food Science 62.6 (1997): 1110-1115.
Raimondo, et al. Rapid endoscopic secretin simulation test and discrimination of chronic pancreatitis and pancreatic cancer from disease controls. Clin Gastroenterol Hepatol. Sep. 2003;1(5):397-403.

(56) References Cited

OTHER PUBLICATIONS

Rajakumar, et al. Proteasomal activity in placentas from women with preeclampsia and intrauterine growth restriction: implications for expression of HIF-alpha proteins. Placenta. Mar. 2008;29(3):290-9. Epub Jan. 28, 2008.
Rakonczay, et al. A new severe acute necrotizing pancreatitis model induced by L-ornithine in rats. Crit Care Med. Jul. 2008;36(7):2117-27.
Ray, et al. Growth factor regulation of enterocyte nutrient transport during intestinal adaptation. Am J Surg. Apr. 2002;183(4):361-71.
Reeves, G. et al. Pharmacological Management of Attention-deficit hyperactivity disorder, Expert Opinion on Pharmacotherapy, 5:6; 1313-1320. (Feb. 25, 2005)DOI: 10.1517/14656566.5.6.1313 http://dx.doi.org/10.1517/14656566.5.6.1313.
Regan, et al. Comparative effects of antacids, cimetidine and enteric coating on the therapeutic response to oral enzymes in severe pancreatic insufficiency. N Engl J Med. Oct. 20, 1977;297(16):854-8.
Remtulla et al. Stool chymotrypsin activity measured by a spectrophotometric procedure to identify pancreatic disease in infants. Clinical Biochemistry. Dec. 1986; 19:341-342.
Response dated Oct. 3, 2006 to Restriction Requirement dated Sep. 12, 2006 for U.S. Appl. No. 10/681,018.
Response dated Apr. 29, 2010 to Notice of Non-Compliant Amendment dated Apr. 27, 2010 for U.S. Appl. No. 12/283,090.
Response dated Jun. 17, 2008 to Advisory Action dated Jun. 3, 2008 for U.S. Appl. No. 10/681,018.
Response dated Jun. 24, 2002 to Restriction Requirement dated May 22, 2002 for U.S. Appl. No. 09/990,909.
Response dated Jun. 7, 2007 to Notice of Non-Compliant Amendment dated May 7, 2007 for U.S. Appl. No. 11/213,255.
Restriction Requirement dated Jan. 10, 2008 for U.S. Appl. No. 11/232,180.
Restriction Requirement dated Jan. 13, 2010 for U.S. Appl. No. 12/487,868.
Restriction Requirement dated Oct. 17, 2007 for U.S. Appl. No. 11/555,697.
Restriction Requirement dated Oct. 7, 2009 for U.S. Appl. No. 12/283,090.
Restriction Requirement dated Dec. 10, 2009 for U.S. Appl. No. 11/533,818.
Restriction Requirement dated Apr. 23, 2003 for U.S. Appl. No. 09/990,909.
Restriction Requirement dated May 22, 2002 for U.S. Appl. No. 09/990,909.
Restriction Requirement dated May 9, 2007 for U.S. Appl. No. 11/213,382.
Restriction Requirement dated Jun. 22, 2007 for U.S. Appl. No. 11/213,255.
Restriction Requirement dated Sep. 12, 2006 for U.S. Appl. No. 10/681,018.
Revolution health. Enzyme therapy. revolutionhealth.com/drugs-treatments/enzyme-therapy. Sep. 2, 2008.
Richards, et al. Diagnosis, management, and treatment of Alzheimer disease: a guide for the internist. Arch Intern Med. Apr. 26, 1999;159(8):789-98.
Rider, et al. Perspective of biochemical research in the neuronal ceroid-lipofuscinosis. Am J Med Genet. Feb. 15, 1992;42(4):519-24.
Riedel, L et al. Limitations of faecal chymotrypsin as a screening test for chronic pancreatitis. Gut, 32:321-324 (1991).
Rivest, J. et al. A dynamic model of protein digestion in the small intestine of pigs. Journal of Animal Science, 78(2):328-240 (Feb. 2000).
Robinson, T. et al. Incentive-sensitization and addiction. Addiction, 96(1):103-114 (Jan. 2001).
Rogers. No more heartburn: Stop the pain in 30 days—naturally. 2000; 172.
Rottier, et al. Lack of PPCA expression only partially coincides with lysosomal storage in galactosialidosis mice: indirect evidence for spatial requirement of the catalytic rather than the protective function of PPCA. Hum Mol Genet. Oct. 1998;7(11):1787-94.
Roxas, et al. Colds and influenza: a review of diagnosis and conventional, botanical, and nutritional considerations. Alternative Medicine Review. 2007; 12(1):25-48.
Rubenstein, et al. Model of autism: increased ratio of excitation/inhibition in key neural systems. Genes Brain Behav. Oct. 2003;2(5):255-67.
Rudell, et al. The anterior piriform cortex is sufficient for detecting depletion of an indispensable amino acid, showing independent cortical sensory function. J Neurosci. Feb. 2, 2011;31(5):1583-90. Abstract only.
Sabra, et al. Linkage of ileal-lymphoid-nodular hyperplasia (ILNH), food allergy and CNS developmental: evidence for a non-IgE association. Ann Aller Asth Immunol. 1999; 82(1):81. Abstract only.
Sahelian. Enzymes. raysahelian.com/enzymes.html. Sep. 2, 2008.
Salpekar, et al. Bipolar Spectrum Disorder Comorbid With Autism Spectrum Disorder; NADD Bulletin, vol. X, 2007. No. 6, Article 1, pp. 1-5, downloaded from http://www.thenadd.org/nadd-bulletin/archive/volunne-x/ on Dec. 11, 2018.
Sandler et al. Short term benefit from oral vancomycin treatment of regressive-onset autism. J of Child Neuro. 2000; 15(7):42-435.
Sandler, et al. Lack of benefit of a single dose of synthetic human secretin in the treatment of autism and pervasive developmental disorder. N Engl J Med. Dec. 9, 1999;341(24):1801-6.
Schafer, et al. Stress kinases and heat shock proteins in the pancreas: possible roles in normal function and disease. J Gastroenterol. 2000;35(1):1-9.
Schain, RJ et al. Studies on 5-hydroxyindole metabolism in autistic and other mentally retarded children. J. Pediatr. 58:315-320 (1961) [Summary Only].
Schedl, H. et al. Absorption of l-methionine from the human small intestine. Journal of Clinical Investigation, 47(2): 417-425 (1968).
Schiller. Review article: the therapy of constipation. Aliment Pharmacol Ther. 2001; 15:749-763.
Schizophreniform disorder. Merck Manuals Online Medical Library. Nov. 2005. (in Japanese with English translation).
Schneider, et al. Oral human immunoglobulin for children with autism and gastrointestinal dysfunction: a prospective, open-label study. J Autism Dev Disord. Nov. 2006;36(8):1053-64.
Schreck et al. Food preferences and factors influencing food selectivity for children with autism spectrum disorders. Res Develop Disabil. 2006; 27:353-363.
Schumann. Medical, nutritional and technological properties of lactulose. An update. Eur J Nutr. Nov. 2002;41 Suppl 1:117-25.
Seltzer, et al. The Symptoms of Autism Spectrum Disorders in Adolescence and Adulthood. Journal of Autism and Developmental Disorders. 2003; 33(6):565-581.
Seneca et al. Enhancement of brain I-dopa concentration with a-chymotrypsin. J American Geriatrics Society. 1973; 256-258. Abstract only.
Serna, et al. Pathogenesis and treatment of Shiga toxin-producing *Escherichia coli* infections. Curr Opin Gastroenterol. Jan. 2008;24(1):38-47.
Settembre, et al. A block of autophagy in lysosomal storage disorders. Hum Mol Genet. Jan. 1, 2008;17(1):119-29.
Shadel. Expression and maintenance of mitochondrial DNA: new insights into human disease pathology. Am J Pathol. Jun. 2008;172(6):1445-56.
Shaul. Report to the Chairman and Ranking Minority Member, Subcommittee on Human Rights and Wellness, Committee on Government Reform, House of Representatives. GEO. Jan. 2005. 1-40.
Shelby, et al. Enzymatic debridement with activated whole pancreas. American Journal of Surgery. Oct. 1958; 96(4):545-549.
Sherwood et al. A new class of high-functionality excipients: silicified microcrystalline cellulose. Pharm Tech. 1998; 22(10):78-88.
Sherwood, et al. Activation of trypsinogen in large endocytic vacuoles of pancreatic acinar cells. Proc Natl Acad Sci U S A. Mar. 27, 2007;104(13):5674-9.

(56) References Cited

OTHER PUBLICATIONS

Shimabukuro, et al. Medical expenditures for children with an autism spectrum disorder in a privately insured population. J Autism Dev Disord. 2007;38(3):546-52.
Shpacovitch, et al. Protease-activated receptors: novel PARtners in innate immunity. Trends Immunol. Dec. 2007;28(12):541-50.
Shpacovitch, et al. Role of protease-activated receptors in inflammatory responses, innate and adaptive immunity. J Leukoc Biol. Jun. 2008;83(6):1309-22.
Sienaert, et al. Evidence-based treatment strategies for treatment-resistant bipolar depression: a systematic review. Bipolar Disord. Feb. 2013;15(1):61-9. doi: 10.1111/bdi.12026. Epub Nov. 27, 2012.
Sillanaukee, et al. Improved diagnostic classification of alcohol abusers by combining carbohydrate-deficient transferrin and gamma-glutamyltransferase. Clin Chem. Apr. 2001;47(4):681-5.
Simonoff, et al. Psychiatric disorders in children with autism spectrum disorders: prevalence, comorbidity, and associated factors in a population-derived sample. J Am Acad Child Adolesc Psychiatry. Aug. 2008;47(8):921-9.
Singh, et al. Plasma increase of interleukin-12 and interferon-gamma. Pathological significance in autism. J Neuroimmunol. May 1996;66(1-2):143-5.
Singh, Manjit. Alcoholic pancreatitis in rats fed ethanol in a nutritionally adequate liquid diet. International Journal of Pancreatology, 2:311-324 (1987).
Skeels et al. Crytosporidium infection in Oregon public health clinic patients 1985-88: the value of statewide laboratory surveillance. AJPH. 1990; 80(3):305-308.
Skinner, et al. Treatment of Prion Disease with Heterologous Prion Proteins. PLoS One. Jul. 2, 2015;10(7):e0131993. doi: 10.1371/journal.pone.0131993. eCollection 2015.
Smith, et al. Fecal chymotrypsin and trypsin determinations. Canadian Medical Association Journal. 1971; 104(8):691-4 and 697.
Sousa, et al. Polymorphisms in leucine-rich repeat genes are associated with autism spectrum disorder susceptibility in populations of European ancestry. Mol Autism. Mar. 25, 2010;1(1):7.
Statemaster. Number of Children with Autism (most recent w/graph) by state. Statemaster.com Jul. 14, 2003.
Statemaster. Number of Children with Autism (most recent) by state. Statemaster.com Jul. 14, 2008.
Statemaster. Number of Children with Autism (per capita)(most recent) by state. Statemaster.com Jul. 14, 2003.
Stein, et al. Nitrogen metabolism in normal and hyperkinetic boys. Am J Clin Nutr. Apr. 1984;39(4):520-4.
Steinherz, et al. Patterns of amino acid efflux from isolated normal and cystinotic human leucocyte lysosomes. J Biol Chem. Jun. 10, 1982;257(11):6041-9.
Sternby, et al. Carboxyl Ester Lipase (Bile Salt-Stimulated Lipase), Colipase, Lipase, and Phospholipase A2 Levels in Pancreatic Enzyme Supplements, 1997, Scandinavian Journal of Gastroenterology 32(3): 261-267.
Stoll, et al. Enteral nutrient intake level determines intestinal protein synthesis and accretion rates in neonatal pigs. Am J Physiol Gastrointest Liver Physiol. Aug. 2000;279(2):G288-94.
Stott, et al. MMR and Autism in Perspective: the Denmark Story. J. Am Phys Surg. 2004; 9(3):89-91.
Strader, et al. Structural basis of β-adrenergic receptor function. FASEB J. May 1989;3(7):1825-32.
Sturmey. Secretin is an ineffective treatment for pervasive developmental disabilities: a review of 15 double-blind randomized controlled trials. Res Dev Disabil. Jan.-Feb. 2005;26(1):87-97.
Sundstrom, et al. A deadly prion disease: fatal familial insomnia. J Neurosci Nurs. Dec. 2003;35(6):300-5. Abstract only.
Supplemental Amendment and Response dated Jan. 8, 2010 to Restriction Requirement dated Oct. 7, 2009 for U.S. Appl. No. 12/283,090.
Swayne, et al. Pathobiology of H5N2 Mexican avian influenza virus infections of chickens. Vet Pathol. Nov. 1997;34(6):557-67.
Tager-Flusberg, et al. Language disorders: autism and other pervasive developmental disorders. Pediatr Clin North Am. Jun. 2007;54(3):469-81, vi.
Tamaro. Vitamin K deficiency as a cause of autistic symptoms. Http://web.archive.org/web/20090612022246/http://www.gutresearch.com/VitaminK.pdf. Published Jun. 12, 2009 as per Wayback Engine.
Tang, G. et al. Loss of mTOR-dependent macroautophagy causes autistic-like synaptic pruning deficits. Neuron, 83(5):1131-1143 (Sep. 3, 2014).
Terrie, et al. Understanding Pancreatic Enzyme Products. Dec. 15, 2008.
The Alzheimer's Association. Basics of Alzheimer's Disease. 2005, 32 pages. http://www.alz.org/national/documents/brochure_Basicsofalz_low/pdf.
Thefreedictionary. Term Sprinkles. Www.thefreedictionary.com. Accessed Nov. 2, 2011. 1 page.
Therapeutic research center. Approved Pancreatic Enzyme Products. Pharmacist's Letter/Prescriber's Letter 2010. Oct. 2010. 1-3.
Thomas, et al. Defective protein folding as a basis of human disease. Trends Biochem Sci. Nov. 1995;20(11):456-9.
Tiedermann, et al. Identification of a potent natural triterpenoid inhibitor of proteosome chymotrypsin-like activity and NF-kappaB with antimyeloma activity in vitro and in vivo. Blood. Apr. 23, 2009;113(17):4027-37.
Torrente, et al. Focal-enhanced gastritis in regressive autism with features distinct from Crohn's and Helicobacter pylori gastritis. Am J Gastroenterol. Apr. 2004;99(4):598-605.
Torrente, et al. Small intestinal enteropathy with epithelial IgG and complement deposition in children with regressive autism. Mol Psychiatry. 2002;7(4):375-82, 334.
Tran, et al. Treatment of complex regional pain syndrome: a review of the evidence. Can J Anaesth. Feb. 2010;57(2):149-66.
Trauner, et al. Specific cognitive deficits in young children with cystinosis: evidence for an early effect of the cystinosin gene on neural function. J Pediatr. Aug. 2007;151(2):192-6.
Troy. Pancreatic Enzymes. Remington: The Science and Practice of Pharmacy, 21st edition. Lippincot Williams & Wilkins, 2006. p. 1304.
Tsan, et al. Heat shock proteins and immune system. J Leukoc Biol. Jun. 2009;85(6):905-10.
Tsang et al. Extragastroduodenal conditions associated with Helicobacter pylori infection. Hong Kong Medical Journal. 1999; 5(2):169-174.
Tuohy, K.M. et al. Using probiotics and prebiotics to improve gut health. Reviews, Therapeutic Focus, DDT 8(15) Aug. 2003.
U.S. Appl. No. 12/054,343 Non-Final Office Action dated Dec. 26, 2017.
U.S. Appl. No. 12/535,676 Final Office Action dated Feb. 8, 2018.
U.S. Appl. No. 12/535,676 Non-Final Office Action dated Sep. 6, 2018.
U.S. Appl. No. 12/535,676 Office Action dated Sep. 13, 2016.
U.S. Appl. No. 12/786,739 Final Office Action dated Jun. 23, 2017.
U.S. Appl. No. 12/786,739 Final Office Action dated Sep. 25, 2018.
U.S. Appl. No. 12/786,739 Non-Final Office Action dated Jan. 4, 2018.
U.S. Appl. No. 12/786,739 Office Action dated Sep. 20, 2016.
U.S. Appl. No. 13/002,136 Advisory Office Action dated Jul. 9, 2018.
U.S. Appl. No. 13/002,136 Final Office Action dated Jan. 8, 2018.
U.S. Appl. No. 13/002,136 Final Office Action dated Jun. 24, 2016.
U.S. Appl. No. 13/002,136 Non-Final Office Action dated Dec. 18, 2018.
U.S. Appl. No. 13/002,136 Non-Final Office Action dated Feb. 27, 2017.
U.S. Appl. No. 13/193,346 Notice of Allowability dated Jul. 14, 2016.
U.S. Appl. No. 13/193,346 Notice of Allowability dated Jun. 2, 2016.
U.S. Appl. No. 13/313,629 Notice of Allowance dated Dec. 22, 2016.
U.S. Appl. No. 13/313,708 Notice of Allowance dated Dec. 15, 2016.
U.S. Appl. No. 13/502,989 Notice of Allowance dated Aug. 10, 2016.

(56) References Cited

OTHER PUBLICATIONS

U.S. Appl. No. 13/503,844 Final Office Action dated Nov. 30, 2017.
U.S. Appl. No. 13/503,844 Office Action dated Aug. 25, 2016.
U.S. Appl. No. 13/503,844 Office Action dated Mar. 27, 2017.
U.S. Appl. No. 13/733,873 Final Office Action dated Feb. 21, 2018.
U.S. Appl. No. 13/733,873 Non-Final Office Action dated May 25, 2017.
U.S. Appl. No. 13/757,412 Final Office Action dated Jun. 30, 2016.
U.S. Appl. No. 13/757,412 Final Office Action dated Sep. 12, 2017.
U.S. Appl. No. 13/757,412 Office Action dated Feb. 10, 2017.
U.S. Appl. No. 13/836,135 Final Office Action dated May 15, 2017.
U.S. Appl. No. 13/836,135 Non-Final Office Action dated Mar. 15, 2018.
U.S. Appl. No. 13/836,135 Office Action dated Jul. 22, 2016.
U.S. Appl. No. 14/296,091 Final Office Action dated Aug. 23, 2017.
U.S. Appl. No. 14/296,091 Final Office Action dated Jan. 3, 2017.
U.S. Appl. No. 14/296,091 Final Office Action dated Oct. 1, 2018.
U.S. Appl. No. 14/296,091 Non-Final Office Action dated Mar. 22, 2018.
U.S. Appl. No. 14/612,580 Final Office Action dated Aug. 10, 2017.
U.S. Appl. No. 14/612,580 Notice of Allowability dated Mar. 1, 2018.
U.S. Appl. No. 14/612,580 Notice of Allowance dated Jan. 12, 2018.
U.S. Appl. No. 14/612,580 Office Action dated Sep. 21, 2016.
U.S. Appl. No. 14/612,604 Notice of Allowance dated Jul. 20, 2016.
U.S. Appl. No. 14/639,425 Notice of Allowance dated Mar. 10, 2017.
U.S. Appl. No. 14/639,425 Office Action dated Jul. 14, 2016.
U.S. Appl. No. 14/693,711 Final Office Action dated Dec. 15, 2016.
U.S. Appl. No. 14/693,711 Notice of Allowability dated May 26, 2017.
U.S. Appl. No. 14/693,711 Notice of Allowance dated Apr. 21, 2017.
U.S. Appl. No. 14/713,178 Advisory Office Action dated Jan. 19, 2017.
U.S. Appl. No. 14/713,178 Final Office Action dated Oct. 14, 2016.
U.S. Appl. No. 14/713,178 Notice of Allowance dated Apr. 12, 2017.
U.S. Appl. No. 14/713,221 Final Office Action dated Jun. 16, 2016.
U.S. Appl. No. 14/713,221 Non-Final Office Action dated Dec. 30, 2016.
U.S. Appl. No. 14/713,242 Final Office Action dated Jan. 9, 2019.
U.S. Appl. No. 14/713,242 Final Office Action dated Jul. 21, 2017.
U.S. Appl. No. 14/713,242 Non-Final Office Action dated Mar. 29, 2018.
U.S. Appl. No. 14/713,242 Office Action dated Dec. 7, 2016.
U.S. Appl. No. 14/921,896 Final Office Action dated Jan. 25, 2018.
U.S. Appl. No. 14/921,896 Notice of Allowability dated Sep. 12, 2018.
U.S. Appl. No. 14/921,896 Notice of Allowance dated Jul. 18, 2018.
U.S. Appl. No. 14/921,896 Office Action dated Apr. 26, 2017.
U.S. Appl. No. 15/089,842 Non-Final Office Action dated Jun. 26, 2018.
U.S. Appl. No. 15/089,842 Office Action dated Dec. 8, 2017.
U.S. Appl. No. 15/164,493 Non-Final Office Action dated Feb. 27, 2018.
U.S. Appl. No. 15/164,493 Notice of Allowance dated Nov. 15, 2018.
U.S. Appl. No. 15/185,511 Notice of Allowance dated Nov. 16, 2017.
U.S. Appl. No. 15/265,415 Non-Final Office Action dated Apr. 11, 2018.
U.S. Appl. No. 15/265,620 Non-Final Office Action dated Jun. 20, 2018.
U.S. Appl. No. 15/354,940 Non-Final Office Action dated Nov. 2, 2018.
U.S. Appl. No. 15/593,121 Non-Final Office Action dated Mar. 8, 2018.
U.S. Appl. No. 15/593,129 Office Action dated Jan. 3, 2019.
U.S. Appl. No. 14/528,715, filed Oct. 30, 2014.
U.S. Appl. No. 14/612,580, filed Feb. 3, 2015.
U.S. Appl. No. 14/612,604, filed Feb. 3, 2015.
U.S. Appl. No. 14/693,711, filed Apr. 22, 2015.
U.S. Appl. No. 14/713,178, filed May 15, 2015.
U.S. Appl. No. 14/713,221, filed May 15, 2015.
U.S. Appl. No. 14/713,242, filed May 15, 2015.
U.S. Appl. No. 12/535,676 Office Action dated Jun. 26, 2019.
U.S. Appl. No. 13/002,136 Office Action dated Jun. 21, 2019.
U.S. Appl. No. 14/612,580 Office Action dated Dec. 24, 2015.
U.S. Appl. No. 12/786,739 Office Action dated May 8, 2019.
U.S. Appl. No. 13/733,873 Office Action dated May 16, 2019.
U.S. Appl. No. 15/074,115 Office Action dated Mar. 6, 2019.
U.S. Appl. No. 15/089,842 Notice of Allowance dated Mar. 29, 2019.
U.S. Appl. No. 15/265,415 Notice of Allowance dated Dec. 26, 2018.
U.S. Appl. No. 15/593,121 Notice of Allowance dated Dec. 26, 2018.
Uhlmann, et al. Potential viral pathogenic mechanism for new variant inflammatory bowel disease. Mol Pathol. Apr. 2002;55(2):84-90.
Ultresa—FDA Prescribing Information Side Effects and Uses. Revised Sep. 2014.
Ultresa. Highlights of prescribing information. Aptalis Pharma US Inc. Revised Mar. 2012.
Unis, et al. A randomized, double-blind, placebo-controlled trial of porcine versus synthetic secretin for reducing symptoms of autism. J Am Acad Child Adolesc Psychiatry. Nov. 2002;41(11):1315-21.
U.S. Appl. No. 15/354,940 Final Office Action dated Aug. 21, 2019.
U.S. Appl. No. 15/840,883 Office Action dated Aug. 8, 2019.
U.S. Appl. No. 16/010,850 Restriction Requirement dated Jun. 21, 2019.
U.S. Appl. No. 16/103,192 Restriction Requirement dated Aug. 9, 2019.
UPI. Number of autistic Calif. students triples. United Press International. Jul. 12, 2008.
USDA. FDA Drug Safety Communication: Clostridium difficile-associated diarrhea can be associated with stomach acid drugs known as proton pump inhibitors (PPIs). Safety announcement. Feb. 8, 2012. Accessed Apr. 1, 2013. http://www.fda.gov/drugs/drugsafety/ucm290510.htm.
USP (32)-NF(27) 2009, Pancreatin, V.3, pp. 3194-3195.
Valicenti-McDermott, et al. Frequency of gastrointestinal symptoms in children with autistic spectrum disorders and association with family history of autoimmune disease. J Dev Behav Pediatr. Apr. 2006;27(2 Suppl):S128-36.
Vargas, et al. Neuroglial activation and neuroinflammation in the brain of patients with autism. Ann Neurol. Jan. 2005;57(1):67-81.
Vellard. The enzyme as drug: application of enzymes as pharmaceuticals. Curr Opin Biotechnol. Aug. 2003;14(4):444-50.
Vilanova, et al. Preparative isolation of the two forms of pig pancreatic pro-(carboxypeptidase A) and their monomeric carboxypeptidases A. Biochem J. Aug. 1, 1985;229(3):605-9.
Viokace—FDA Prescribing Information, Side Effects and Uses. Revised Mar. 2012.
Viokace. Highlights of prescribing information. Aptalis Pharma US Inc. Revised Mar. 2012.
Vojdani, et al. Antibodies against CNS antigens in autism: Possible cross-reaction with dietary proteins and infectious agent antigens. Neuropsychiatric Disorders and Infection. 2004; 19:171-186.
Vojdani, et al. Heat shock protein and gliadin peptide promote development of peptidase antibodies in children with autism and patients with autoimmune disease. Clin Diagn Lab Immunol. May 2004;11(3):515-24.
Vojdani, et al. Immune response to dietary proteins, gliadin and cerebellar peptides in children with autism. Nutr Neurosci. Jun. 2004;7(3):151-61.
Volkmar, et al. Practice parameters for the assessment and treatment of children, adolescents, and adults with autism and other pervasive developmental disorders. American Academy of Child and Adolescent Psychiatry Working Group on Quality Issues. J Am Acad Child Adolesc Psychiatry. (Part 1) Dec. 1999;38(12 Suppl):32S-54S.

(56) References Cited

OTHER PUBLICATIONS

Volkmar, et al. Practice Parameters for the Assessment and Treatment of Children, Adolescents, and Adults with Autism and other Pervasive Developmental Disorders. American Academy of Child and Adolescent Psychiatry. J Am Acad Child Adolesc Psychiatry. (Part 2) Dec. 1999;38(12):1611-6.
Wakefield, et al. Enterocolitis in children with developmental disorders. Am J Gastroenterol. Sep. 2000;95(9):2285-95.
Wakefield, et al. Ileal-lymphoid-nodular hyperplasia, non-specific colitis, and pervasive developmental disorder in children. Lancet. Feb. 28, 1998;351(9103):637-41.
Wakefield, et al. Review article: the concept of entero-colonic encephalopathy, autism and opioid receptor ligands. Aliment Pharmacol Ther. Apr. 2002;16(4):663-74.
Wakefield, et al. The significance of ileo-colonic lymphoid nodular hyperplasia in children with autistic spectrum disorder. Eur J Gastroenterol Hepatol. Aug. 2005;17(8):827-36.
Wakefield. Autistic enterocolitis: is it a histopathological entity? Histopathology. 2006; 1-5.
Wakefield. Enterocolitis, Autism, and Measles Virus. Consensus in Child Neurology: Biological Bases and Clinical Perspectives in Autism. 2002; 74-81.
Wakefield. The gut-brain axis in childhood developmental disorders. J Pediatr Gastroenterol Nutr. May-Jun. 2002;34 Suppl 1:S14-7.
Walsh, et al. Heat shock and the role of the HSPs during neural plate induction in early mammalian CNS and brain development. Cell Mol Life Sci. Feb. 1997;53(2):198-211.
Walsh, et al. Reduced violent behavior following chemical therapy. Physiology and behavior. 2004; 82:835-839.
Wang, et al. Activation of Ras/Erk pathway by a novel MET-interacting protein RanBPM. J Biol Chem. Sep. 27, 2002;277(39):36216-22.
Wang, et al. Effect of chymotrypsin C and related proteins on pancreatic cancer cell migration. Acta Biochim Biophys Sin (Shanghai). May 2011;43(5):362-71. Epub Apr. 2, 2011. Jan. 7, 2011. Abstract only.
We Move, PD Workbook, the Wemove Clinician's Guide to Parkinson's Disease, 2006.
Weintraub, et al. Morphometric studies of pancreatic acinar granule formation in NCTR-Balb/c mice. J Cell Sci. May 1992;102 (Pt 1):141-7.
Welch, et al. Brain effects of chronic IBD in areas abnormal in autism and treatment by single neuropeptides secretin and oxytocin. J Mol Neurosci. 2004;25(3):259-74.
Wender et al. Prevalence of attention deficit disorder, residual type, and other psychiatric disorders in patients with irritable colon syndrome. Am J Psychiatry. 1983; 140(12):1579-82 Abstract only.
Whitehouse. Fact Sheet: Combating Autism Act of 2006. www.whitehouse.gov. Dec. 19, 2006.
Williams, et al. Eating habits of children with autism. Pediatr Nurs. May-Jun. 2000;26(3):259-64.
Williams, et al. Intravenous secretin for autism spectrum disorders (ASD). Cochrane Database Syst Rev. Apr. 18, 2012;4:CD003495. doi: 10.1002/14651858.CD003495.pub3.
Williams, K. et al. Cochrane Review: Selective serotonin reuptake inhibitors (SSRIs) for autism spectrum disorders (ASD). Evidence-Based Child Health: A Cochrane Review Journal, 6(4): 1044-1078 (Jul. 2011). [Abstract Only].
Wisniewski, et al. Therapeutic approaches for prion and Alzheimer's diseases. FEBS J. Aug. 2007;274(15):3784-98. Epub Jul. 6, 2007.
Witmer. ADD and ADHD Statistics—CDC Report Looks at Attention-Deficit/Hyperactivity Disorder. About.com—Parenting of Adolescents. Jul. 15, 2008.
Wohlman et al. Enhancement of drug activity by chymotrypsin, penicillin penetration into granulomatous lesions and inflammatory fluids. Cellular and Molecular Life Sciences. 1969; 25(9):953-954.
Wolfson, D., Making sense of digestive enzymes, Klaire Labs, Mar. 13, 2006.
Woodward et al. Ischaemic enterocolitis complicating aidiopathic dysautonomia. Gut. 1998; 43:285-287.
Xu. Pancreatin therapy in chronic pancreatitis. Clin J Dig, May 2005; 25(5):313-315. (in Chinese with English translation).
Yahoo!.com. Who is affected by Parkinson's disease. Yahoo! Health. Jul. 14, 2008.
Yang, et al. Polymeric Porous Framework of a Bismuth Citrate-Based Complex: A Potential Vehicle for Drug Delivery. Medical News Today. Dec. 17, 2010. 1-4.
Yang, Xinyi et al. Advances in anti-staphylococcal agent lysostaphin. Chinese Journal of New Drugs 14(9):1113-1117 (2005).
Yazbak. Autism in the United States: a perspective. Journal of American Physicians and Surgeons. 2003;8:103-107.
Youngberg, et al. Comparison of gastrointestinal pH in cystic fibrosis and healthy subjects. Dig Dis Sci. May 1987;32(5):472-80.
Yuan, et al. Freeze-Thaw Stability of Three Waxy Maize Starch Pastes Measured by Centrifugation and Calorimetry. Cereal Chem. 1998; 75(4):571-573.
Zeiner, et al. Mammalian protein RAP46: an interaction partner and modulator of 70 kDa heat shock proteins. EMBO J. Sep. 15, 1997;16(18):5483-90.
ZENPEP—FDA Prescribing Information, Side Effects and Uses. Revised Sep. 2014.
ZENPEP. Highlights of prescribing information. Eurand Pharmaceuticals Inc. Revised Jul. 2011.
Zhang et al. Lactulose-mannitol intestinal permeability test in children with diarrhea caused by rotavirus and cryptosporidium. J of Pediatric Gastro & Nutrition. 2000; 31(1):16-21.
Capua et al., Influenza A viruses grow in human pancreatic cells and cause pancreatitis and diabetes in an animal model. Journal of Virology 87(1): 597-610 (2013).
DeFelice, Viruses Part 2-results of two informal studies, Chapter 14. In: Enzymes: Go with your Gut-more practical guidelines for digestive enzymes. Published by ThunderSnow. pp. 195-218 (2006).
European Patent Application No. 13733621.0 Examination Report dated Sep. 4, 2019.
International Preliminary Report on Patentability dated Oct. 15, 2019 for PCT/US2018/026841.
Lockner et al. Dietary intake and parents' perception of mealtime behaviors in preschool-age children with autism spectrum disorder and in typically developing children. J Am Diet Assoc 108(8):1360-1363 (2008).
National Institutes of Health. Thin Bones Seen in Boys with Autism and Autism Spectrum Disorder. 3 pages (2008).
Naver.com entry for Rare Disease Information: Osteopenia—Osteopsathyrosis, Fragilitasossium, Fragilitasossium (accessed Sep. 25, 2019).
Singh et al. Past, Present, and Future Technologies for Oral Delivery of Therapeutic Proteins. J Pham Sci 97(7):2497-2523 (2008).
U.S. Appl. No. 13/733,873 Final Office Action dated Feb. 6, 2020.
U.S. Appl. No. 15/889,917 Final Office Action dated Feb. 13, 2020.
U.S. Appl. No. 16/103,192 Office Action dated Nov. 4, 2019.
Amsterdam, D. Susceptibility testing of antimicrobials in liquid media. Antibiotics in Laboratory Medicine. 52-111 (1996).
Barboza et al., Measurement of intestinal permeability using mannitol and lactulose in children with diarrheal diseases. Brazilian Journal of Medical and Biological Research 32: 1499-1504 (1999).
Barry, J. Mode of action of penetration enhancers in human skin. Controlled Release 6: 85-97 (1987).
D'Eufemia et al., Abnormal intestinal permeability in children with autism. Acta Paediatr 85: 1076-1079 (1996).
Fan et al., Guidelines for Standard Operation of Toxicological Safety Assessment (vol. 1). University of Electronic Science and Technology Press (2009).
Harrison, Bipolar Disorder. Healing Depression Naturally, Twin Streams. Kensington Publishing Corp: 31-32. (2004).
Horsmans et al., Lactulose improves psychometric testing in cirrhotic patients with subclinical encephalopathy. Aliment Pharmocol Ther 11:165-170 (1997).
Schlessingerman, Mass of an Adult. The Physics Factbook (2003).
Thomas, Bipolar Disorder-Balancing Moods by Balancing Nutrients; What Doctors Don't Tell You. 14)7): 1-13 (2003).
U.S. Appl. No. 13/002,136 Final Office Action dated Sep. 11, 2020.

(56) References Cited

OTHER PUBLICATIONS

U.S. Appl. No. 15/889,917 Non-Final Office Action dated Sep. 3, 2020.
U.S. Appl. No. 16/422,079 Final Office Action dated Sep. 16, 2020.
U.S. Appl. No. 13/002,136 Non-Final Office Action dated May 26, 2020.
U.S. Appl. No. 15/265,620 Notice of Allowance dated Apr. 29, 2020.
U.S. Appl. No. 15/354,940 Final Office Action dated Jul. 2, 2020.
U.S. Appl. No. 15/840,883 Final Office Action dated Jun. 9, 2020.
U.S. Appl. No. 16/281,908 Non-Final Office Action dated May 1, 2020.
U.S. Appl. No. 16/422,079 Non-Final Office Action dated Apr. 20, 2020.
Xie, Development and Application of New Traditional Chinese Medicine 2nd Edition. People's Medical Publishing House (2000).

\* cited by examiner

| TEST ARTICLES | | | | |
|---|---|---|---|---|
| Name | Code Number | Strength | Purity | Other Characteristics |
| Pancreatin compound | CM 100 | Low Dose:<br><br>10 mg Pancreatine suspended in 1 ml of water<br><br>High Dose:<br><br>20 mg Pancreatine suspended in 1 ml of water | Not assayed | Test article is a protease that is slightly soluble in water, insoluble in alcohol, heat labile, able to be frozen/thawed<br><br>Supplied article was light brown powder. |

FIGURE 1

DOSAGE

| Dosage | Description |
|---|---|
| Low | 10 mg Pancreatin suspended in 1 ml of water |
| High | 20 mg Pancreatin suspended in 1 ml of water |

FIGURE 2

| DOSAGE | PROTEASE LEVEL ACTIVITY |
|---|---|
| 10 mg/ml | human equivalent of 155,000 units |
| 20 mg/ml | human equivalent of 310,000 units |

FIGURE 3

METHOD OF TREATMENT OF SCHIZOPHRENIFORM DISORDER

CROSS-REFERENCE

This application is a continuation of U.S. application Ser. No. 15/265,415, filed Sep. 14, 2016, which is now U.S. Pat. No. 10,279,016, which is a continuation of U.S. application Ser. No. 14/612,604, filed Feb. 3, 2015, now U.S. Pat. No. 9,492,515, which is a continuation of U.S. application Ser. No. 14/007,793, filed Dec. 27, 2013, now U.S. Pat. No. 8,980,252, which is a § 371 U.S. National Phase Entry of PCT/US12/34489, filed Apr. 20, 2012, which claims the benefit of U.S. Provisional Application No. 61/477,988, filed Apr. 21, 2011, which application is incorporated herein by reference in its entirety.

BACKGROUND OF THE INVENTION

Neuropsychiatric Disorders are some of the most debilitating, socially isolating and economically draining of all illnesses. The manifestations of Neuropsychiatric Disorders, often mistaken as willful or controllable behaviors cause the illness to be misdiagnosed and thus poorly treated. Most treatments for Neuropsychiatric Disorders have severe and devastating side effects. These side effects will often discourage the patient from continuing treatment and are often the cause of relapse.

Psychotic Disorders represent the most difficult of all Neuropsychiatric Disorders to control. The invariate nature of the presentation of symptoms of these disorders, together with the side effects exhibited by medications used to alleviate these symptoms, makes their treatment difficult.

The introduction of antipsychotic drugs in the 1950's heralded the "golden age" of psychopharmacology. Their development has been compared to the discovery of antibiotics for infectious diseases. Conventional or "typical" antipsychotic drugs, typified by chlorpromazine and haloperidol, have a proven track record in the treatment of Schizophrenia.

However, the "typical" antipsychotics described below have substantial limitations. They are most effective against the psychotic symptoms of the illness in its early stages, but their side effects are troubling and contribute significantly to non-compliance, which leads to relapse and re-hospitalization.

SUMMARY OF THE INVENTION

There is a growing belief among clinicians that the "atypical" antipsychotics are or should become first-line treatments in Schizophrenia. However, the exact nature and extent of the clinical advantages of the atypical drugs are not known. Moreover, they may cost ten times as much as older "typical" antipsychotics. Although a variety of claims of efficacy and safety have been made, they are often based on insufficient evidence.

Among the reasons for this is traditional clinical trials have excluded many patients with Schizophrenia, including those who are substance abusers, violent or uncooperative, making it difficult to generalize the results of such studies to real world patients. For reasons of external validity, treatment effectiveness studies have sought to use more representative sampling techniques. However, even effectiveness studies rarely have representative samples of providers and systems of care, or large enough samples to have sufficient power to examine the role of external factors affecting treatment outcome.

There is a need for a new class of drugs to treat Neuropsychiatric Disorders, with at least equal effectiveness, but with a severely reduced side effect profile, which will enhance compliance and lower co-morbid symptomatology.

Provided herein are compositions of digestive enzymes which are useful in the prevention or treatment of one or more symptoms of a Neuropsychiatric Disorder. Also provided herein are compositions of digestive enzymes which are useful for use in the prevention or treatment of one or more symptoms of Schizophrenia. Treatment of a Neuropsychiatric Disorder (e.g., Schizophrenia) encompasses stasis of one or more symptoms (i.e., they do not worsen), as well as reduction (partial or complete) of one or more symptoms. In one embodiment, one or more symptoms of such disorders are reduced in severity or duration by about 2%, about 5%, about 10%, about 15%, about 20%, about 25%, about 30%, about 35%, about 40%, about 45%, about 50%, about 55%, about 60%, about 65%, about 70%, about 75%, about 80%, about 90%, about 95%, or about 100%. In another embodiment, one or more symptoms of such disorders are reduced in severity or duration by about 2-fold, about 5-fold, about 10-fold, about 15-fold, about 20-fold, about 25-fold, about 30-fold, about 35-fold, about 40-fold, about 45-fold, about 50-fold, about 55-fold, about 60-fold, about 65-fold, about 70-fold, about 75-fold, about 80-fold, about 90-fold, about 95-fold, about 100-fold or more. Compositions may include not only one or more digestive enzymes, but also one or more pharmaceutically acceptable carriers, excipients, buffers, fillers, binders, stabilizers, surfactants, diluents, taste maskers, etc.

Provided herein is a method for using digestive enzymes and their derivatives to alleviate one or more symptoms of Neuropsychiatric Disorders. The method comprises administering to the individual one or more digestive enzymes that are either naturally- or recombinantly-derived, or their derivatives, in an amount effective to reduce the one or more symptoms of the Neuropsychiatric Disorder. Digestive enzymes generally comprise all proteases, amylases, and lipases, as well as other proteins secreted in a mammal that affect the digestive process either directly or indirectly.

The disorders that present symptoms potentially suitable for alleviation according to the present method include, but are not limited to: Adjustment Disorders, Addiction, Alzheimer's Disease, Anxiety Disorders, Bipolar Disorder, Cognitive Disorders, Dementias, Dissociative Disorders, Eating Disorders, Impulse-Control Disorders, Mood Disorders, Sexual Disorders, Sleep Disorders, Psychotic Disorders such as Schizophrenic Disorders, Somatoform Disorders, Substance Abuse Disorders and Personality Disorders. In one embodiment, a Schizophreniform Disorder (e.g., Schizophrenia) is treated according to the methods described herein In another aspect, this disclosure relates to a pharmaceutical composition comprising a therapeutically effective amount of an enzyme preparation, which comprises a core amount of pancreatic or digestive enzymes effective for treating a subject susceptible to treatment by the enzymes, specifically those suffering with Neuropsychiatric Disorders.

In another aspect, this disclosure relates to a pharmaceutical composition comprising a therapeutically effective amount of an enzyme preparation, which comprises a core amount of pancreatic or digestive enzymes effective for treating a subject susceptible to treatment by the enzymes, specifically those suffering with Schizophrenia.

In another aspect, this disclosure relates to a pharmaceutical composition comprising a therapeutically effective amount of an enzyme preparation, which comprises a core amount of pancreatic or digestive enzymes effective for treating a subject susceptible to treatment by the enzymes, specifically those suffering with psychosis.

In one aspect, provided herein is a method for treating an individual exhibiting one or more symptoms of a Neuropsychiatric Disorder, the method comprising administering a therapeutically effective amount of digestive enzymes to the individual. In one embodiment, the Neuropsychiatric Disorder is a Schizophreniform Disorder, or a mild anxiety state.

In another embodiment, a symptom of the Neuropsychiatric Disorder may be a positive symptom, a negative symptom, a symptom of cognitive impairment, or a combination thereof. Positive symptoms are include, but are not limited to hallucinations, delusions, disorganized thought, disorganized speech (e.g., frequent derailment or incoherence), movement disorders, bizarre behavior, and any combinations thereof. Negative symptoms include, but are not limited to limited to loss of motivation, restricted range of emotional experience and expression, reduced hedonic capacity, affective flattening, alogia, avolition, and any combinations thereof. Symptoms of cognitive impairment include, but are not limited to poor executive function, inability to use learned information, difficulty paying attention and/or focusing, and any combinations thereof.

Digestive enzymes to be used in a composition described herein include amylase, lipase, protease, and any combination thereof. In another embodiment, digestive enzymes to be used in such compositions may further include chymotrypsin, trypsin, pancreatin, papain, and any combination thereof. Digestive enzymes may be derived from a source such as, for example, animal enzymes, plant enzymes, synthetic enzymes, and any combination thereof. In a one embodiment, the animal enzyme is derived from a mammal.

Digestive enzymes may be manufactured using any appropriate technology including, but not limited to, enteric coating, lipid encapsulation, direct compression, dry granulation, wet granulation, and any combination thereof. A preparation may be an oral dosage formulation such as, for example, pills, tablets, capsules, microcapsules, mini-capsules, time released capsules, mini-tabs, sprinkles, and any combination thereof. In one embodiment digestive enzymes are provided as a pharmaceutical composition. In one embodiment the pharmaceutical composition is in the form of encapsulated sprinkles. In one embodiment the encapsulation is a lipid coating. In one embodiment the lipid coating is a soy lipid coating.

Provided herein is a method is presented for treating a symptom of a Neuropsychiatric Disorder in an individual comprising administering an effective amount of a composition comprising one or more digestive enzymes to the individual. In one embodiment, the Neuropsychiatric Disorder is Schizophrenia, Schizophreniform Disorders, or mild anxiety states.

In one embodiment, the digestive enzyme is selected from the group consisting of amylase, lipase, protease, and any combination thereof. In another embodiment, the digestive enzyme is further selected from the group consisting of: chymotrypsin, trypsin, pancreatin, papain, and any combination thereof. In yet another embodiment, the digestive enzymes are derived from a source selected from the group consisting of animal enzymes, plant enzymes, synthetic enzymes, and any combination thereof. In one embodiment the digestive enzymes are pancreatic digestive enzymes. In one embodiment, the animal enzyme is derived from a mammal. In one embodiment the mammal is a pig. In one embodiment, digestive enzymes are derived from a mammalian pancreas. In one embodiment the pancreas is a pig pancreas.

In one embodiment, the total amount of protease in a composition ranges from about 5,000 to about 1,500,000 U.S.P. units/dose. In another embodiment, the total amount of amylase in a composition ranges from about 1,000 to about 15,000,000 U.S.P. units/dose. In another embodiment, the total amount of lipase in a composition ranges from about 1,500 to about 282,000 U.S.P. units/dose. In one embodiment a pharmaceutical composition comprises about 23,000 U.S.P. units/dose of lipase, about 144,000 U.S.P. units/dose of amylase, and about 140,000 U.S.P. units/dose of protease. In another embodiment a pharmaceutical composition contains 23040 U.S.P. units/dose of lipase, about 144,000 U.S.P. units/dose of amylase, and about 140,400 U.S.P. units/dose of protease.

Provided herein are methods for preventing or treating one or more symptoms of a Neuropsychiatric Disorder in an individual comprising, administering to said individual a composition comprising one or more digestive enzymes, wherein one or more symptoms of said Neuropsychiatric Disorder are partially or completely reduced. In one aspect, the Neuropsychiatric Disorder is a Schizophreniform Disorder such as, for example, Schizophrenia. Symptoms of Schizophrenia that may be treated with such methods include, but are not limited to, positive symptoms, negative symptoms, cognitive impairment, and any combination thereof. Positive symptoms include, but are not limited to, hallucinations, delusions, disorganized thought, disorganized speech (e.g., frequent derailment or incoherence), movement disorders, bizarre behavior, and any combination thereof. Negative symptoms include, but are not limited to, loss of motivation, restricted range of emotional experience and expression, reduced hedonic capacity, affective flattening, alogia, avolition, and any combination thereof. Symptoms of cognitive impairment include, but are not limited to, poor executive function, inability to use learned information, difficulty paying attention and/or focusing, and any combination thereof.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings.

FIG. 1. The Test Substances.

FIG. 2. Description of the Dosages.

FIG. 3. Description of the Enzyme Components.

DETAILED DESCRIPTION OF THE INVENTION

Figure 4:
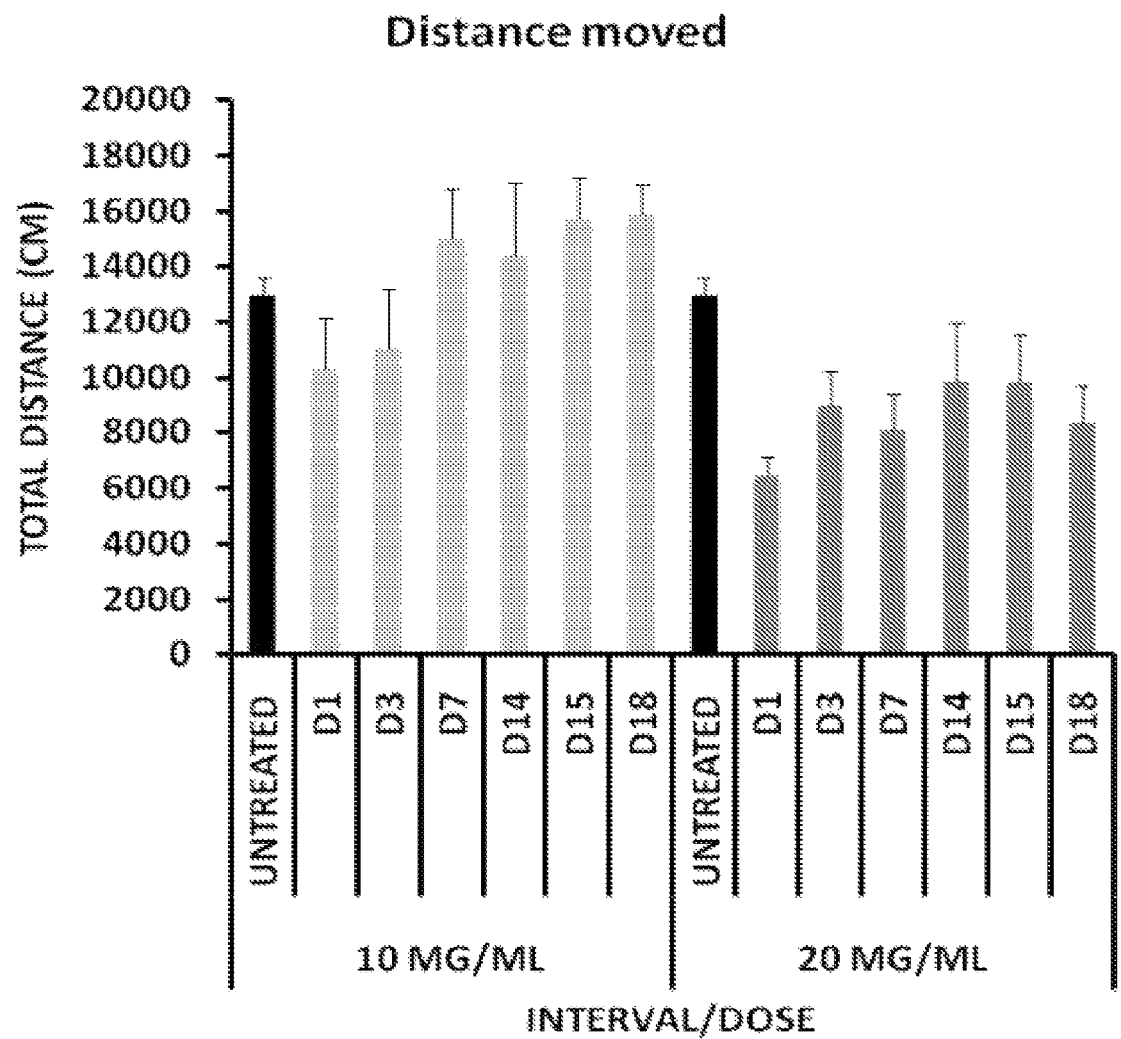
FIG. 4. Distance Moved by ckr Mice Treated with CM100 in Spontaneous Open Field Assays.
Figure 5:
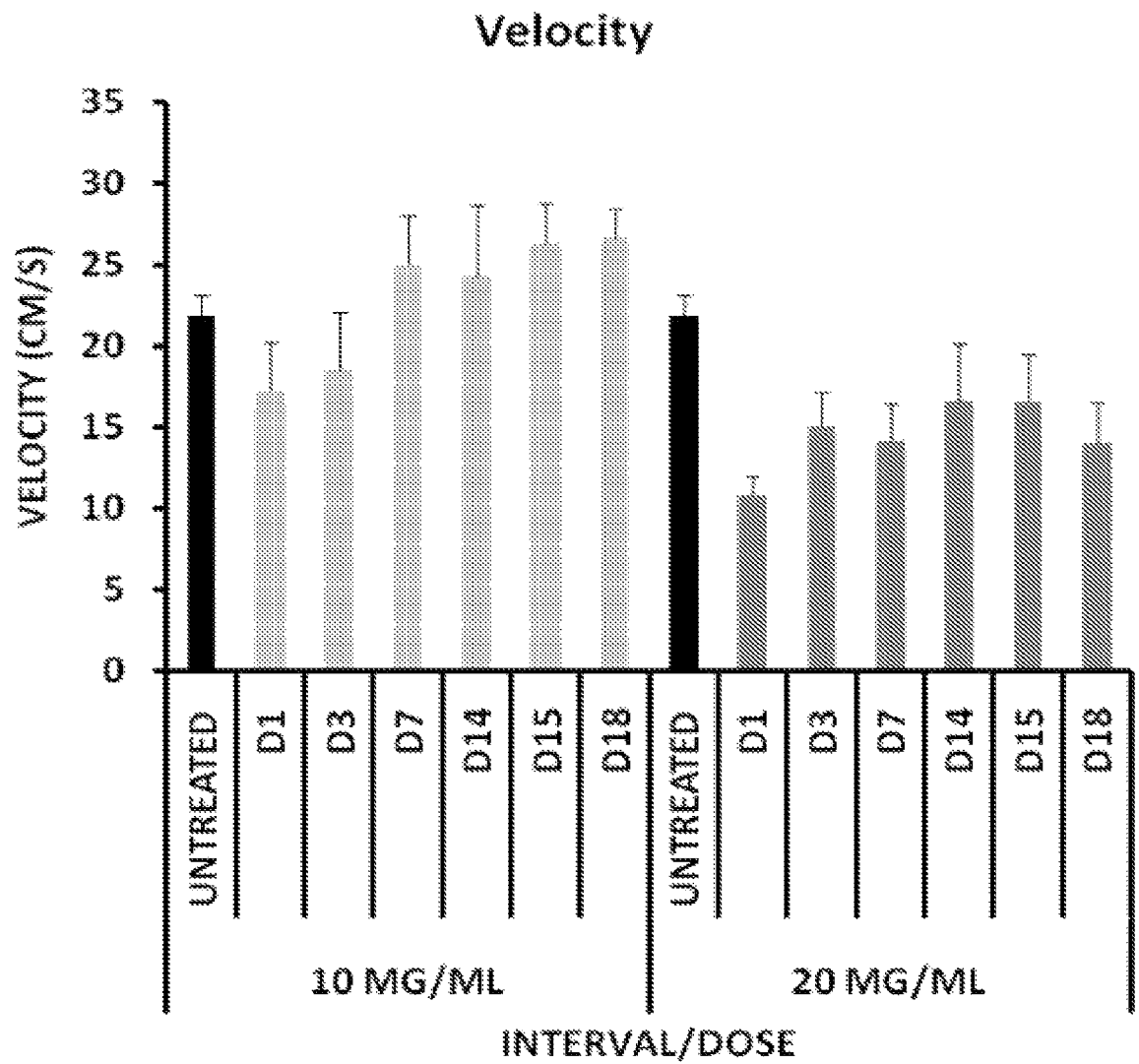
FIG. 5. Velocity of ckr Mice Treated with CM100 in Spontaneous Open Field Assays.

Provided herein are methods of treating disorders relating to Neuropsychiatric Disorders and methods of diagnosing the likelihood of having or developing a Neuropsychiatric Disorder.

Antipsychotic drugs are divided into two categories: "typical" antipsychotics and the newer "atypical" antipsychotics. Typical antipsychotics have been shunned in recent times due to their side effect profile which includes the production of extrapyramidal symptoms such a facial tics, gait disturbances, proprioceptive difficulties, rigidity, persistent muscle spasms, shakiness, restlessness, jitteriness and uncharacteristic movements.

Examples of antipsychotic drugs which fall into the "typical" category are: chlorpromazine, fluphenazine, haloperidol, loxapine, mesoridazine, molindone, perphenazine, pimozide, prochlorperazine, thiothixene, thioridazine and trifluoperazine.

With the advent of atypical antipsychotic drugs and their potential for enhanced efficacy and safety, the risk/benefit profile of this drug class has changed. Following the re-introduction of the first atypical antipsychotic, clozapine, in 1990, several new atypical drugs have become available for clinical use and now comprise more than 50% of the antipsychotic drug market in the United States. These drugs include risperidone (1994), olanzapine (1996) and quetiapine (1997).

Examples of "atypical" antipsychotic drugs are: aripiprazole, asenapine, clozapine, iloperidone, lurasidone, olanzapine, paliperidone, quetiapine, risperidone and ziprasidone among others.

Recent research has provided strong evidence of the efficacy of atypicals in Schizophrenia, and demonstrated that they greatly reduce the risk of extrapyramidal side effects, as well as reducing tardive dyskinesias. "Dyskinesias" are repetitive, uncontrollable and purposeless movements of the body or face. "Tardive" refers to those symptoms that develop after long-term antipsychotic treatment (several years). Unlike early dyskinesia symptoms, tardive dyskinesias may become permanent even if the antipsychotic medication is stopped.

These "atypical" antipsychotics are not without their side effects. While they have largely replaced the older medications, atypicals are rather expensive and carry a significant risk of weight gain (sometimes extreme weight gain) and diabetes. However, they may be more effective than the "typical" antipsychotics for such conditions as Schizophrenia, and other Schizoaffective Disorders as well as for multiple types of depression and other mental illnesses.

Although the antipsychotics were first developed for Schizophrenia, antipsychotic drugs are now broadly used for other disorders, including behavioral signs and symptoms associated with Alzheimer's disease, Dementias, depression, and are generally applied to the entire classes of Neuropsychiatric Disorders including: Adjustment Disorders, Anxiety Disorders, Dissociative Disorders, Eating Disorders, Impulse-Control Disorders, Mood Disorders, Sexual Disorders, Sleep Disorders, Psychotic Disorders, Sexual Disorders, Somatoform Disorders, Substance abuse disorders, and Personality Disorders. Despite their widespread use in these conditions, the overall effectiveness and safety of these drugs remain unclear.

Neurological and Neuropsychiatric Disorders

In accordance with the present disclosure, a method is presented for alleviating symptoms of neurological disorders. In one embodiment, the method comprises administering to an individual a digestive enzyme either naturally or recombinantly derived, or their derivatives in an amount effective to reduce the symptoms of the neurological disorders.

There are over 300 Neuropsychiatric Disorders listed in the DSM-IV and there is overlap among the different diagnoses. Neuropsychiatric Disorders are categorized according to their predominant features. For example, phobias, social anxiety and post-traumatic stress disorder all include anxiety as a main feature of the disorder. Schizophrenia and related disorders such as delusional disorder, brief psychotic disorder, Schizoaffective Disorder, Schizophreniform Disorder and shared psychotic disorder (a disorder that is characterized by the individual's inability to determine real from unreal), share similar characteristics.

In one embodiment, the neurological disorders that present symptoms potentially suitable for alleviation according to the present method include, but are not limited to the following disorders and categories of disorders: Adjustment Disorders, Addiction, Alzheimer's Disease, Anxiety Disorders, Bipolar Disorder, Cognitive Disorders, Dementias, Dissociative Disorders, Eating Disorders, Impulse-Control Disorders, Mood Disorders, Sexual Disorders, Sleep Disorders, Psychotic Disorders such as Schizophrenic Disorders (e.g., Schizophrenia), Somatoform Disorders, Substance Abuse Disorders and Personality Disorders.

As used herein, a Schizophreniform Disorder, refers to a psychotic disorder characterized by distortions of reality and disturbances of thought and language and withdrawal from social contact.

Examples of anxiety conditions which are treated using the method of this disclosure include but are not limited to Anxiety Disorders, panic disorder, panic disorder with agoraphobia, panic disorder without agoraphobia, agoraphobia without history of panic disorders, social phobia, simple phobia, obsessive compulsive disorder, post-traumatic stress disorder, generalized anxiety disorder, anxiety disorder-not otherwise specified (NOS), organic anxiety disorder, psychoactive substance anxiety disorder, separation anxiety disorder, avoidant disorder of childhood or adolescence, and overanxious disorder.

Examples of neuropsychiatric conditions which are treated using the method of this disclosure include, but are not limited to, Schizophrenia, catatonic, subchronic; Schizophrenia, catatonic, chronic; Schizophrenia, catatonic, subchronic with acute exacerbation; Schizophrenia, catatonic, chronic with acute exacerbation; Schizophrenia, catatonic, in remission; Schizophrenia, catatonic, unspecified; Schizophrenia, disorganized, subchronic; Schizophrenia, disorganized, chronic; Schizophrenia, disorganized, subchronic with acute exacerbation; Schizophrenia, disorganized, chronic with acute exacerbation; Schizophrenia, disorganized, in remission; Schizophrenia, disorganized, unspecified Schizophrenia, paranoid, subchronic; Schizophrenia, paranoid, chronic; Schizophrenia, paranoid, subchronic with acute exacerbation; Schizophrenia, paranoid, chronic with acute exacerbation; Schizophrenia, paranoid, in remission; Schizophrenia, paranoid, unspecified; Schizophrenia, undifferentiated, subchronic; Schizophrenia, undifferentiated, chronic; Schizophrenia, undifferentiated, sub chronic with acute exacerbation; Schizophrenia, undifferentiated, chronic with acute exacerbation; Schizophrenia, undifferentiated, in remission; Schizophrenia, undifferentiated, unspecified; Schizophrenia, residual, subchronic; Schizophrenia, residual, chronic; Schizophrenia, residual, subchronic with acute exacerbation; Schizophrenia, residual, chronic with acute exacerbation; Schizophrenia, residual, in remission; Schizophrenia, residual, unspecified; delusional (paranoid) disorder; brief reactive psychosis; Schizophreniform Disorder; Schizoaffective Disorder; Personality Disorders, schizoid; and Personality Disorders, schizotypal. In one embodiment, clinical features or symptoms of Schizophrenia include positive symptoms, which include but are not limited to psychosis, hallucinations, delusions, disorganized thought, disorganized speech (e.g., frequent derailment or incoherence), movement disorders, and bizarre behavior. Delusions include but are not limited to false beliefs that significantly hinder a person's ability to function. For example, an individual may have the delusion that people are trying to hurt them when there is no evidence of this, or the individual having the delusion that they are somebody else. Hallucinations include false perceptions. Hallucinations may be visual (e.g., seeing things that are not there), auditory (e.g., hearing things that are not there), olfactory (e.g., smelling things that are not there), tactile (e.g., feeling sensations on the skin that are not there, such as the feeling of bugs crawling on the skin), or gustatory. Auditory hallucinations and paranoia about others reading their minds, or being able to be in their bodies are examples of symptoms experienced by schizophrenics. These symptoms appear to express an excess or distortion of normal function. Psychosis as used herein generally refers to an abnormal condition of the mind, and is a term for a mental state that may be described as a "loss of contact with reality" that is observed, in some cases, in patients with Schizophrenia. Psychosis is given to the more severe forms of psychiatric disorder, during which hallucinations and delusions and impaired insight may occur.

In another embodiment, clinical features or symptoms of Schizophrenia include negative symptoms, which include but are not limited to loss of motivation, restricted range of emotional experience and expression, reduced hedonic capacity, affective flattening, alogia, and avolition. Negative symptoms such as "flat affect", lack of enjoyment, restricted communication and inability to follow through on planned activities, losing interest in everyday activities such as bathing, grooming, or getting dressed; feeling out of touch with other people, family, or friends; a lack of feeling or emotion (apathy); having little emotion or inappropriate feelings in certain situations; and having less ability to experience pleasure may be experienced. These reflect symptoms that appear to express a loss or diminution of normal function.

In yet another embodiment, clinical features or symptoms of Schizophrenia include one or more symptoms of cognitive impairment. For example, cognitive impairment symptoms include poor executive function, inability to use learned information, and difficulty paying attention and/or focusing.

Individuals with Neuropsychiatric Disorders frequently exhibit one or more characteristics of the particular disorder. Additionally, these characteristics often overlap with symptoms of other disorders within the category of neurological disorders as well as other disorders characterized as mental illness such as, but not limited to, Alzheimer's Disease and Bipolar Disorder. The present disclosure contemplates that one or more symptoms as well as a complete constellation of symptoms within one individual may be alleviated by the present method.

Recognition and determination of a reduction in symptoms of any and all of these disorders can be readily performed by those skilled in the art. One will recognize that these psychotic conditions are characterized by hallucinations, delusions or grossly disorganized behavior, which indicates that the patient suffers from gross impairment in reality.

In another embodiment, a patient treated with such methods exhibits an improvement in one or more symptoms of at least about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% or about 100% compared to a patient treated with a control substance.

A "patient" to be treated by a method described herein refers to an adult or a child. In one embodiment, a patient to be treated is a human from about 2 and about 10 years of age, from about 11 to about 20 years of age, or from about 21 to about 30 years of age.

Diagnosis

The recognition of the symptoms of the Neuropsychiatric Disorder or disorders present in an individual and determination that the present method may alleviate said symptoms prior to, during, or after the practice of this method is well within the purview of an individual ordinarily skilled in the art, who can perform suitable clinical, diagnostic, and or observational or other techniques required.

The DSM IV Diagnostic Criteria for Schizophrenia is described below:

A. Characteristic Symptoms:

Two (or more) of the following, each present for a significant portion of time during a 1-month period (or less if successfully treated): delusions, hallucinations, disorganized speech (e.g., frequent derailment or incoherence), grossly disorganized or catatonic behavior, negative symptoms, i.e., affective flattening, alogia, or avolition. Only one Criterion A symptom is required if delusions are bizarre or hallucinations consist of a voice keeping up a running commentary on the person's behavior or thoughts, or two or more voices conversing with each other.

B. Social/Occupational Dysfunction:

For a significant portion of the time since the onset of the disturbance, one or more major areas of functioning such as work, interpersonal relations, or self-care are markedly below the level achieved prior to the onset (or when the onset is in childhood or adolescence, failure to achieve expected level of interpersonal, academic, or occupational achievement).

C. Duration:

Continuous signs of the disturbance persist for at least 6 months. This 6-month period must include at least 1 month of symptoms (or less if successfully treated) that meet Criterion A (i.e., active-phase symptoms) and may include periods of prodromal or residual symptoms. During these prodromal or residual periods, the signs of the disturbance may be manifested by only negative symptoms or two or more symptoms listed in Criterion A present in an attenuated form (e.g., odd beliefs, unusual perceptual experiences).

Compositions and Formulations

Digestive enzymes are produced by the salivary glands, glands in the stomach, the pancreas and glands in the small intestines. Digestive enzymes produced by the pancreas are secreted into the duodenum, or upper segment of the small intestine, raising the pH to around 5 or 6, and they assist in the digestion of food components, including carbohydrates, lipids, proteins and nucleic acids.

Digestive enzymes have been administered to mammals to treat enzyme deficiencies caused by conditions affecting the pancreas, such as pancreatitis and pancreatic enzyme deficiency. Pancreatic enzymes administered to humans are commonly of porcine origin. Individuals with cystic fibrosis require the administration of enzymes, particularly lipases, in the maintenance of their condition. Manufacturers of enzyme preparations for these individuals have used enteric coatings for targeted delivery in the distal section of the small intestine, where lipase activity is important.

In another aspect, this disclosure relates to a pharmaceutical composition comprising a therapeutically effective amount of an enzyme preparation, which comprises a core amount of pancreatic or digestive enzymes effective for treating a subject susceptible to treatment by the enzymes, specifically those suffering with Neuropsychiatric Disorders.

In another aspect, this disclosure relates to a pharmaceutical composition comprising a therapeutically effective amount of an enzyme preparation, which comprises a core amount of pancreatic or digestive enzymes effective for treating a subject susceptible to treatment by the enzymes, specifically those suffering with Schizophrenia.

In another aspect, this disclosure relates to a pharmaceutical composition comprising a therapeutically effective amount of an enzyme preparation, which comprises a core amount of pancreatic or digestive enzymes effective for treating a subject susceptible to treatment by the enzymes, specifically those suffering with psychosis.

In one embodiment of the present disclosure, digestive enzymes comprise proteases, amylases and lipases, as well as other proteins secreted in a mammal that affect the digestive process either directly or indirectly. In one aspect, digestive enzymes present in the composition include an amylase, a protease, or a lipase.

In another aspect, digestive enzymes present in the composition include two or more of: an amylase, a protease, and a lipase.

In one aspect, digestive enzymes present in the composition include an amylase, a protease, and a lipase.

In another aspect, a composition may further contain one or more of cellulase, *papaya*, bromelain, chymotrypsin, and trypsin.

In one embodiment, the digestive or pancreatic enzyme composition comprises one or more of the following: amylases, proteases, cellulase, *papaya*, bromelain, lipases, chymotrypsin, and trypsin.

Compositions may contain an amount of protease from about 5,000 to about 1,500,000 U.S.P. units/dose including, but not limited to about 5,000; about 7,500; about 10,000; about 15,000; about 20,000; about 25,000; about 30,000; about 40,000; about 50,000; about 65,000; about 75,000; about 100,000; about 140,000; about 140,400; about 150,000; about 200,000; about 250,000; about 300,000; about 350,000; about 400,000; about 450,000; about 465,000; about 500,000; about 550,000; about 600,000; about 650,000; about 700,000; about 750,000; about 800,000; about 850,000; about 900,000; about 950,000; about 1,000,000; about 1,050,000; about 1,100,000; about 1,150,000; about 1,200,000; about 1,250,000; about 1,300,000; about 1,350,000; about 1,400,000; about 1,450,000; and about 1,500,000 U.S.P. units/dose along with all values in between per dose.

Compositions may contain an amount of amylase from about 1,000 to about 15,000,000 U.S.P. units/dose including, but not limited to about 1,000; about 3,000; about 5,000; about 7,500; about 10,000; about 15,000; about 20,000; about 25,000; about 30,000; about 40,000; about 50,000; about 65,000; about 75,000; about 100,000; about 144,000; about 500,000; about 1,000,000; about 2,000,000; about 3,000,000; about 4,000,000; about 5,000,000; about 6,000,000; about 7,000,000; about 8,000,000; about 9,000,000; about 10,000,000; about 11,000,000; about 12,000,000; about 13,000,000; about 14,000,000; and about 15,000,000 U.S.P. units/dose, along with all values in-between per dose.

Compositions may contain an amount of lipase from about 1,500 to about 282,000 U.S.P. units/dose including, but not limited to, about 1,500; about 1,880; about 2,000; about 3,000; about 5,000; about 7,500; about 10,000; about 15,000; about 20,000; about 23,000; about 23,040; about 25,000; about 30,000; about 40,000; about 50,000; about 65,000; about 75,000; about 100,000; about 125,000; about 150,000; about 200,000; about 250,000; and about 282,000 U.S.P. units/dose, along with all values in-between per dose.

In another embodiment, the digestive enzyme composition is comprised of protease, lipase, and amylase where the activities are: protease between 10,000 to 1,500,000 U.S.P. units/dose including 10,000; 100,000; 150,000; 200,000; 250,000; 300,000; 350,000; 400,000; 450,000; about 465,000; 500,000; 550,000; 600,000; 650,000; 700,000; 750,000; 800,000; 850,000; 900,000; 950,000; 1,000,000; 1,050,000; 1,100,000; 1,150,000; 1,200,000; 1,250,000; 1,300,000; 1,350,000; 1,400,000; 1,450,000; and 1,500,000 U.S.P. units/dose, along with all values in between per dose and where the ratio of protease to lipase is such that the amount of lipase is never more than 0.188 times the amount of protease and where the ratio of protease activity to amylase activity is between 1:0.1 and 1:10.

In another embodiment a pharmaceutical composition comprises about 23,000 U.S.P. units/dose of lipase, about 144,000 U.S.P. units/dose of amylase, and about 140,000 U.S.P. units/dose of protease. In another embodiment a pharmaceutical composition contains about 23,040 U.S.P. units/dose of lipase, about 144,000 U.S.P. units/dose of amylase, and about 140,400 U.S.P. units/dose of protease.

In some embodiments, the digestive enzyme composition comprises at least one protease and at least one lipase, wherein the ratio of total proteases to total lipases (in U.S.P. units) ranges from about 5.371:1 to about 20:1 including 5.371:1, 6:1, 7:1, 8:1, 9:1, 10:1, 11:1, 12:1, 13:1, 14:1, 15:1, 16:1, 17:1, 18:1, 19:1, and 20:1, along with all values in-between. In some embodiments, the ratio of proteases to lipases ranges from about 5.371:1 to about 10:1 including 5.371:1, 6:1, 7:1, 8:1, 9:1, and 10:1, along with all values in-between.

In yet another embodiment, the digestive enzyme composition comprises at least one protease and at least one lipase, wherein the ratio of total proteases to total lipases (in U.S.P. units/dose) ranges from about 5.371:1 to about 20:1 including 5.371:1, 6:1, 7.1, 8.1, 9:1, 10:1, 11:1, 12:1, 13:1, 14:1, 15:1, 16:1, 17:1, 18:1, 19:1, and 20:1, along with all values in-between. In another embodiment, the digestive enzyme composition comprises at least one protease and at least one lipase, wherein the ratio of total proteases to total lipases (in U.S.P. units/dose) ranges from about 1:1 to about 20:1. In yet another embodiment, the ratio of proteases to lipases ranges from about 4:1 to about 10:1. In one embodiment, the ratio of proteases to lipases ranges from about 5.371:1 to about 10:1 including 5.371:1, 6:1, 7:1, 8:1, 9:1, and 10:1 along with all values in-between. In one embodiment, the digestive enzyme composition comprises at least one protease and at least one amylase, wherein the ratio of total proteases to total amylases (in U.S.P. units/dose) ranges from about 1:0.1 to about 1:10 including 1:0.25, 1:0.5, 1:0.75, 1:1, 1:1.25, 1:1.5, 1:1.75: 1:2, 1:1.25, 1:1.5, 1:1.75, 1:1.2, 1:1.25, 1:1.5, 1:1.75, 1:1.2, 1:1.25, 1:1.5, 1:1.75, 1:1.2: 1:1.5, 1:2, 1:3, 1:4, 1:5, 1:6, 1:7, 1:8, 1.9, and 1:10 along with all values in-between.

The disclosure also relates to a specific blend of enzymes, with or without coating, with or without other components as described above whereby enzyme administration occurs in individuals with a neurological or Neuropsychiatric Disorder, including but not limited to: Adjustment Disorders, Addiction, Alzheimer's Disease, Anxiety Disorders, Bipolar Disorder, Cognitive Disorders, Dementias, Dissociative Disorders, Eating Disorders, Impulse-Control Disorders, Mood Disorders, Sexual Disorders, Sleep Disorders, Psychotic Disorders such as Schizophrenic Disorders (e.g., Schizophrenia), Somatoform Disorders, Substance Abuse Disorders and Personality Disorders. Recognition and determination of a reduction of symptoms of any and all of these disorders can be readily performed by those skilled in the art using conventional assays.

In one embodiment of the present disclosure, uncoated digestive enzymes comprise proteases, amylases and lipases, as well as other proteins secreted in a mammal, which affect the digestive process either directly or indirectly. In one embodiment, the digestive or pancreatic enzyme composition comprises one or more of the following: amylases, proteases, cellulase, *papaya*, bromelain, lipases, chymotrypsin, and trypsin.

In one embodiment the coated or uncoated digestive enzymes to be administered are comprised of pancreatin, pancrelipase, or a combination thereof. In one embodiment a coating technology can be used, such as the ones described in U.S. Pat. Nos. 6,835,397, 6,153,236, or US 2009-0004285 which are herein incorporated by reference in their entirety.

Enzyme preparations with non-lipid enteric coatings can be used to deliver lipases in individuals in need of lipase administration. Certain methods and enzyme compositions for use in treating children and other individuals in, for example, U.S. Pat. Nos. 7,138,123, 6,660,831, 6,632,429, 6,534,063, which is herein incorporated by reference in its entirety.

The composition of the dosage form may include other components, generally utilized in pharmaceutical preparations including but not limited to binders, disintegrants, extracts, lubricants, fillers, flavorings, preservatives, colorants, taste maskers, diluents and coating agents, such as vegetable oil, crystalline oils, and other coating methodologies.

In one embodiment, coating of a digestive enzyme preparation is used to obtain release at selected transit times or in selected locations of the gastrointestinal tract of humans. In one aspect, this disclosure relates to controlled release enzyme preparations administered to an individual with a Neuropsychiatric Disorder.

In yet another aspect, this disclosure relates to an enzyme delivery system comprising a coated enzyme preparation having particles which comprise: (a) a core comprising pancreatic or digestive enzymes present in an amount from about 5% to 99% by weight of the particles; and (b) a generally uniform coating to provide for controlled release of the enzymes, said coating comprising an emulsifiable lipid. In one aspect, the coated enzyme preparation particles of the enzyme delivery system are non-aerosolizable.

In some embodiments a coated digestive enzyme preparation comprising (a) a core containing a digestive enzyme particle, where the enzyme present in an amount of from about 5% to 95% by weight of the particles, including 5%, 10%, 15%, 20%, 25%, 30%, 35%, 40%, 45%, 50%, 55%, 60%, 65%, 70%, 75%, 80%, 85%, 90% and 95% by weight, along with all values in-between; and (b) a coating comprising a crystallizable lipid, wherein the coating continuously coats the core and the crystallizable lipid releases the enzyme upon exposure to physiological conditions.

In some embodiments a coated enzyme preparation having particles which comprise: (a) a core comprising pancreatic or other digestive enzymes present in an amount of from about 5% to 95% by weight of the particles, including 5%, 10%, 15%, 20%, 25%, 30%, 35%, 40%, 45%, 50%, 55%, 60%, 65%, 70%, 75%, 80%, 85%, 90% and 95% by weight along with all values in-between; and (b) a generally uniform coating to provide for controlled release of the enzymes, the coating comprising a crystallizable lipid. In some embodiments, the coated enzyme preparation particles of the enzyme delivery system are non-aerosolizable.

The present disclosure also relates to methods of making the enzyme preparations by lipid coating and/or encapsulation of digestive enzymes. The methods comprise providing an emulsifiable lipid, and coating pancreatic/digestive enzyme particles with the lipid. The digestive enzymes comprise 5 to 99% of the coated enzyme preparations by weight.

In another aspect as described herein, the inventors have discovered that the methods of this disclosure produce coated digestive enzyme preparations comprising digestive and/or pancreatic enzymes coated with an emulsifiable lipid alone, or with a lipid blend to achieve a controlled rate of enzyme release, with increased release of the pancreatic/digestive enzyme upon exposure of the coated preparation to a suitable solvent. The inventors have discovered that coated pancreatic/digestive enzyme preparations having a coating consisting essentially of one or more monoglycerides exhibit time-sensitive biologically-suitable release of the pancreatic/digestive enzymes upon exposure of the coated composite to a solvent, such as water, while protecting against release in 0.1 N HCl or acidic gastric fluid.

The nature of the human digestive tract creates challenges for the delivery of digestive enzymes to patients susceptible to treatment with digestive enzymes. Multiple temperature and pH changes over the course of the digestive tract make specific delivery a challenge but a necessity. For instance, pH as low as 1 is encountered in the stomach, but rapidly increases to a more basic pH of 5-6 in the proximal small intestine. For example, generally the pH in the stomach is approximately 1.2, the pH in the duodenum is about 5.0 to 6.0; the pH in the jejunum is about 6.8, and the pH is about 7.2 in the proximal ileum and about 7.5 in the distal ileum. The low pH in the stomach that changes rapidly to a more basic pH of 5-6 in the proximal small intestines calls for a specific delivery method depending upon where the enzyme is to be delivered.

Delivery of digestive enzymes can also be challenging due to the rapid degradation and denaturing of enzymes at ambient room temperature, as well as the enhanced degradation and denaturing that can occur with high temperature, pressure, humidity and/or exposure to light. Moisture and heat together can quickly destabilize enzymes, reducing their effectiveness, and weaken their potency leading to inaccurate dosing and shortened shelf life. Denaturation or destabilization of the enzymes can reduce their effectiveness by reducing the dose of active enzymes to less than the amount needed for effective treatment. In one embodiment, to protect and stabilize the pancreatic/digestive enzyme from unfavorable conditions such as oxidation, the pancreatic/digestive enzyme (core) is coated or encapsulated in a continuous coating containing an emulsifiable lipid. In another aspect, this disclosure provides new coated enzyme preparations with improved shelf life.

Manufacturers of enzyme preparations have used enteric coatings to deliver lipases in individuals requiring administration of lipases, such as individuals with cystic fibrosis. Because the porcine enzymes are delivered in a mixture of proteases, lipases and amylases, and because these compositions for human consumption were prepared for lipase delivery, the uses of these enteric coatings, which include such substances as hypromellose phthalate, dimethicone 1000, and dibutyl phthalate, preclude delivery of proteases at the proper location for protein digestion, which is the duodenum. All other enzyme preparations presently on the market contain at least one of these enteric coating substances and/or other additives in the preparation.

In one embodiment the present disclosure includes a coated digestive enzyme preparation and/or composite, which in some embodiments is an encapsulated pancreatic/digestive enzyme preparation. In other aspects, the disclosure includes enzyme delivery systems and pharmaceutical compositions comprising coated pancreatic/digestive enzyme preparations. These coated or encapsulated enzyme preparations contain cores comprising pancreatic or digestive enzyme particles, and a coating comprising an emulsifiable lipid.

The coatings in the digestive/pancreatic enzyme preparations create a barrier to degradation and denaturation, and allow more accurate levels of active enzymes to be utilized by treated individuals. The lipid coating of this disclosure provides a significant barrier to moisture, humidity and exposure to light by allowing for a physical barrier as well as one that prevents and/or reduces hydrolysis. The coated enzyme preparations undergo less hydrolysis as a result of protection from moisture in the environment by the lipid coating. As a result of the present disclosure, pancreatic/digestive enzymes are provided which can tolerate storage conditions (e.g., moisture, heat, oxygen, etc.) for long periods of time thus enabling extended shelf life. The coating of the encapsulated enzyme preparation protects the enzyme from the environment and provides emulsification in a solvent without detracting from the abrasion resistance of the coating. The disclosure thus further relates to more stable enzyme preparations.

It is another aspect of the present disclosure to make an enzyme preparation without the use of extenders colorants, dyes, flow enhancers and other additives to reduce the potential for allergens and other sensitivity reactions in children and other treated individuals. It has been discovered that in some embodiments, the digestive enzymes can be encapsulated with a single lipid excipient to improve retention of enzyme activity, ease of administration, tolerability, and safety of administration, among other properties. Surprisingly, digestive enzyme particles containing lipases can be successfully encapsulated with coating consisting essentially of only hydrogenated soy oil.

Porcine pancreatic/digestive enzymes possess a significant odor and taste, similar to cured or smoked pork. This taste and smell can be strong and offensive to some individuals taking enzyme replacement, and especially to children. In one embodiment, the addition of a lipid coating provides significant odor and taste masking to the enzyme preparation, which allows for the tolerance of taste, as the lipid coating is odorless and tasteless. The use of this method of taste masking not involving the use of color, dyes, perfumes or other substances is preferable for the administration of medications, which have an unpleasant or undesirable taste and odor. In another embodiment, this disclosure relates to coated digestive enzyme preparations with improved taste and odor.

In some embodiments, the coatings on the digestive enzyme particle cores are preferably continuous coatings. By "continuous", it is meant that the pancreatic/digestive enzyme is completely surrounded. The continuous coating fully surrounds or encapsulates the pancreatic/digestive enzymes. The encapsulation provides protection of the pancreatic/digestive enzyme from conditions such as moisture and oxidation.

In the manufacture of pharmaceuticals, encapsulation refers to a range of techniques used to enclose medicines in a relatively stable shell known as a capsule, allowing them to, for example, be taken orally or be used as suppositories. "Encapsulate" as used herein means that the coating completely surrounds the pancreatic/digestive enzyme. A coated or encapsulated preparation may contain one or more digestive enzyme particles enveloped in one coating to form one coated or encapsulated digestive enzyme particle in the coated or encapsulated digestive enzyme preparation.

The two main types of capsules are hard-shelled capsules, which are normally used for dry, powdered ingredients, and soft-shelled capsules, primarily used for oils and for active ingredients that are dissolved or suspended in oil. Both of these classes of capsule are made both from gelatin and from plant-based gelling substances like carrageenans and modified forms of starch and cellulose, and the latter form is usually seamless. Capsules are made in two parts by dipping metal rods in molten gelatin solution. The capsules are supplied as closed units to the pharmaceutical manufacturer. Before use, the two halves are separated, the capsule is filled with powder (either by placing a compressed slug of powder into one half of the capsule, or by filling one half of the capsule with loose powder) and the other half of the capsule is pressed on. The advantage of inserting a slug of compressed powder is that control of weight variation is better, but the machinery involved is more complex.

Sprinkle capsules are a dosage form consisting of small beads or granules of an active drug contained in a capsule that can be readily administered by simply opening up the capsule and distributing the contents over something to be swallowed.

In addition, the encapsulation also provides controlled release of the pancreatic/digestive enzyme. In one embodiment, the emulsification properties of the coating in a solvent allows for controlled release of the enzyme in the gastrointestinal (GI) system, preferably the region of the GI tract where the enzymes are to be utilized. For example, for conditions requiring treatment with proteases, the release of the protease portion of the enzymes is necessary in the proximal small intestine, thereby necessitating a lipid encapsulation, which has a dissolution profile showing a release of between 10% to 100% of the active substance into solution over a time period of between 30 and 90 minutes. In one embodiment, the dissolution profile shows a release of about 20%, 30%, 40%, 50%, 60%, 70%, 80%, 90% or 100%, and all values in between, of the coated substance into solution over a time period of about 30, 35, 40, 45, 50, 55, 60, 65, 70, 75, 80, 85 or 90 minutes and all values in between. Dissolution profiles may be obtained using methods and conditions known to those of skill in the art. For example, dissolution profiles can be determined at various pHs, including pH 1, 2, 3, 4, 5, 6, 7, 8, 9, 10 and all values in between.

The rate of release of the bioactive substance can also be controlled by the addition of additives as described below. When the preparations are exposed to a solvent, the solvent interacts with the mollifiable lipid in the coating and results in emulsification of the coating and release of the bioactive substance.

A suspension is a heterogeneous fluid containing solid particles that are sufficiently large for sedimentation. Usually they must be larger than 1 micrometer. The internal phase (solid) is dispersed throughout the external phase (fluid) through mechanical agitation, with the use of certain excipients or suspending agents. Unlike colloids, suspensions will eventually settle. An example of a suspension would be sand in water. The suspended particles are visible under a microscope and will settle over time if left undisturbed. This distinguishes a suspension from a colloid in which the suspended particles are smaller and do not settle. Colloids and suspensions are different from a solution, in which the dissolved substance (solute) does not exist as a solid and solvent and solute are homogeneously mixed. Oftentimes, powders of active ingredients may be packaged such that the addition of a diluent dissolves the powder and holds it in a liquid suspension.

A pharmaceutical preparation may be prepared in which an excipient provides a matrix to capture and protect a product before delivery. Pharmaceutical preparations may be prepared whereby the individual who takes the preparation has a reduction in the number of capsules/tablets per dosage; i.e., the preparation is stabilized and may contain a therapeutically effective amount of a protease, an amylase, and/or a lipase. Preparations may include, for example, a stabilizing matrix consisting essentially of a solidified microcrystalline cellulose which captures and protects therapeutically effective amounts of digestive enzyme particles within the stabilizing matrix. This can be done, for example, through the use of what is known in the art as PROSOLV® technology.

PROSOLV® is a combination of excipients which allow for optimized flow, compaction and product uniformity. This technology allows for uniformity in this combination, as well as manufacturing a very small tablet which would be amenable for children. With PROSOLV® technology, the ingredients are not just blended, but are co-processed, which assures that equal particles are uniformly distributed and these results are easily reproducible. This allows for stability and superb product quality.

Whether utilizing the PROSOLV® method or other methodology, the one or more digestive enzymes will be formulated and manufactured such that the particles will be uniformly distributed and there will be no overage with respect to the amount of enzyme found in the preparation. Said new drug formulation can be found in, but is not limited to, formulations which include digestive/pancreatic enzymes with and without the utilization of the PROSOLV® technology.

In a further embodiment, a direct compression method may be used for the manufacture of a pharmaceutical tablet preparation including the steps of: (a) forming an active blend by blending an intimate admixture of silicified microcrystalline cellulose and a therapeutic agent comprising one or more digestive enzymes; (b) forming a color blend by blending an intimate admixture of one or more pharmaceutically acceptable dyes and silicified microcrystalline cellulose if color is necessary; (c) combining the active blend, the color blend and a disintegrant into a pre-blend; (d) adding a lubricant to the pre-blend to form a final blend; and (e) compressing the final blend to form a pharmaceutical tablet preparation or a mixture of time released microtabs or a time released tablet.

This may be accomplished by combining the digestive enzymes with one of the patented PROSOLV® technologies, i.e.: PROSOLV® SMCC 50 or PROSOLV® SMCC 90, or other PROSOLV® technologies. When employing the PROSOLV® method, the silicified microcrystalline cellulose (SMCC) used in the preparation of the present invention may be any commercially available combination of microcrystalline cellulose granulated with colloidal silicon dioxide. The SMCC generally will be as described in Sherwood et al, Pharm. Tech., October 1998, 78-88 and U.S. Pat. No. 5,585,115, which is incorporated herein by reference in its entirety. SMCC can be obtained commercially from Edward Mendell Company, Inc., a subsidiary of Penwest Ltd., under the name PROSOLV® SMCC. There are different grades of SMCC available, with particle size being the differentiating property among the grades. For example, PROSOLV® SMCC 90 has a median particle size, by sieve analysis, in the region of 90 micrometers. PROSOLV® SMCC 50 has a median particle size, by sieve analysis, in the region of about 40-50 micrometers.

A pharmaceutical composition described herein may be prepared using a direct compression method, a dry granulation method, or by wet granulation. Preferably, the digestive/pancreatic enzyme preparation may be prepared using a direct compression process. This preferred process consists of two main steps: blending and compression.

The blending step is composed of an active blend, color blend, pre-blend, and final blend (lubrication). The formulation of the present invention may include a number of other ingredients for optimal characteristics of the pharmaceutical composition. Such other ingredients and the amounts to be used are within the knowledge of one in the art and are known in the pharmaceutical arts. These may include disintegrates, lubricants and/or coloring agents among others. Suitable disintegrants include, for example, sodium starch glycolate, other starches such as pregelatinized starch, and celluloses. Suitable lubricants may be provided, such as magnesium stearate, calcium stearate, talc and stearic acid. Any coloring agent certified by the FDA may be used, such as FD&C Yellow #6, among others.

When used as a pharmaceutical preparation, elixirs contain an active ingredient that is dissolved in a solution that contains some percentage (usually 40-60%) of ethyl alcohol and is designed to be taken orally.

Syrups are oftentimes employed as a base for medicinal purposes and consist of a concentrated or saturated solution of refined sugar in distilled water.

A suspension of liquid droplets or fine solid particles in a gas is called an aerosol. This can take the form of an oral spray.

A gum may be devised whereby an active ingredient is incorporated into a vegetative resinous substance (e.g., acacia) and released via the actual mechanical effect of chewing or the action of saliva on the gum itself.

A thinstrip is an active pharmaceutical product coated by a lipid layer designed to dissolve in the mouth over a brief period of time. The same technology could be used to produce a medicated lollipop for transmucosal delivery.

In pharmaceutical terms, a granule is a small particle gathered into a larger, permanent aggregate in which the original particles can still be identified.

In some aspects, the disclosure relates to the production of selected coated enzyme preparations made by coating digestive enzyme particles with lipids not previously used in coated digestive enzyme preparations. The unique mixtures of emulsifiable lipids and enzymes can deliver certain components of the pancreatic/digestive enzymes to selected locations and/or at selected times during transit of the GI tract. In some aspects, the disclosure relates to methods of delivering digestive enzymes to humans based upon dissolution profiles.

The emulsifiable lipid may be any lipid, lipid mixture, or blend of lipid and emulsifiers which emulsifies when exposed to a solvent, and has a melting point which allows the lipid to be a solid at typical storage temperatures. The emulsifiable lipid can be a vegetable or animal derived-lipid. In another embodiment, the emulsifiable lipid consists essentially of, or comprises one or more monoglycerides, diglycerides or triglycerides, or other components including, for example, emulsifiers found in hydrogenated vegetable oils. In another embodiment the lipid is a non-polar lipid.

As used herein, animal and/or vegetable "derived" lipids can include fats and oils originating from plant or animal sources and/or tissues, and/or synthetically produced based on the structures of fats and oils originating from plant or animal sources. Lipid material may be refined, extracted or purified by known chemical or mechanical processes. The lipid may, in one embodiment, comprise a Type I U.S.P.-National Formulary vegetable oil.

The digestive enzyme used in the present disclosure can be any combination of digestive enzymes of a type produced by the pancreas, including, but not limited to digestive enzymes from a pancreatic source or other sources. The scope of the disclosure is not limited to pancreatic enzymes of porcine origin, but can be of other animal or plant origin as well as those that are synthetically derived. In one embodiment, the digestive enzyme is derived from mammalian sources such as porcine-derived digestive enzymes. In another embodiment, the enzyme includes one or more enzymes, and is plant derived, synthetically derived, recombinantly produced in microbial, yeast, or mammalian cells, or includes a mixture of enzymes from one or more sources. For example, digestive enzymes may include one or more enzymes from one or more sources mixed together. This includes, for example, the addition of single digestive enzymes to digestive enzymes derived from pancreatic sources in order to provide appropriate levels of specific enzymes that provide more effective treatment for a selected disease or condition. One source of digestive enzymes can be obtained, for example, from Scientific Protein Laboratories. In one embodiment, the digestive enzyme is, for example a pancreatin/pancrelipase composition. In another embodiment, the digestive enzymes comprise or consist essentially of 25 U.S.P. units protease, 2 U.S.P. units lipase, and 25 U.S.P. units amylase per milligram. The term digestive enzyme may refer to one or more enzymes of a type produced by the pancreas.

In one embodiment, the digestive enzyme used present as consisting of particles having various sizes. In another embodiment, the particles of digestive enzyme are screened to obtain particles of a suitable size for encapsulation by removing particles that are too fine or too large. For example, the particles may be sieved to obtain particles of a suitable size or more uniform size range for encapsulation.

In one embodiment, the minimum amount of pancreatic enzyme present in the core is at least about 5% active enzymes by weight of the coated enzyme preparation, but in another embodiment is at least about 30%, or at least about 50% by weight. In one embodiment, the maximum amount of pancreatic/digestive enzyme present in the composite is at most about 99% by weight, and in another embodiment is at most about 98%, 95%, 90%, 85%, 80%, 75% or 70% of the coated enzyme preparation. In another embodiment, the amount of pancreatic enzyme present in the composite is about 10%, 15%, 20%, 25%, 35%, 40%, 45%, 55%, 60%, 65%, 70%, 72.5%, 75%, 77.5%, 80%, 82.5%, 87.5%, or 92.5% by weight or anywhere in between. At least about or at most about a % of enzyme may include equal to or about that % of enzyme. The term "about" includes equal to, and a range that takes into account experimental error in a given measurement. As used in connection with particle sizes, the term "about" can refer to plus or minus 10, 9, 8, 7, 6, 5, 4, 3, 2 or 1% or anywhere in between. As used in connection with % particles that can be sieved, the term "about" can refer to plus or minus 10, 9, 8, 7, 6, 5, 4, 3, 2 or 1% or anywhere in between.

In one embodiment, the composition which contains the encapsulated digestive enzyme preparation or composite is delivered as a sprinkle, powder, capsule, tablet, pellet, caplet or other oral form. In another embodiment, packaging the encapsulated enzyme preparations in an enzyme delivery system that further comprises single dose sachet-housed sprinkle preparations allows for ease of delivery and accurate dosing of the enzyme by allowing a specific amount of enzyme to be delivered in each dosing. Allowing for specific unit dosing of an enzyme preparation which maintains the enzyme activity within specific stability parameters is an enhancement over other sprinkle formulations, which are housed in a multi-unit dosing form that allows for air, moisture and heat to deprecate and denature the enzyme preparation. In one embodiment, the powder or sachet is housed in a trilaminar pouch of which one layer is foil, or similar barrier to keep out moisture and to protect the enzyme preparation from adverse environmental factors. The disclosure further relates to an improvement in stability due to a reduction in hydrolysis due to the lipid encapsulation and composition of package.

In another embodiment, the lipid encapsulation methodology reduces the aerosolization of the enzyme preparation that may be caustic to the patient if inhaled. In another embodiment, the disclosure includes delivery of digestive enzymes with improved safety of administration, by reducing the amount of aerosolization of the enzyme. The lipid encapsulation reduces aerosolization and the potential for caustic burn, aspiration, and/or aspiration pneumonias in patients and administrators of the enzyme preparation, thereby reducing the potential for illness in already compromised children such as those with cystic fibrosis, and leading to safer administration.

As used herein, the term "non-aerosolizable" will be used to refer to a coated or encapsulated enzyme preparation where substantially all of the particles are large enough to eliminate or reduce aerosolization upon pouring of the coated enzyme preparation compared to uncoated enzyme particles.

As described and referred to herein, suitable pancreatic/digestive enzymes and suitable coatings may be used in the compositions and methods of this disclosure. The choice of suitable enzymes and of suitable lipid coatings, including choice of the type or amount of enzymes or coating, are guided by the specific enzyme needs of the individuals, and the selected diseases to be treated. The encapsulated enzyme preparations that are one aspect of this disclosure have not been previously described.

In another embodiment, the disclosure relates to a method of controlling the rate of release of the pancreatic/digestive enzyme from an encapsulated enzyme preparation upon exposure to a solvent. In one aspect, the method comprises blending an emulsifiable lipid with an amount of one or more additives to obtain a lipid blend and coating the digestive enzyme particle with the blend to form an encapsulated digestive enzyme preparation containing particles comprising a core which contains the enzyme, and a coating which contains the lipid. In one embodiment, the emulsifiable lipid is a blend where the emulsifiable lipid and additive are not the same, and where the rate of release of the enzyme from the encapsulated composite upon exposure to a solvent is decreased as the amount of additive is increased. In the alternative, the rate of release of the enzyme from the encapsulated composite upon exposure to a solvent is increased as the amount of additive is decreased.

The lipid coating surprisingly does not appear to be reduced or destroyed by hydrochloric acid (HCl) present in the stomach, thereby protecting the enzyme from degradation following administration until the enzyme preparation reaches its target region in the GI tract. Further the lipid coat reduces the exposure of the enzyme to attack by water, thereby reducing hydrolysis, and further protecting the digestive enzymes from degradation. In addition, the inventors have found that an excipient containing only lipid can be used to coat or encapsulate digestive enzyme particles containing lipase.

Enzyme preparations supplied by the API supplier may be provided as irregular shaped, and multi-sized particles, with uneven edges, and much clumping, and containing some crystalline salt particles. Uneven particle size and shape reduces flow properties, and interferes with packaging. In addition, pouring uncoated enzyme into the mouth of an individual would be difficult, and potentially may cause too much or too little of the enzyme to be delivered. In one embodiment, processing the digestive enzyme particles according to methods in accordance with one aspect of this disclosure yields a non-dusty, free-flowing particulate preparation suitable for sachet packaging and for pouring onto food or drink. In addition, as discussed throughout, the use of lipid encapsulation to prevent aerosolization and, therefore, increase safety, and to increase flow properties which enhance manufacturing of a pharmaceutical is an embodiment of the instant disclosure.

"Emulsifiable lipids" as used herein means those lipids that contain at least one hydrophilic group and at least one hydrophobic group, and have a structure capable of forming a hydrophilic and hydrophobic interface. These chemical and/or physical properties, mentioned above of an emulsifiable lipid permit emulsification. Examples of interfaces include, for example, micelles and bilayers. The hydrophilic group can be a polar group and can be charged or uncharged.

In one embodiment, the emulsifiable lipid is derived from animal or vegetable origins, such as, for example, palm kernel oil, soybean oil, cottonseed oil, canola oil, and poultry fat, including hydrogenated type I vegetable oils. In one embodiment, the lipid is hydrogenated. In another embodiment, the lipid is saturated or partially saturated. Examples of emulsifiable lipids include, but are not limited to, monoglycerides, diglycerides, fatty acids, esters of fatty acids, phospholipids, salts thereof, and combinations thereof.

The emulsifiable lipid is preferably a food grade emulsifiable lipid. Some examples of food grade emulsifiable lipids include sorbitan monostearates, sorbitan tristearates and calcium stearoyl lactylates. Examples of food grade fatty acid esters which are emulsifiable lipids include acetic acid esters of mono- and diglycerides, citric acid esters of mono- and di-glycerides, lactic acid esters of mono- and digylcerides, polyglycerol esters of fatty acids, propylene glycol esters of fatty acids, and diacetyl tartaric acid esters of mono- and diglycerides. Lipids can include, for example, hydrogenated soy oil. Any emulsifiable lipid may be used in the methods and products of this disclosure. In one embodiment, the emulsifiable lipid used will produce non-agglomerating, non-aerosolizing enzyme preparation particles.

In another embodiment, the method relates to preparation of an encapsulated, controlled release digestive enzyme preparation with enhanced flow properties useful in the treatment of individuals with a neurological or Neuropsychiatric Disorder, the method comprising: a) blending an emulsifiable lipid with one or more additives to obtain a blend; and b) coating screened digestive enzyme with the blend to form an encapsulated digestive enzyme containing a core which contains the digestive enzyme and a coating which contains the blend of emulsifiable lipid.

The coating of the enzyme with the lipid allows for the enzyme to become more uniform in size and shape, but reduces the jagged edges associated with the raw enzyme, and allows for ease of administration and ease of packaging, as the flow properties associated with the covered enzyme will allow for the packaging machinery to easily fill the sachet/pouch with the enzyme and reduces overfilling or underfilling of the sachet.

In another embodiment, the disclosure relates to a method of controlling the rate of release of a digestive enzyme from the encapsulated preparation by using a lipid blend to coat the digestive enzyme. The method includes blending an emulsifiable lipid with one or more additives to obtain a blend, and coating the digestive enzyme with the blend to form an encapsulated digestive enzyme containing a core which contains the digestive enzyme and a coating which contains the blend of emulsifiable lipid. The rate of release of the enzyme from the encapsulated preparation upon exposure with a solvent is decreased as the amount of additive is increased. In the alternative, the rate of release of the enzyme from the encapsulated composite upon exposure with a solvent is increased as the amount of additive is decreased. Thus, the nature of the coating allows for controlled release of the enzyme from the encapsulate.

Different dosage forms have different benefits. Tablets and capsules are the most common dosage forms for oral administration due to ease of manufacture, packaging and administration. Different forms of tablets have been primarily devised to meet the needs of select populations while maintaining the integrity of the active pharmaceutical ingredient. Some populations, notably infants and young children, cannot swallow tablets or capsules or find it difficult to do so. In these instances, a tablet that dissolves under the tongue, in the mouth, or in a specified liquid, or one that could be harmlessly chewed would be beneficial. Capsules that could be opened and their contents sprinkled over a small amount of food or in a liquid would also be beneficial. Any improvement that eases the administration of a necessary medication or lessens the antagonism associated with said administration, without compromising the effectiveness of the active pharmaceutical ingredient, is worthwhile.

Other types of solid dosage forms such as thin strips, lollipops or gum bring a novel concept to the administration of medications to children. Aside from the obvious ease of administration from the viewpoint of the caregiver, there may be an added benefit. The administration of medication is oftentimes a private issue and the ability of a caregiver to provide a dose of medication in a seemingly matter-of-fact form may preserve that perception and instill in the user a mindset that views the administration as pleasant rather than monotonous or negative.

Liquid dosage forms also provide benefits of administration to infants and young children or anyone with compromised swallowing capability. Syrups, solutions and suspensions are easily swallowed. Unpleasant tastes can be masked by flavoring. An oral spray allows for the quick administration of a pre-measured dose of medication and supplies multiple metered doses in one handy device. With no need to aid swallowing (such as a glass of water, etc.) and the convenience of not having to rifle through a bottle of tablets, administration is simplified.

A tablet is a mixture of active substances and excipients, usually in powder form, pressed or compacted into a solid. The excipients include binders, glidants (flow aids) and lubricants to ensure efficient tableting; disintegrants to ensure that the tablet breaks up in the digestive tract; sweeteners or flavors to mask the taste of bad-tasting active ingredients; and pigments to make uncoated tablets visually attractive. A coating (sugar, enteric or film) may be applied to hide the taste of the tablet's components, to make the tablet smoother and easier to swallow, and to make it more resistant to the environment, extending its shelf life. Tablets may be buffered (by potassium metaphosphate, potassium phosphate, monobasic sodium acetate, etc.) to combat change in pH. Tablets may be delayed-release, sustained-release, extended-release, controlled-delivery, long-acting, orally-disintegrating or melts, among others, often denoting the pharmacokinetic profile of the active agent. A capsule-shaped tablet is a caplet.

Some tablets may be taken sublingually or allowed to dissolve in the mouth. The principle behind sublingual administration is simple. When a chemical comes in contact with the mucous membrane beneath the tongue, or buccal mucosa, it diffuses through it. Because the connective tissue beneath the epithelium contains a profusion of capillaries, the substance then diffuses into them and enters the venous circulation. Troches are medicated lozenges designed to dissolve in the mouth. Soluble tablets dissolve on contact with the tongue.

Slurry may be made when a dissolvable tablet containing a gelling agent is added to a liquid.

Tablets may also be micro-coated and placed in a capsule for administration.

The compositions described herein can be administered either alone or more typically in combination with one or more of a conventional pharmaceutical carrier, excipient buffer, stabilizer or the like. Such materials should be non-toxic and should not interfere with the efficacy of the active ingredient. The precise nature of the carrier or other material will depend on the route of administration. The term "excipient" is used herein to describe any ingredient other than the compound(s) (enzymes) used in the composition as described herein and known in the art.

Acceptable carriers are physiologically acceptable to the administered patient and retain the therapeutic properties of the compounds with/in which it is administered. Acceptable carriers and their formulations are and generally described in, for example, Remington' pharmaceutical Sciences (18th Edition, ed. A. Gennaro, Mack Publishing Co., Easton, Pa. 1990). Two exemplary carriers are water and physiological saline. The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject compounds from the administration site to a portion of the body. Each carrier is acceptable in the sense of being compatible with the other ingredients of the formulation and not injurious to a subject to whom it is administered. Nor should an acceptable carrier alter the specific activity of the subject compounds.

Acceptable carriers, excipients, or stabilizers are those that are non-toxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA (Ethylenediaminetetraacetic acid); sugars such as sucrose, mannitol, trehalose or sorbitol; salt-forming counter-ions such as sodium; and/or non-ionic surfactants such as TWEEN®, PLURONICS® or polyethylene glycol (PEG).

The phrase "pharmaceutically acceptable" refers to molecular entities and compositions that are physiologically tolerable and do not typically produce an allergic or similar untoward reaction, such as gastric upset, dizziness and the like, when administered to a human.

Dosing, Administration and Methods

Methods of preparing such dosage forms are known, or will be apparent, to those skilled in this art; for example, see Remington: The Science and Practice of Pharmacy, 21st Edition (Lippincott Williams & Wilkins. 2005). Appropriate dosages will depend on the patient (age, weight, overall health, etc.), the severity of the condition, the type of formulation and other factors known to those having ordinary skill in the art. It is to be noted that concentrations and dosage values can vary with the severity of the condition. It is to be further understood that for any particular patient, specific dosage regimens should be adjusted over time according to the individual need and the professional judgment of the person administering or supervising the administration of the compositions.

In one embodiment a composition can be administered 1 or more times a day, such as 1, 2, 3, 4, 5, 6, 7, 8, 9, or 10 times a day with or without food. In another embodiment, a composition can be administered orally 3 times a day with or without food.

The term "unit dose" when used in reference to a therapeutic composition refers to physically discrete units suitable as unitary dosage for humans, each unit containing a predetermined quantity of active material calculated to produce the desired therapeutic effect in association with the required diluent; i.e., carrier, or vehicle.

Provided herein are methods for administering the enzyme compositions/preparations. In one aspect, the methods include administering the pancreatic/digestive enzymes as coated preparations. In another aspect, the disclosure relates to a method of treatment comprising administering to a subject with a neurological or Neuropsychiatric Disorder, including but not limited to: Adjustment Disorders, Addiction, Alzheimer's Disease, Anxiety Disorders, Bipolar Disorder, Cognitive Disorders, Dementias, Dissociative Disorders, Eating Disorders, Impulse-Control Disorders, Mood Disorders, Sexual Disorders, Sleep Disorders, Psychotic Disorders such as Schizophrenic Disorders (e.g., Schizophrenia), Somatoform Disorders, Substance Abuse Disorders and Personality Disorders, or other behavioral or neurological condition in need of treatment with digestive enzymes, at least two doses of a composition comprising a therapeutically effective amount of a coated or uncoated digestive enzyme preparation comprising a core comprising a digestive enzyme. Determination of whether a subject is in need of treatment with an effective amount of digestive enzymes may be based on a determination that the subject has an enzyme deficiency.

In one aspect of the present disclosure, it is well known that determining a dosage regimen of the compound is well within the purview of those in the art. By way of example, the dose levels may range from 100 milligrams to 10 grams as determined by weight. Further activity of the enzymes may range from 100 units of activity to 1,500,000 units of activity per dose for amylases, lipases and proteases, respectively.

In another embodiment, the disclosure relates to methods of treatment comprising administering to a subject with a neurological or neuropsychiatric condition susceptible to treatment with digestive enzymes, at least two doses of a composition comprising a therapeutically effective amount of the coated digestive enzyme preparations. In certain embodiments, about 80% of the enzyme is released by about 30 minutes in a dissolution test performed at pH 6.0. In other embodiments, about 80% of the enzyme is released by about 30 minutes after the coated digestive enzyme preparations reach the small intestine.

The disclosure further relates in another aspect to the delivery of digestive enzymes with improved safety of administration. The lipid coat adds weight to the enzyme preparation, which reduces the potential for aerosolization. Previous uncoated enzymes have been shown to become aerosolized, and can therefore be inhaled and contact the nasal cavity or the lungs, causing injury to the mucosa of those taking and those administering the enzyme preparation.

The disclosure further relates to the improvement of administering a sachet preparation for delivery to children. The disclosure specifically relates to the administration of a coated or uncoated digestive enzyme preparation, housed in a sachet which allows for particular types of administration including but not limited to administration in food, drink, or direct administration into the oral cavity or directly into the GI system through a NG-tube, G-tube or other GI entrances. The use of a sachet delivery of enzymes has heretofore not been utilized in the enzyme preparations presently marketed. In one embodiment, the sachet represents a single unit dosage or multiple doses for a day. The sachet of a trilaminar pouch allows the enzyme or enzyme/lipid powder to remain stable, and allows for ease of administration.

The disclosure further relates to the administering of the coated or uncoated enzyme preparation in a sachet or pouch preparation for ease of delivery to children and adults. In some embodiments, the disclosure specifically relates to the administration of a coated or uncoated enzyme particle preparation, housed in a sachet or pouch. This facilitates administration, including but not limited to, administration in food or drink, direct administration into the oral cavity, or administration directly into the GI system through an NG-tube, G-tube or other GI entrances or deliveries.

Compositions comprising an effective amount of the compound may be administered via any conventional route including but not limited to oral, parenteral, intramuscular, intravenous, transmucosal, transdermal, suppository or other method. Further the oral administration can be in the form of pellets, capsules, caplets, beadlets, sprinkles, tablets, softgels or other carrier.

The pharmaceutical formulations can also be prepared for parenteral use. Such formulations typically take the form of sterile isotonic solutions of the active ingredient according to standard pharmaceutical practice.

In one embodiment of the present disclosure, the increase of protein digestion of an individual suffering from a Neuropsychiatric Disorder leads to the improvement of such disorders. In another embodiment, an individual suffering from or diagnosed with a Neuropsychiatric Disorder benefits from the administration of digestive enzymes since digestive enzymes aid in the protein digestion process. In one embodiment, the neuropsychiatric symptoms of an individual suffering from or diagnosed with the Neuropsychiatric Disorder is improved or alleviated from the administration of digestive enzymes.

The present invention provides a method for using digestive enzymes and their derivatives to alleviate the symptoms of Neuropsychiatric Disorders. The method comprises administering to the individual a digestive enzyme either naturally or recombinantly derived, or their derivatives, in an amount effective to reduce the symptoms of the Neuropsychiatric Disorder.

Provided herein are methods of preventing one or more symptoms associated with a Neuropsychiatric Disorder by administering a composition described herein. As used herein, "prevention" refers to prophylaxis, prevention of onset of symptoms, prevention of progression of a Neuropsychiatric Disorder. As used herein, "inhibition", "prevention", "treatment" and "treating" refer to, for example, stasis of symptoms, as well as partial or full amelioration of one or more symptoms associated with a Neuropsychiatric Disorder. The compositions described herein may be used to minimize the developmental disruption associated with Schizophrenia. Patients may be assessed with respect to the prodromal (pre-onset) phase of the illness, which can be detected up to 30 months before the onset of symptoms. Administration of the compositions may be used to limit or reduce the number of patients who go on to develop Schizophrenia, experience transient or self-limiting psychotic symptoms and the non-specific symptoms of social withdrawal, irritability, dysphoria, and clumsiness during the prodromal phase.

Compositions can be administered to a patient in an amount that is effective for producing some desired therapeutic effect by alleviating one or more symptoms associated with a Neuropsychiatric Disorder at a reasonable benefit/risk ratio applicable to any medical treatment. A therapeutically effective amount is an amount achieves at least partially a desired therapeutic or prophylactic effect in tissue subject. The amount of digestive enzymes necessary to bring about alleviation one or more symptoms associated with a Neuropsychiatric Disorder is not fixed per se. The amount of digestive enzymes administered may vary with the type of disorder, extensiveness of the disorder, and size of the patient suffering from the disorder. A response is achieved when the patient experiences partial or total alleviation, or reduction of one or more signs or symptoms of illness. The patient's symptoms can remain static (i.e., not get worse) or can be reduced.

A physician can readily determine and prescribe the effective amount (ED50) of the composition required. For example, the physician could start doses of the compounds employed in the composition at levels lower than that required in order to achieve the desired therapeutic effect and gradually increase the dosage until the desired effect is achieved. Alternatively, a dose can remain constant.

In such methods of treatment, one or more symptoms are ameliorated or reduced following administration of a composition provided herein. In one embodiment, one or more symptoms of such disorders are reduced in severity or duration by about 2%, about 5%, about 10%, about 15%, about 20%, about 25%, about 30%, about 35%, about 40%, about 45%, about 50%, about 55%, about 60%, about 65%, about 70%, about 75%, about 80%, about 90%, about 95%, or about 100%. In another embodiment, one or more symptoms of such disorders are reduced in severity or duration by about 2-fold, about 5-fold, about 10-fold, about 15-fold, about 20-fold, about 25-fold, about 30-fold, about 35-fold, about 40-fold, about 45-fold, about 50-fold, about 55-fold, about 60-fold, about 65-fold, about 70-fold, about 75-fold, about 80-fold, about 90-fold, about 95-fold, about 100-fold or more.

The DSM IV Diagnostic Criteria for Schizophrenia may be used to assess whether administration of a composition described herein reduces the severity and/or duration of one or more symptoms of Schizophrenia.

In one embodiment, one or more characteristic symptoms are reduced in severity and/or duration following administration of a composition described herein. For example, two (or more) of the following, each present for less than half or less than a quarter of a 1-month period (or less if successfully treated): delusions, hallucinations, disorganized speech (e.g., frequent derailment or incoherence), grossly disorganized or catatonic behavior, negative symptoms, i.e., affective flattening, alogia, or avolition.

In another embodiment, signs of social/occupational dysfunction are improved following administration of a composition described herein. That is, a patient may exhibit an improvement in one or more major areas of functioning such as work, interpersonal relations, or self-care.

In yet another embodiment, the duration of symptoms may be reduced in severity and/or duration following administration of a composition described herein. That is, continuous signs of disturbance that meet Criterion A may persist for less than 6 months, 5 months, 4 months, 3 months, 2 months, 1 month, 3 weeks, 2 weeks or 1 week.

Another aspect provided herein is combination therapy of a patient with a composition described herein along with another therapeutically effective agent or rehabilitation.

In one embodiment, the one or more agents are an antipsychotic medication. Exemplary antipsychotic medications are dopamine antagonists and serotonin antagonists.

Examples of dopamine antagonists include, but are not limited to: Acepromazine, Amisulpride, Amoxapine, Azaperone, Benperidol, Bromopride, Butaclamol, clomipramine (mild), chlorpromazine, chlorprothixene, clopenthixol, Clozapine, domperidone, droperidol, eticlopride, flupenthixol, fluphenazine, fluspirilene, haloperidol, iodobenzamide, loxapine, mesoridazine, levomepromazine, metoclopramide, nafadotride, nemonapride, Olanzapine, penfluridol, perazine, perphenazine, pimozide, prochlorperazine, promazine, quetiapine, raclopride, remoxipride, risperidone, piperone, spiroxatrine, stepholidine, sulpiride, sultopride, tetrahydropalmatine, thiethylperazine, thioridazine, thiothixene, tiapride, trifluoperazine, trifluperidol, triflupromazine, and ziprasidone.

Examples of serotonin antagonists include, but are not limited to, 5-HT3 antagonists, 5-HT2A receptor antagonists (e.g., ketanserin, which 5 HT2A, 5 HT2C, and alpha 1 receptors).

In another embodiment, therapeutically effective rehabilitation includes, but is not limited to, psychotherapy, vocational rehabilitation, social rehabilitation, or a combination thereof.

In another embodiment of the disclosure a transgenic mouse as described by Ratty et al. (U.S. Pat. No. 5,723,719) and incorporated herein by reference, is utilized to examine the efficacy of the digestive enzyme preparation with respect to administration of an effective amount of the enzyme and evaluating the enzyme's effect on the circling phenotype of the transgenic mouse.

The application of these enzymes of the high protease classification as applied to the chakragati mouse represents a novel discovery for the use of enzymes for Neuropsychiatric Disorders.

In one embodiment, the digestive enzyme has an effect on the circling behavior and thus on Neuropsychiatric Disorders including such conditions as Schizophrenia.

Studies with mouse models can effectively identify molecules or compounds which may effectively change behaviors in humans. The scale-up of such findings in mice is part of the traditional drug development pathway.

The chakragati (ckr) mouse, the result of a transgenic insertional mutation, exhibits an abnormal circling behavior in response to environmental stress cues, such as cage banging. Wild-type littermates and those that were heterozygous for the transgene insertion did not exhibit this circling phenotype. Analysis of the ckr mouse genome indicates genetic rearrangements on mouse chromosome 16. A US Patent was granted for the chakragati mouse (U.S. Pat. No. 5,723,719).

Since its discovery, extensive genetic, pharmacological and behavioral research has been carried out on the ckr mouse. The research undertaken points to the utility of the ckr mouse as a screening tool for neuropsychiatric drug discovery. Cerca Insights Sdn Bhd has developed a cascade of assays, the ckr screen, to characterize the properties of novel antipsychotic compounds. The insights generated from the ckr screen may be used to enhance the assessment of efficacy across the positive, negative and cognitive domains of Schizophrenia.

The endophenotypes that have been reported in the literature with respect to the ckr mouse are as follows: Asymmetric Up-regulation of Dopaminergic Tone, Circling, Hyperactivity, Prepulse Inhibition Deficit, Latent Inhibition (LI), Social Withdrawal, Lateral Ventricular Enlargement, Agenesis of the Corpus Callosum, and Reduction of Myelinated Neurons in Striatum.

The human clinical manifestations of the above mouse endophenotypes are as follows: Left hemi-spatial preference may be linked to asymmetric striatal dopaminergic activity common to all psychoses. A subgroup of Schizophrenia patients has underlying right striatal hyper-dopaminergia. There is a greater pathological involvement of the dominant hemisphere in Schizophrenia and of the non-dominant hemisphere in Bipolar Disorder. (Lyon et al 1992; Bracha 1989; Lohr & Caliguiri 1995).

Yet another human clinical manifestation of the above endophenotypes: Left-prone circling behavior (neglect of right-sided turning) was found in unmedicated schizophrenic patients. A tendency was noted for circling to occur more frequently among paranoid than nonparanoid schizophrenics. (Bracha 1987; Marder & Woods 1987).

Yet another human clinical manifestation of the above endophenotypes: hyperactivation (reduced task-related suppression) of default regions and hyperconnectivity of the default network may contribute to disturbances of thought in Schizophrenia and risk for the illness. (Whitfield-Gabrelli et al 2009).

Yet another human clinical manifestation of the above endophenotypes: impairment in prepulse inhibition (PPI) is generally seen as sensorimotor deficits. PPI disruption occurs in the prodromal stage of Schizophrenia and in patients with schizotypical personality disorder. (Quednow et al 2009; Kumari et al 2008; Kunugi et al 2007).

In yet another human clinical manifestation of the above endophenotypes: there is the absence of latent inhibition (LI) in the acute phase of Schizophrenia. LI is found to be correlated to the duration of the disease. (Rascle et al 2001; Gray & Snowden 2005; Vaitl D et al 2002).

In yet another human clinical manifestation of the above endophenotypes: longer duration of social withdrawal is evident in untreated disease. (Schultz et al 2007; Iyer 2008; Hoffman 2007).

In yet another human clinical manifestation of the above endophenotypes: ventricular enlargement represents a morphometric endophenotype for Schizophrenia. There is a significant correlation between the size of the lateral ventricles and underestimation of the metabolic activity of the caudate. (McDonald et al 2006; Berkataki et al 2006; Reig et al 2007).

In yet another human clinical manifestation of the above endophenotypes: reductions in the thickness of the anterior callosum differentiate between high-risk individuals who transition to psychosis and those who do not, which is highly predictive of transition. (Walterfang et al 2008).

In yet another human clinical manifestation of the above endophenotypes: myelin impairment is a key factor in the pathogenic loop of psychiatric diseases and drug Addiction. (Feng 2008).

The chakragati (ckr) mouse has been utilized as a model for Schizophrenia. Many "typical" and "atypical" antipsychotics have been tested on this mouse model prior to, and subsequent to approval in humans.

The circling phenotype exhibits a disruption in the endogenous genetic locus affecting motor function, and the circling behavior may represent an aberration associated with nigrostriatal neurons of the brain. This may affect multiple pathways of neurotransmission such as dopamine, adrenaline, noradrenaline, serotonin or GABA (gamma-Aminobutyric acid).

The chakragati mouse is a unique and validated animal model which tests "antipsychotic" potency of novel compounds. The mice exhibit a persistent overactivity of the dopamine system caused by a selective increase in striatal $D_2$ receptor subtypes. In general, antipsychotic medications are thought to reduce dopamine overactivity by the following mechanisms: 1) stimulating dopamine autoreceptors on dopamine neurons, thereby reducing functional activity of the dopamine system and 2) blocking post-synaptic dopamine receptors on dopaminoreceptive neurons or other neurotransmitter systems secondary to dopaminoreceptive neurons.

The chakragati (ckr) mouse has been proposed as a model of aspects of Schizophrenia. The mice, created serendipitously as a result of transgenic insertional mutation, exhibit spontaneous circling, hyperactivity, hypertone of the dopamine system, reduced social interactions, enlarged lateral ventricles, deficits in pre-pulse inhibition of acoustic startle and deficits in the latent inhibition of conditioned learning, (Dawe et al 2010). In 2010 Dawe et al studied the dose dependent effects of antipsychotic drugs (haloperidol, pimozide, risperidone, clozapine, olanzapine, ziprasidone, quetiapine and aripiprazole) on the spontaneous hyperactivity of the mice. All the antipsychotic drugs tested dose-dependently suppressed spontaneous hyperactivity. Aripiprazole, which is known to be a dopamine $D_2$ receptor partial agonist, exhibited a tri-phasic dose-response, initially suppressing hyperactivity at low doses, having little effect on hyperactivity at intermediate doses, and suppressing activity again at high doses. These data suggest that the spontaneous circling and hyperactivity of the ckr mouse may allow screening of candidate antipsychotic compounds, distinguishing compounds with aripiprazole-like profiles.

Aripiprazole, (also known as ABILIFY®) is an antipsychotic of a novel class acting as a partial and selective dopamine agonist, produced a different pattern of change in locomotor activity across doses. At lower doses (1.67-10 mg/kg) it produced an apparently dose-dependent reduction in motor activity followed by an increase in motor activity (15 mg/kg) and a subsequent suppression of motor activity (30 mg/kg). It a may be that this multiphasic pattern of change in motor activity across doses reflects the dopamine receptor partial agonist activity of aripiprazole. Thus, the nature of the dose-dependent response in ckr mouse would be expected to differentiate a similar dose-dependent pattern of motor disturbance but the low level of basal activity in wild type mice would make this difficult to detect. Even haloperidol, which is associated with far stronger extrapyramidal motor side effects than aripiprazole, did not produce a significant suppression in the locomotor activity of control mice monitored during the dark cycle when they are most active, (Neuroscience, Dawe et al. 2010).

Figure 6:
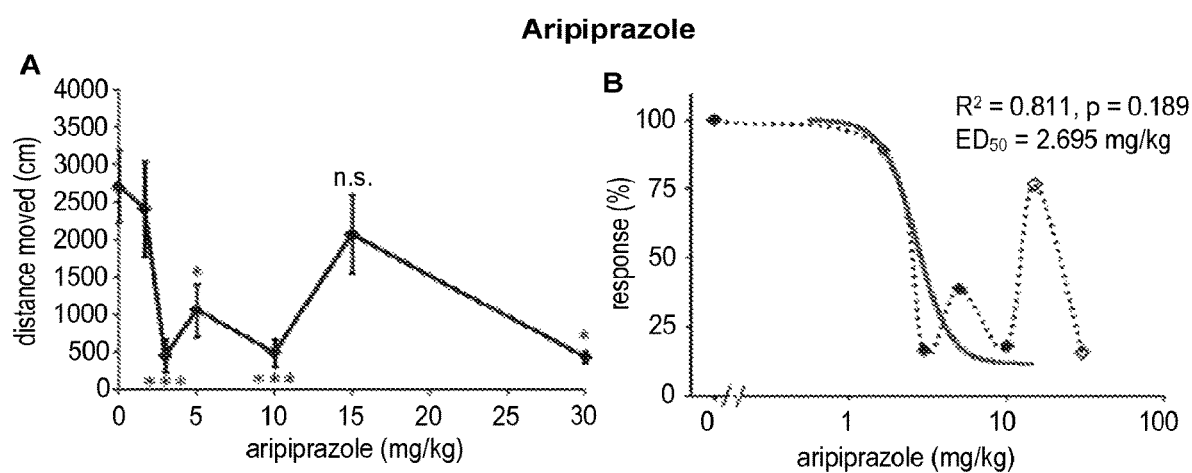
FIG. 6. Aripiprazole Dose Dependent Response in ckr Mice.

Administration of aripiprazole dose-dependently reduced the locomotor activity of ckr mice ($F6,54\_4.626$, $P\_0.001$; FIG. 6B). Post-hoc Dunnett's test comparisons with the vehicle control revealed that doses of 3-10 mg/kg significantly reduced locomotor activity. The response appeared to be multiphasic as a higher dose of 15 mg/kg did not significantly suppress locomotor activity while a higher still dose of 30 mg/kg again significantly suppressed locomotor activity. Observationally, the dose of 30 mg/kg appeared to be associated with marked overall suppression of motor function suggestive of severe sedation. Although it was not possible to fit the dose response curve function to the complete data set; it was possible to fit a subset of the data describing the initial suppression of activity at doses from 1.67 to 10 mg/kg with a curve predicting an ED50 of 2.695 mg/kg (FIG. 6B). However, the responses predicted by the function fitted failed to correlate with the actual values observed ($R2\_0.811$, $P\_0.189$), (Dawe et al 2010).

Thus ckr mice homozygous for the transgene insertion show a constellation of anatomical, biochemical and behavioral deficits which resemble those often reported in schizophrenic patients, as shown in the following Table. (Torres et al 2008).

| Condition | Schizophrenia | Ckr Mice |
|---|---|---|
| Aberrant Behaviors | | |
| Circling Behavior & Hyperactivity | Yes | Yes |
| Sensorimotor Gating Deficits | Yes | Yes |

-continued

| Condition | Schizophrenia | Ckr Mice |
|---|---|---|
| Brain Pathologies | | |
| Ventricular Enlargement | Yes | Yes |
| Myelination Abnormalities | Yes | Yes |
| Metabolic Deficits | Yes | Yes |
| Response to Antipsychotics | | |
| Clozapine and Olanzapine | Yes | Yes |
| Neurochemical Correlates | | |
| Alterations in Dopamine Systems | Yes | Yes |
| Deficit is in Choline and N-acetylaspartate | Yes | Yes |
| Typical Age of Onset of Pathology | | |
| Early Adulthood | Yes | Yes** |
| Sex-Dependent Prevalence of Disease | | |

*Human and mice share important genomic, anatomical and physiological similarities. These similarities, particularly in the genes involved in brain development, might provide insight into disease pathogenesis. {. . .}
**(Postnatal Day 10 for onset of Aberrant Behaviors)
(Torres 2008)

The validity of the ckr mouse mutant for understanding the pathogenesis of Schizophrenia is further supported in its ability to respond to antipsychotic drug treatment. The most salient endophenotype in the chakragati (ckr) mouse is its circling behavior. Under conditions of subjective stress, the mutant mouse shows consistent circling behavior with individual turns from 10 to 80 full body turns per minute. This behavior syndrome is also characterized by lateral circling behavior (i.e. a left-preference population bias), postural asymmetry and hyperactivity to sensory stimuli. In this context drugs that block the N-Methyl-D-Aspartate (NMDA) subtype of the glutamate receptor such as phencyclidine (PCP, also known as angel dust) and ketamine (a dissociate anesthetic), usually elicit a psychotic-like-state that resembles Schizophrenia in preclinical models of the disease. This psychotic-like state includes aberrant behavior syndromes (i.e. positive symptoms) similar to those listed for the ckr mouse. It should be noted that atypical neuroleptics such as clozapine and olanzapine (antipsychotic agents that selectively alleviate symptoms of Schizophrenia) also alleviate the lateralized circling behavior and aberrant postural asymmetry exhibited by the ckr mouse (Torres et al 2008).

EXAMPLES

Example 1. Pancreatin

Pancreatin is a substance comprising enzymes, principally amylase, lipase, and protease, obtained from the pancreas of the hog, Sus scrofa Linné var. domesticus Gray (Fam. Suidae) or of the ox, Bos taurus Linné (Fam. Bovidae). Pancreatin contains, in each mg, not less than 25 U.S.P. units of amylase activity, not less than 2 U.S.P. units of lipase activity, and not less than 25 U.S.P. units of protease activity. Pancreatin of a higher digestive power may be labeled as a whole-number multiple of the three minimum activities or may be diluted by admixture with lactose, or with sucrose containing not more than 3.25 percent of starch, or with pancreatin of lower digestive power.

Example 2. Pancrelipase

Pancrelipase is a substance containing enzymes, principally lipase, with amylase and protease, obtained from the pancreas of the hog, Sus scrofa Linné var. domesticus Gray (Fam. Suidae). It contains, in each mg, not less than 24 U.S.P. Units of lipase activity, and not less than 100 U.S.P. Units of amylase activity, and not less than 100 U.S.P. Units of protease activity.

The drug substance, pancreatic enzyme concentrate (porcine origin) is purchased from an appropriate supplier. The properties of an exemplary pancreatic enzyme concentrate (pancreatin) suitable for use in the products of this invention are described in the table below.

| Parameter | U.S.P. Specification |
|---|---|
| Protease (USP) | NLT 25 U.S.P. units/dose |
| Lipase (USP) | NLT 2 U.S.P. units/dose |
| Amylase (USP) | NLT 25 U.S.P. units/dose |
| Fat (USP) | NMT 6.0%* |
| Loss on Drying (USP) | NMT 5.0% |
| Escherichia coli (USP) | Neg/10 g |
| Salmonella species (USP) | Neg/10 g |

*If less than 75 U/mg Protease, 6 U/mg Lipase or 75 U/mg Amylase, then specification is NMT 3.0%

Example 3. Mouse Model Study I

Attenuation of hyperactivity in the ckr mouse has been shown to be predictive of antipsychotic efficacy. By way of testing digestive enzymes to determine their effect on the circling behavior and hyperactivity of the ckr transgenic mouse, two strengths of the enzyme CM100 were tested on the mouse. (FIG. 1). CM100 was administered twice daily for 14 days.

Dosing of the ckr mouse was separated into two strengths: a 10 mg pancreatin suspended in 1 mL of water and a second dosage of 20 mg of pancreatin suspended in 1 mL of water. (FIG. 2). The vehicle used was autoclaved reverse osmosis water. The dosage regimen consisted of twice daily dosing for 14 days at 0800 hours and 2000 hours. Oral gavage was the route of administration. A 20G autoclavable gavage needle was utilized, and the administration was done at 0.1 ml/10 g BW. The methodology as described may be altered accordingly as one skilled in the art of administration of enzymes or administration via gavage methodology to mice. One ordinarily skilled in the art would be able to administer the enzyme.

The instant disclosure is comprised of an enzyme preparation comprised of amylases, proteases and lipases. Doses used had a human equivalent strength of between 155,000 and 310,000 units of protease activity, the main component of the enzyme preparation. (FIG. 3).

Dosing of the ckr mouse commenced Day 1 and continued to Day 14. Dosing was conducted twice daily for 14 days, once in the morning between 7 am and 8 am and once in the evening between 7 pm and 8 pm (12 hours apart). The open field assays were conducted on 6 days: Day 1, Day 3, Day 7, Day 14, Day 15 and Day 18. Distance moved was recorded in 10 min-bins during the 20 minutes monitoring period. Results were compared to the data for the same parameters for 10 minutes determined for untreated ckr mice in prior experiments (n=54).

For the 20 mg/ml (high dose), one-way ANOVA showed significant changes in distance moved, ($F6,87=3.1713$, $p=0.0076$). Paired t-test showed significant differences in velocity between UNTREATED/D1 ($t=1.98969$, $p=0.0011$)*, UNTREATED/D3 ($t=1.98969$, $p=0.0454$), UNTREATED/D7, ($1=1.98969$, $p=0.0157$) and UNTREATED/D18, (t=1.98969, p=0.0203)**. Tukey-Kramer test showed significance between UNTREATED/D1 with p<0.05.

2-way ANOVA showed significant differences in distance moved between low and high dose subjects across time (F1,14=5.3582, p=0.0363). Within the subjects of high and low dose, there are significant differences across time (F5, 10=4.4951, p=0.0209).

For 20 mg/ml (high dose), one-way ANOVA showed significant changes in velocity (F6,87=3.1984, p=0.0072). Paired t-test showed significant differences in velocity between UNTREATED/D1 (t=1.98969, p=0.0009)*, UNTREATED/D3 (t=1.98969, p=0.0399), UNTREATED/D7, (1=1.98969, p=0.0211) and UNTREATED/D18, (t=1.98969, p=0.0201)**.

Example 4. Mouse Model Study II

Dosing of the ckr mouse was separated into two strengths: a 10 mg pancreatin suspended in 1 mL of water and a second dosage of 20 mg of pancreatin suspended in 1 mL of water. (FIG. 2). The vehicle used was autoclaved reverse osmosis water. The dosage regimen consisted of twice daily dosing for 14 days at 0800 hours and 2000 hours. Oral gavage was the route of administration. A 20G autoclavable gavage needle was utilized, and the administration was done at 0.1 ml/10 g BW. The methodology as described may be altered accordingly as one skilled in the art of administration of enzymes or administration via gavage methodology to mice. One ordinarily skilled in the art would be able to administer the enzyme.

The instant disclosure is comprised of an enzyme preparation comprised of amylases, proteases and lipases. Doses used had a human equivalent strength of between 155,000 and 310,000 units of protease activity, the main component of the enzyme preparation. (FIG. 3).

Dosing commenced Day 1 and continued to Day 14. Dosing was conducted twice daily for 14 days, once in the morning between 7 am and 8 am and once in the evening between 7 pm and 8 pm (12 hours apart). The open field assays were conducted on 6 days: Day 1, Day 3, Day 7, Day 14, Day 15 and Day 18. Velocity was recorded in 10 min-bins during the 20 minute monitoring period. These were compared to the data for the same parameters for 10 minutes determined for untreated ckr mice in prior experiments (n=54).

For 20 mg/ml (high dose), one-way ANOVA showed significant changes in velocity (F6,87=3.1984, p=0.0072). Paired t-test showed significant differences in velocity between UNTREATED/D1 (t=1.98969, p=0.0009)*, UNTREATED/D3 (t=1.98969, p=0.0399), UNTREATED/D7, (1=1.98969, p=0.0211) and UNTREATED/D18, (t=1.98969, p=0.0201).

Tukey-Kramer test showed significance between UNTREATED/D1 with p<0.05.

2-way ANOVA showed significant differences in velocity between low and high dose subjects across time (F1, 14=5.0932, p=0.0405). Within the subjects of high and low dose, there are significant differences across time (F5, 10=4.6769, p=0.0184).

Example 5: Mouse Model Study III

Figure 7:
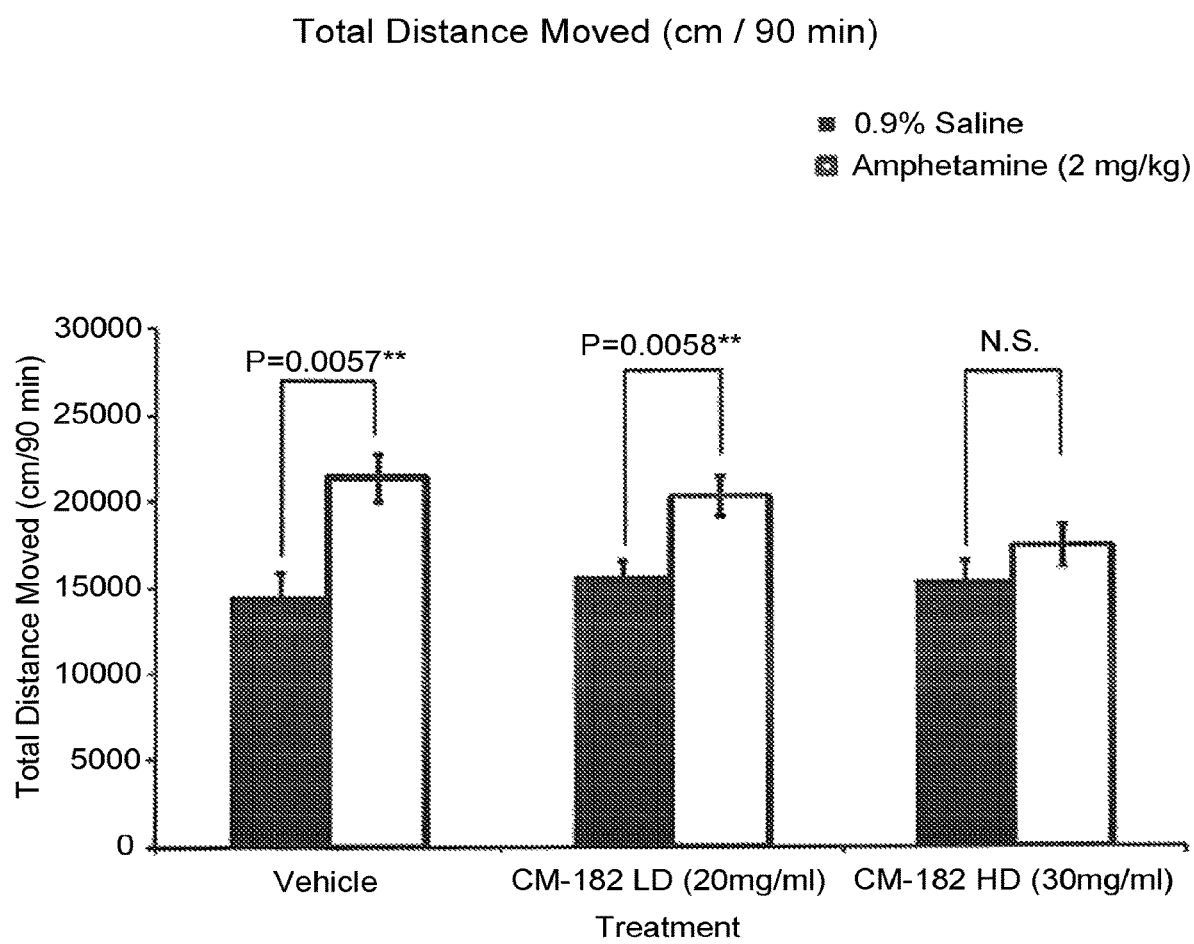
FIG. 7. Total distance moved in the 90 min recording of spontaneous open field test on male B6 mice. Data plot as Mean±SEM. Pair-wise comparison using Student's t-test. $\alpha=0.05$. *, $p<0.05$; , $p<0.01$; *, $p<0.001$; N.S., not significant.
Figure 8:
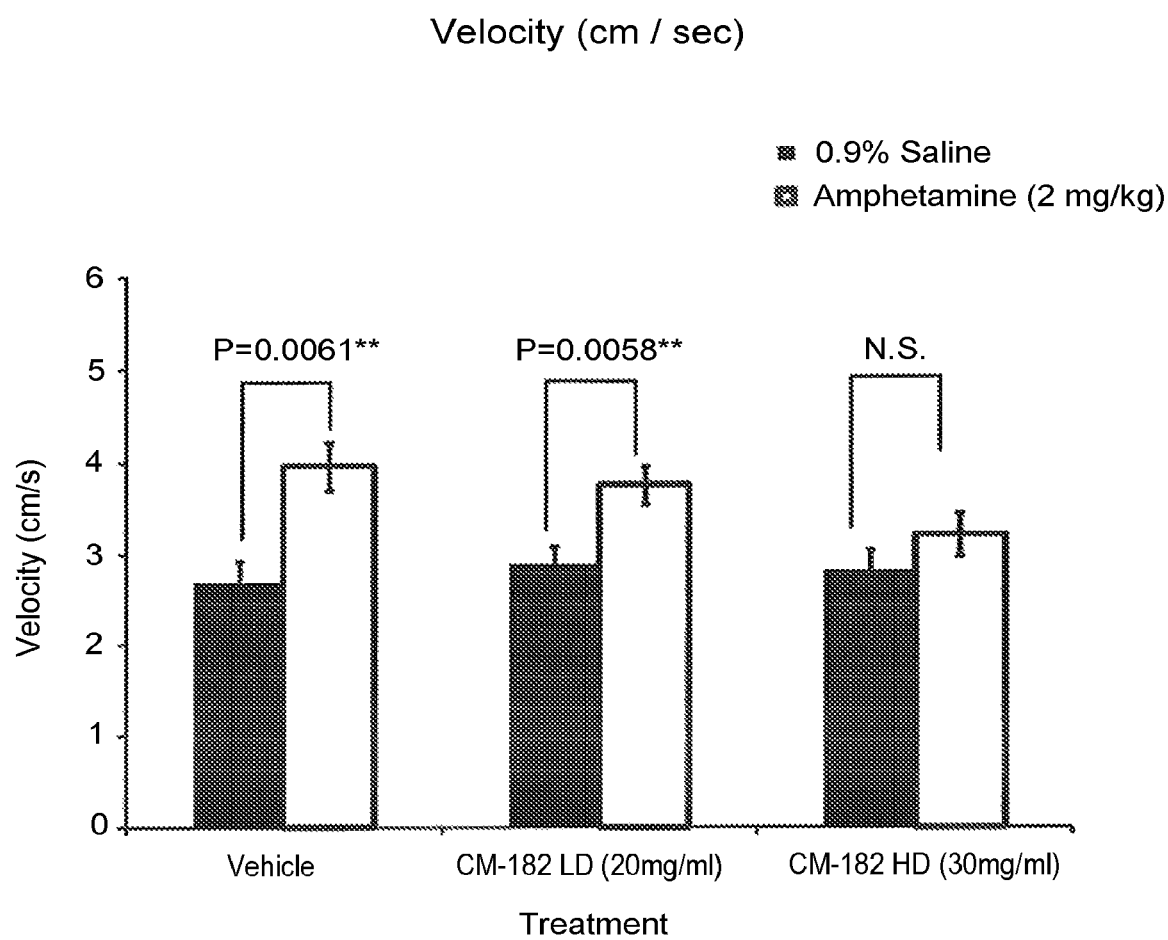
FIG. 8. Velocity in the 90 min recording of spontaneous open field test on male B6 mice. Data plot as Mean±SEM. Pair-wise comparison using Student's t-test. $\alpha=0.05$. *, $p<0.05$; , $p<0.01$; *, $p<0.001$; N.S., not significant.

Amphetamine-induced hyperactivity as a model of psychosis in Schizophrenia is well established in the industry. FIGS. 7 and 8 are two graphs that depict the results of administration of CM-182 at 30 mg/ml (i.e., approximately 465,000 units of protease) to mice injected with amphetamine to induce hyperactivity and to mice injected with saline as a control.

The dose significantly attenuated the amphetamine-induced hyperactivity, noted as an insignificant difference between the two groups of mice in total distance moved in FIG. 7 and in velocity in FIG. 8. It was also observed that CM-182 did not affect baseline activity in these mice, suggesting that the attenuation of hyperactivity occurred in a manner unrelated to sedation. Essentially, the administered compound is non-sedating. What the present inventors have identified is that significance exists between the two of the groups in both graphs (but not in the 30 mg/ml group), suggesting that the amphetamine did indeed induce hyperactivity to begin with.

While preferred embodiments have been shown and described herein, such embodiments are provided by way of example only. Numerous variations, changes and substitutions may occur without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A method for treating a Schizophrenia or a Schizophreniform Disorder in a subject in need thereof, comprising administering to the subject a therapeutically effective amount of a pharmaceutical composition that comprises coated particles, wherein the coated particles comprise: (a) a core comprising digestive enzymes, and (b) a coating that coats the core; wherein the digestive enzymes are present in the coated particles in an amount of from about 70% to about 90% by weight, and wherein the Schizophrenia or the Schizophreniform Disorder are treated.

2. The method of claim 1, wherein the digestive enzymes comprise a protease, an amylase, and a lipase.

3. The method of claim 1, wherein the coating comprises an enteric coating.

4. The method of claim 1, wherein the coating comprises a lipid, a lipid mixture, or a blend of lipid and emulsifiers.

5. The method of claim 4, wherein the coating comprises the lipid, and the lipid comprises an animal lipid or a vegetable lipid.

6. The method of claim 1, wherein the coating comprises an emulsifiable lipid.

7. The method of claim 1, wherein the coating comprises a crystallizable lipid.

8. The method of claim 1, wherein the coating comprises monoglycerides, diglycerides, triglycerides, fatty acids, esters of fatty acids, phospholipids, salts thereof, or a combination thereof.

9. The method of claim 1, wherein the digestive enzymes are present in the coated particles in an amount of from about 75% to about 85% by weight.

10. The method of claim 1, wherein the digestive enzymes are present in the coated particles in an amount of from about 77.5% to about 82.5% by weight.

11. The method of claim 1, wherein the pharmaceutical composition is administered to the subject three times a day with food.

12. The method of claim 2, wherein the protease is present in the pharmaceutical composition in an amount of from about 5,000 to about 1,500,000 U.S.P. units/dose, the amylase is present in the pharmaceutical composition in an amount of from about 1,000 to about 15,000,000 U.S.P.

units/dose, and the lipase is present in the pharmaceutical composition in an amount of from about 1,500 to about 282,000 U.S.P. units/dose.

13. The method of claim 2, wherein the protease and the lipase are present in the pharmaceutical composition in ratio of total protease to total lipase in U.S.P. units in a ratio of from about 5.371 to about 20:1.

14. The method of claim 2, wherein the protease is present in the pharmaceutical composition in an amount of about 140,000 U.S.P. units/dose, the amylase is present in the pharmaceutical composition in an amount of about 144,000 U.S.P. units/dose, the lipase is present in the pharmaceutical composition in an amount of about 23,000 U.S.P. units/dose.

15. The method of claim 1, wherein the pharmaceutical composition is a dosage formulation selected from the group consisting of a capsule, a tablet, a sprinkle, a powder, a pellet, and a caplet.

16. The method of claim 1, wherein the method further comprises administering an antipsychotic medication to the subject.

17. The method of claim 16, wherein the antipsychotic medication is a dopamine antagonist or a serotonin antagonist.

18. The method of claim 1, wherein the method further comprises administering to the subject psychotherapy, vocational rehabilitation, social rehabilitation, or a combination thereof.

19. The method of claim 1, wherein the digestive enzymes are present in the coated particles in an amount of about 70%, about 75%, about 77.5%, about, 80%, about 82.5%, about 85%, or about 90% by weight.

20. The method of claim 4, wherein the coating comprises the lipid, and the lipid comprises a hydrogenated soy oil.

* * * * *